US012606816B2

(12) United States Patent
Campbell et al.

(10) Patent No.: US 12,606,816 B2
(45) Date of Patent: Apr. 21, 2026

(54) INHIBITORY T CELL RECEPTOR PEPTIDES AND DISCOVERY METHODS

(71) Applicant: JANUX THERAPEUTICS, INC., San Diego, CA (US)

(72) Inventors: David Campbell, La Jolla, CA (US); Ramesh Bhatt, La Jolla, CA (US); Thomas Diraimondo, La Jolla, CA (US)

(73) Assignee: JANUX THERAPEUTICS, INC., La Jolla, CA (US)

( * ) Notice: Subject to any disclaimer, the term of this patent is extended or adjusted under 35 U.S.C. 154(b) by 1252 days.

(21) Appl. No.: 17/263,735

(22) PCT Filed: Jul. 31, 2019

(86) PCT No.: PCT/US2019/044552
§ 371 (c)(1),
(2) Date: Jan. 27, 2021

(87) PCT Pub. No.: WO2020/028595
PCT Pub. Date: Feb. 6, 2020

(65) Prior Publication Data
US 2021/0371849 A1 Dec. 2, 2021

Related U.S. Application Data

(60) Provisional application No. 62/712,521, filed on Jul. 31, 2018.

(51) Int. Cl.
*C07K 7/08* (2006.01)
*C12N 15/10* (2006.01)

(52) U.S. Cl.
CPC ............ *C12N 15/1037* (2013.01); *C07K 7/08* (2013.01)

(58) Field of Classification Search
CPC .............................. C12N 15/1037; C07K 7/08
See application file for complete search history.

(56) References Cited

U.S. PATENT DOCUMENTS

| | | | | |
|---|---|---|---|---|
| 8,283,446 B2 * | 10/2012 | Jakobsen | ......... | C07K 14/70503 530/350 |
| 8,378,074 B2 * | 2/2013 | Jakobsen | ................ | A61P 31/00 530/350 |
| 8,519,100 B2 * | 8/2013 | Jakobsen | ........... | C07K 16/2809 530/350 |

FOREIGN PATENT DOCUMENTS

| | | | | |
|---|---|---|---|---|
| WO | WO-9636881 A2 * | 11/1996 | ......... | C07K 14/7051 |
| WO | WO-0020581 A1 * | 4/2000 | ............. | A61P 35/00 |
| WO | WO-2020028595 A2 | 2/2020 | | |

OTHER PUBLICATIONS

Bentzen et al 2018 (Year: 2018).*
Cole et al 2017 (Year: 2017).*
Dionne et al 2003 (Year: 2003).*
Hafstrand Dissertation 2018 (Year: 2018).*
PCT/US2019/044552 International Search Report and Written Opinion dated Mar. 20, 2020.
Rudolph et al. A peptide that antagonizes TCR-mediated reactions with both syngeneic and allogeneic agonists: functional and structural aspects. J Immunol 172:2994-3002 (2004).
Wu et al. Advancement and applications of peptide phage display technology in biomedical science. J Biomed Sci 23:8 (2016).
Zhou et al. Phage display screening identifies a novel peptide to suppress ovarian cancer cells in vitro and in vivo in mouse models. BMC Cancer 15:889 (2015).

* cited by examiner

*Primary Examiner* — Catherine S Hibbert
(74) *Attorney, Agent, or Firm* — WILSON SONSINI GOODRICH & ROSATI

(57) ABSTRACT

Disclosed herein are methods of inhibiting an interaction of a T cell receptor with a peptide-major histocompatibility complex comprising administering inhibitory peptides that bind to the T cell receptor without the aid of a major histocompatibility complex to inhibit the interaction, and methods of identifying the inhibitory peptides.

6 Claims, 34 Drawing Sheets

Specification includes a Sequence Listing.

| Kd (M) | k$_{on}$ (1/M·s) | k$_{dis}$ (1/s) |
|---|---|---|
| 4.4E-09 | 2.0E+05 | 8.9E-04 |

| ID | Kd (M) | $k_{on}$ (1/M·s) | $k_{dis}$ (1/s) |
|---|---|---|---|
| Inhibitory peptide 1 | 7.95E-08 | 3.55E+05 | 2.82E-02 |

| Peptide | Amino Acid Sequence | | | | | | | | | | | | SEQ ID NO: |
|---|---|---|---|---|---|---|---|---|---|---|---|---|---|
| Mage-A3 | E | V | D | P | I | G | H | L | Y | | | | 1 |
| Inhibitory peptide 1 | V | S | C | K | D | V | Y | D | E | A | F | C | W | 2 |

| Phage Clone | Peptide ID | Phage ELISA | | | Peptide amino acid sequence from clonal phage | | | | | | | | | | | | | | | SEQ ID NO: |
|---|---|---|---|---|---|---|---|---|---|---|---|---|---|---|---|---|---|---|---|---|---|
| | | NAv bkgd | MAGE-A3 TCR | pMHC comp. %bound | N-term Glycine | 1 | 2 | 3 | 4 | 5 | 6 | 7 | 8 | 9 | 10 | 11 | 12 | 13 | 14 | |
| J44A09 | Inhibitory peptide 2 | 0.042 | 1.452 | 4.8% | G | E | S | C | Q | S | V | Y | D | S | S | F | C | Y | D | 11 |
| J44A02 | Inhibitory peptide 3 | 0.046 | 1.661 | 4.4% | G | N | A | C | E | M | T | Y | D | H | T | F | C | D | P | 12 |
| J44F06 | Inhibitory peptide 4 | 0.058 | 1.672 | 5.8% | G | R | I | C | E | E | V | Y | D | W | I | F | C | E | S | 13 |
| J44C03 | Inhibitory peptide 5 | 0.056 | 1.951 | 4.5% | G | R | R | C | V | D | V | Y | D | N | A | F | C | L | I | 14 |
| J44C01 | Inhibitory peptide 1 | 0.052 | 1.989 | 13.6% | G | V | S | C | K | D | V | Y | D | E | A | F | C | W | T | 15 |
| J44C09 | Inhibitory peptide 6 | 0.054 | 1.857 | 35.4% | G | T | S | C | A | Q | I | Y | D | F | E | F | C | Y | S | 16 |
| J44E01 | Inhibitory peptide 7 | 0.067 | 1.956 | 6.1% | G | S | L | C | S | L | V | Y | D | Q | D | F | C | E | S | 17 |
| J44C02 | Inhibitory peptide 8 | 0.053 | 1.247 | 9.0% | G | N | S | C | S | L | V | Y | D | K | A | F | C | L | F | 18 |
| J44G03 | Inhibitory peptide 9 | 0.059 | 1.806 | 7.1% | G | N | Q | C | W | E | V | Y | D | Q | E | F | C | S | L | 19 |
| J44H02 | Inhibitory peptide 10 | 0.065 | 1.771 | 6.4% | G | S | A | C | S | R | I | Y | D | F | A | F | C | H | T | 20 |
| J44F03 | Inhibitory peptide 11 | 0.054 | 1.118 | 20.0% | G | T | F | C | Y | F | D | H | G | L | V | N | C | Q | W | 21 |
| J44H11 | Inhibitory peptide 12 | 0.051 | 2.137 | 32.6% | G | H | C | F | V | S | P | A | S | G | E | W | W | C | V | 22 |
| J44A10 | Inhibitory peptide 13 | 0.297 | 1.781 | 13.3% | G | C | S | W | I | F | D | G | L | R | Y | F | S | K | C | 23 |
| J43A11 | Inhibitory peptide 14 | 0.116 | 1.314 | 14.3% | | V | R | T | W | F | E | K | F | P | E | L | V | | | 24 |
| J43A05 | Inhibitory peptide 15 | 0.059 | 1.339 | 21.6% | | L | V | W | G | C | I | W | D | D | M | C | S | | | 25 |
| | | | | | | | | | | | | | | | | | | | | |

FIG. 7A

| | | | | | | | | | | | | | | | | | | | |
|---|---|---|---|---|---|---|---|---|---|---|---|---|---|---|---|---|---|---|---|
| J43A09 | Inhibitory peptide 16 | 0.069 | 1.307 | 21.3% | | | W | H | W | E | P | S | M | V | W | G | M | L | | 26 |
| J44E08 | Inhibitory peptide 17 | 0.13 | 1.826 | 13.5% | G | G | G | C | F | V | S | P | A | T | G | F | T | W | C | V | 27 |
| J44B03 | Inhibitory peptide 18 | 0.112 | 1.955 | 13.8% | G | G | D | C | Q | P | D | S | V | W | S | Y | W | Y | C | R | 28 |
| J44B05 | Inhibitory peptide 19 | 0.158 | 1.953 | 15.9% | G | G | C | T | F | V | D | W | W | V | L | G | S | P | Y | C | 29 |
| J44C07 | Inhibitory peptide 20 | 0.055 | 1.430 | 19.2% | G | G | C | L | M | N | D | Y | Y | Y | L | W | G | G | H | C | 30 |
| | Inhibitory peptide 21 | | | | G | G | A | S | C | K | D | V | Y | D | E | A | F | C | W | T | 31 |
| | Inhibitory peptide 22 | | | | G | G | V | A | C | K | D | V | Y | D | E | A | F | C | W | T | 32 |
| | Inhibitory peptide 23 | | | | G | G | V | S | C | A | D | V | Y | D | E | A | F | C | W | T | 33 |
| | Inhibitory peptide 24 | | | | G | G | V | S | C | K | D | V | Y | D | A | A | F | C | W | T | 34 |
| | Inhibitory peptide 86 | | | | G | G | V | S | C | K | D | V | Y | D | E | A | F | C | A | T | 35 |
| | Inhibitory peptide 87 | | | | G | G | V | S | C | K | D | V | Y | D | E | A | F | C | W | A | 36 |

FIG. 7B

| Inhibitory Peptide ID | Peptide Amino Acid Sequence – Binding to MAGE-A3 TCR | ELISA | | Inhibitory Peptide + GGGGS Linker SEQ ID NO: |
|---|---|---|---|---|
| | | EC50 uM | IC50 uM | |
| Inhibitory peptide 2 (SEQ ID NO: 11) | GGESCQSVYDSSFCYDGGGGS[PEG4]Lys(biotin)-NH2 | 0.10 | 7.79 | 37 |
| Inhibitory peptide 3 (SEQ ID NO: 12) | GGNACEMTYDHTFCDPGGGGS[PEG4]Lys(biotin)-NH2 | 0.17 | 3.13 | 38 |
| Inhibitory peptide 4 (SEQ ID NO: 13) | GGRICEEVYDWIFCESGGGGS[PEG4]Lys(biotin)-NH2 | 0.31 | | 39 |
| Inhibitory peptide 5 (SEQ ID NO: 14) | GGRRCVDVYDNAFCLIGGGGS[PEG4]Lys(biotin)-NH2 | 0.25 | | 40 |
| Inhibitory peptide 1 (SEQ ID NO: 15) | GGVSCKDVYDEAFCWTGGGGS[PEG4]Lys(biotin)-NH2 | 0.01 | 0.60 | 41 |
| Inhibitory peptide 6 (SEQ ID NO: 16) | GGTSCAQIYDFEFCYSGGGGS[PEG4]Lys(biotin)-NH2 | 0.17 | 2.25 | 42 |
| Inhibitory peptide 7 (SEQ ID NO: 17) | GGSLCSLVYDQDFCESGGGGS[PEG4]Lys(biotin)-NH2 | 0.16 | 4.55 | 43 |
| Inhibitory peptide 8 (SEQ ID NO: 18) | GGNSCSLVYDKAFCLFGGGGS[PEG4]Lys(biotin)-NH2 | 0.43 | | 44 |
| Inhibitory peptide 9 (SEQ ID NO: 19) | GGNQCWEVYDQEFCSLGGGGS[PEG4]Lys(biotin)-NH2 | 0.05 | 3.10 | 45 |
| Inhibitory peptide 10 (SEQ ID NO: 20) | GGSACSRIYDFAFCHTGGGGS[PEG4]Lys(biotin)-NH2 | 0.33 | | 46 |
| Inhibitory peptide 11 (SEQ ID NO: 21) | GGTFCYFDHGLVNCQWGGGGS[PEG4]Lys(biotin)-NH2 | 0.50 | | 47 |
| Inhibitory peptide 12 (SEQ ID NO: 22) | GGHCFVSPASGEWWCVGGGGS[PEG4]Lys(biotin)-NH2 | 0.08 | >100 | 48 |
| Inhibitory peptide 13 (SEQ ID NO: 23) | GGCSWIFDGLRYFSKCGGGGS[PEG4]Lys(biotin)-NH2 | 0.15 | 90.89 | 49 |
| Inhibitory peptide 14 (SEQ ID NO: 24) | VRTWFEKFPELVGGGGS[PEG4]Lys(biotin)-NH2 | 0.67 | | 50 |
| Inhibitory peptide 15 (SEQ ID NO: 25) | LVWGCIWDDMCSGGGGS[PEG4]Lys(biotin)-NH2 | 0.10 | >100 | 51 |

FIG. 10A

| Inhibitory peptide 16 (SEQ ID NO: 26) | WHWEPSMVWGMLGGGGS[PEG4]Lys(biotin)-NH2 | 7.85 | | 52 |
|---|---|---|---|---|
| Inhibitory peptide 17 (SEQ ID NO: 27) | GGGCFVSPATGFTWCVGGGGS[PEG4]Lys(biotin)-NH2 | 2.34 | | 53 |
| Inhibitory peptide 18 (SEQ ID NO: 28) | GGDCQPDSVWSYWYCRGGGGS[PEG4]Lys(biotin)-NH2 | 0.27 | | 54 |
| Inhibitory peptide 19 (SEQ ID NO:29) | GGCTFVDWWVLGSPYCGGGGS[PEG4]Lys(biotin)-NH2 | 1.12 | | 55 |
| Inhibitory peptide 20 (SEQ ID NO: 30) | GGCLMNDYYYLWGGHCGGGGS[PEG4]Lys(biotin)-NH2 | 3.90 | | 56 |
| Inhibitory peptide 25 (SEQ ID NO: 1) | EVDPIGHLYGGGGS[PEG4]Lys(biotin)-NH2(MAGE-A3) | >10 | >100 | 57 |
| Peptide ID | Peptide Amino Acid Sequence – Binding to MAGE-A3 TCR | ELISA EC50 uM | ELISA IC50 uM | SEQ ID NO: |
| Inhibitory peptide 26 | ESDPIVAQYGGGGS[PEG4]Lys(biotin)-NH2(Titin) | >10 | | 58 |

FIG. 10B

Final gel

Final gel

| Theoretical MW(Da) | 56536.63 (SS) |
|---|---|
| Measured MW(Da) | 56536.45 (SS) |

| MAGE-A3 TCR Chain α | Peptide |
|---|---|
| CDR1: TYR32 | CYS-28 |
| CDR3: ARG94 | TYR-24 |
| CDR3: PHE102 | VAL-25 |

| MAGE-A3 TCR Chain β | Peptide |
|---|---|
| CDR3: MET98 | CYS-19, -28 |
| CDR3: MET98 | PHE-20 |
| CDR2: PHE51 | PHE-20 |
| CDR1: ARG31 | ASP-23 |
| CDR2: GLU49 | TYR-24 |
| CDR2: PHE51 | TYR-24 |
| CDR2: ARG56 | TYR-24 |

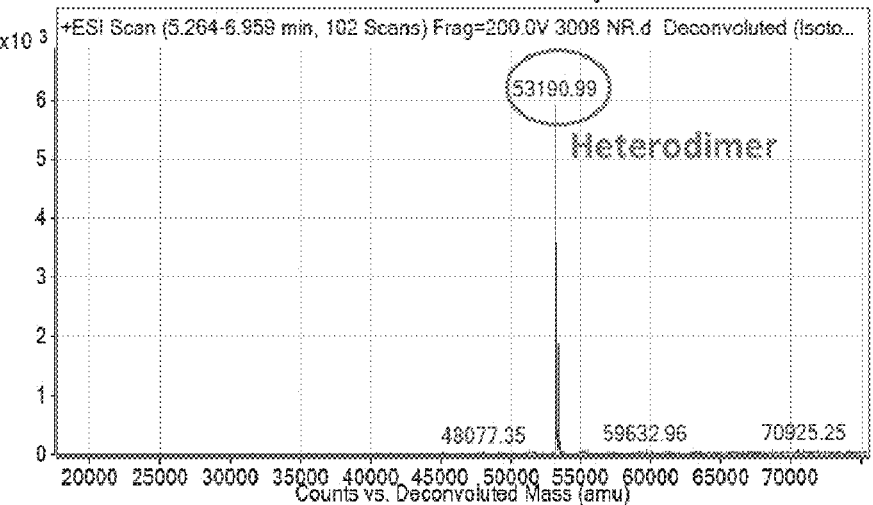
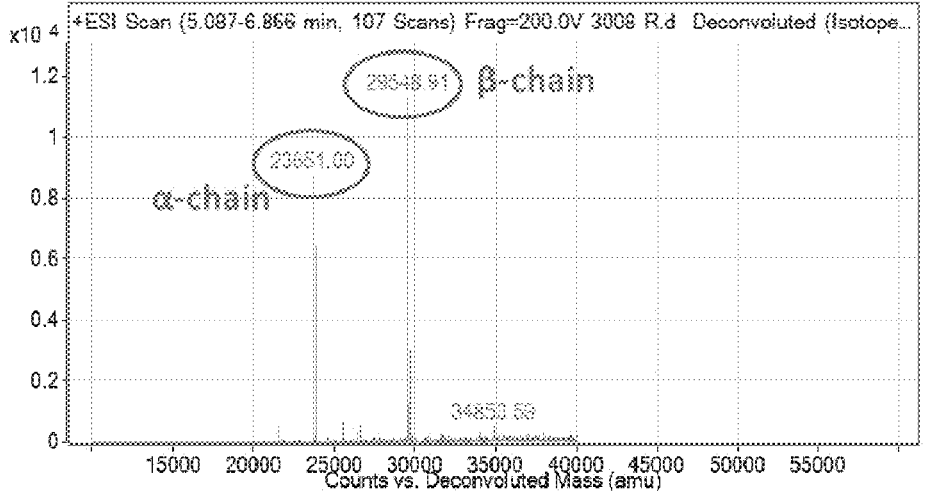
| gp100 TCR Theoretical MW(Da) | gp100 TCR Experimental MW(Da) | Difference (Da) |
|---|---|---|
| 53190.91 (-SH) | 53190.99 | -0.08 |
FIG. 16C

| Titrated gp100 TCR | $K_D$ (M) | $k_{on}$ (M$^{-1}$ s$^{-1}$) | $k_{off}$ (s$^{-1}$) |
|---|---|---|---|
| Captured gp100 pMHC | 7.07E-10 | 1.33E+05 | 9.38E-05 |

| Peptide | clone | Signal above bkgd | NAv bkgd | gp100 TCR | N-term Gly | | 1 | 2 | 3 | 4 | 5 | 6 | 7 | 8 | 9 | 10 | 11 | 12 | 13 | 14 | SEQ ID NO: |
|---|---|---|---|---|---|---|---|---|---|---|---|---|---|---|---|---|---|---|---|---|---|
| Inhibitory peptide 27 | J225E08 | 4.4 | 0.084 | 0.368 | G | G | A | L | C | P | Q | V | H | G | S | F | S | F | C | F | 59 |
| Inhibitory peptide 28 | J344F05 | 18.7 | 0.170 | 3.176 | G | G | C | H | W | E | H | V | W | G | A | G | S | F | F | C | 60 |
| Inhibitory peptide 29 | J419A04 | 39.3 | 0.075 | 2.933 | G | G | Y | D | C | N | Y | D | P | S | S | H | T | C | F | Y | 61 |
| Inhibitory peptide 30 | J419B05 | 29.0 | 0.104 | 3.017 | G | G | D | I | C | Q | W | V | R | S | M | T | E | C | S | W | 62 |
| Inhibitory peptide 31 | J420A02 | 36.6 | 0.080 | 2.928 | G | G | Y | C | Y | Y | D | I | D | L | D | Q | F | L | C | N | 63 |
| Inhibitory peptide 32 | J420A03 | 9.2 | 0.240 | 2.210 | G | G | W | C | S | Y | V | R | F | D | F | I | D | F | C | L | 64 |
| Inhibitory peptide 33 | J420B01 | 7.3 | 0.382 | 2.798 | G | G | T | C | I | W | F | D | V | E | S | W | L | S | C | F | 65 |
| Inhibitory peptide 34 | J420C11 | 42.2 | 0.068 | 2.857 | G | G | L | C | R | A | V | E | D | M | W | V | T | S | C | M | 66 |
| Inhibitory peptide 35 | J425A02 | 33.1 | 0.089 | 2.957 | G | G | I | C | Y | D | Y | M | S | G | Y | D | V | V | C | M | 67 |
| Inhibitory peptide 36 | J425B04 | 16.5 | 0.118 | 1.943 | G | G | H | C | Y | D | T | H | S | F | P | M | Y | V | C | L | 68 |
| Inhibitory peptide 37 | J425F05 | 22.0 | 0.092 | 2.009 | G | G | Y | C | P | L | S | Y | S | Q | Y | D | S | P | C | Y | 69 |
| Inhibitory peptide 38 | J431E03 | 42.4 | 0.049 | 2.086 | G | G | D | I | C | Q | W | V | K | H | E | S | Y | C | T | S | 70 |
| Inhibitory peptide 39 | J419C01 | 5.5 | 0.345 | 1.884 | G | G | F | L | C | Y | L | Y | E | H | N | G | A | C | L | L | 71 |
| Inhibitory peptide 40 | J424F11 | 12.1 | 0.198 | 2.407 | G | G | M | F | C | W | G | F | G | D | H | W | F | C | S | P | 72 |
| Inhibitory peptide 41 | J420G11 | 33.0 | 0.085 | 2.791 | G | G | D | C | W | W | F | P | S | D | P | H | P | F | C | F | 73 |
| Inhibitory peptide 42 | J420B11 | 11.1 | 0.095 | 1.055 | G | G | F | C | R | Y | V | R | Y | E | F | W | D | L | C | M | 74 |
| Inhibitory peptide 43 | J425B06 | 27.5 | 0.103 | 2.835 | G | G | H | C | Y | F | N | E | G | L | Q | Y | F | S | C | W | 75 |

FIG. 17A

| | | | | | | | | | | | | | | | | | | | |
|---|---|---|---|---|---|---|---|---|---|---|---|---|---|---|---|---|---|---|---|
| Inhibitory peptide 44 | J434D04 | 12.4 | 0.110 | 1.363 | G | G | I | C | Y | D | Y | M | A | G | D | D | V | L | C | M | 76 |
| Inhibitory peptide 45 | J434A03 | 11.3 | 0.063 | 0.707 | G | G | L | C | R | T | I | Y | S | Y | A | G | T | V | C | W | 77 |
| Inhibitory peptide 46 | J420D05 | 29.3 | 0.078 | 2.267 | G | G | L | C | S | Y | I | K | W | E | F | Q | Y | L | C | L | 78 |
| Inhibitory peptide 47 | J440F07 | 43.1 | 0.068 | 2.935 | G | G | L | C | Y | D | T | H | S | F | P | M | Y | V | C | L | 79 |
| Inhibitory peptide 48 | J420F08 | 11.5 | 0.072 | 0.824 | G | G | S | C | R | T | I | Y | E | Y | S | H | M | E | C | D | 80 |
| Inhibitory peptide 49 | J420A12 | 44.6 | 0.065 | 2.910 | G | G | V | C | D | W | P | T | S | D | M | E | W | W | C | F | 81 |
| Inhibitory peptide 50 | J425B12 | 5.6 | 0.536 | 3.023 | G | G | W | C | R | A | I | Y | R | Y | M | G | T | V | C | E | 82 |
| Inhibitory peptide 51 | J434C01 | 21.4 | 0.053 | 1.141 | G | G | Y | C | P | L | S | Y | S | H | D | D | I | P | C | Y | 83 |
| Inhibitory peptide 52 | J420H09 | 25.2 | 0.061 | 1.530 | G | G | Y | C | S | I | T | G | G | E | E | I | A | Q | C | V | 84 |
| Inhibitory peptide 53 | J344B01 | | | | G | G | I | F | P | C | L | S | D | R | W | L | C | V | D | F | 85 |
| Inhibitory peptide 54 | J344B06 | | | | G | G | I | F | P | C | L | S | D | R | W | L | C | V | D | F | 86 |
| Inhibitory peptide 55 | J344D11 | | | | G | G | I | F | P | C | L | S | D | R | W | L | C | V | D | F | 87 |

FIG. 17B

| Inhibitory Peptide ID | Peptide Amino Acid Sequence – Binding to gp100 TCR | ELISA EC50 uM | Inhibitory Peptide + GGGGS Linker SEQ ID NO: |
|---|---|---|---|
| Inhibitory peptide 28 (SEQ ID NO: 60) | GGCHWEHVWGAGSFFCGGGGS[PEG4]Lys(biotin)-NH2 | 1.26 | 88 |
| Inhibitory peptide 29 (SEQ ID NO: 61) | GGYDCNYDPSSHTCFYGGGGS[PEG4]Lys(biotin)-NH2 | 0.12 | 89 |
| Inhibitory peptide 30 (SEQ ID NO: 62) | GGDICQWVRSMTECSWGGGGS[PEG4]Lys(biotin)-NH2 | 0.17 | 90 |
| Inhibitory peptide 31 (SEQ ID NO: 63) | GGYCYYDIDLDQFLCNGGGGS[PEG4]Lys(biotin)-NH2 | 0.23 | 91 |
| Inhibitory peptide 33 (SEQ ID NO: 74) | GGFCRYVRYEFWDLCMGGGGS[PEG4]Lys(biotin)-NH2 | 0.54 | 92 |
| Inhibitory peptide 34 (SEQ ID NO: 66) | GGLCRAVEDMWVTSCMGGGGS[PEG4]Lys(biotin)-NH2 | 4.04 | 93 |
| Inhibitory peptide 35 (SEQ ID NO: 67) | GGICYDYMSGYDVVCMGGGGS[PEG4]Lys(biotin)-NH2 | 0.11 | 94 |
| Inhibitory peptide 36 (SEQ ID NO: 68) | GGHCYDTHSFPMYVCLGGGGS[PEG4]Lys(biotin)-NH2 | 2.58 | 95 |
| Inhibitory peptide 37 (SEQ ID NO: 69) | GGYCPLSYSQYDSPCYGGGGS[PEG4]Lys(biotin)-NH2 | 0.10 | 96 |

FIG. 20

| Titrated HIV TCR | $K_D$ (M) | $k_{on}$ (M$^{-1}$ s$^{-1}$) | $k_{off}$ (s$^{-1}$) |
|---|---|---|---|
| Captured HIV pMHC | 1.43E-09 | 1.53E+05 | 2.19E-04 |

| Peptide | clone | Signal above bkgd | NAv bkgd | HIV TCR | N term Gly | 1 | 2 | 3 | 4 | 5 | 6 | 7 | 8 | 9 | 10 | 11 | 12 | 13 | 14 | SEQ ID NO |
|---|---|---|---|---|---|---|---|---|---|---|---|---|---|---|---|---|---|---|---|---|
| Inhibitory peptide 56 | J374A01 | 8.8 | 0.1088 | 0.962 | G | G | D | P | C | N | I | Y | N | Y | W | T | T | C | V | T | 97 |
| Inhibitory peptide 57 | J398A03 | 26.7 | 0.072 | 1.926 | G | G | S | N | C | Y | S | L | E | P | W | I | Y | C | D | T | 98 |
| Inhibitory peptide 58 | J398A05 | 25.0 | 0.063 | 1.575 | G | G | L | V | C | N | D | G | N | I | W | W | L | C | E | D | 99 |
| Inhibitory peptide 59 | J398A06 | 23.4 | 0.085 | 1.983 | G | G | F | T | C | V | D | G | Q | V | Y | Y | L | C | D | S | 100 |
| Inhibitory peptide 60 | J398A07 | 31.0 | 0.066 | 2.046 | G | G | G | T | C | F | H | G | N | T | Y | F | L | C | E | D | 101 |
| Inhibitory peptide 61 | J398A08 | 29.2 | 0.065 | 1.890 | G | G | Q | T | C | I | A | D | N | V | Y | Y | L | C | P | E | 102 |
| Inhibitory peptide 62 | J398A10 | 20.6 | 0.094 | 1.938 | G | G | M | L | C | N | E | G | Y | W | A | L | S | C | F | L | 103 |
| Inhibitory peptide 63 | J398B04 | 18.2 | 0.074 | 1.343 | G | G | V | I | C | T | A | D | G | V | Y | W | L | C | D | L | 104 |
| Inhibitory peptide 64 | J398B05 | 24.4 | 0.072 | 1.748 | G | G | V | T | C | N | D | G | K | I | F | Y | L | C | S | D | 105 |
| Inhibitory peptide 65 | J398B12 | 37.5 | 0.054 | 2.016 | G | G | A | F | C | V | D | T | K | P | G | L | V | C | F | E | 106 |
| Inhibitory peptide 66 | J398C11 | 38.3 | 0.052 | 2.006 | G | G | A | T | C | H | L | D | N | V | Y | F | L | C | D | I | 107 |
| Inhibitory peptide 67 | J398D06 | 31.7 | 0.056 | 1.767 | G | G | T | T | C | L | E | G | V | Y | F | L | C | A | D | | 108 |
| Inhibitory peptide 68 | J398D08 | 22.4 | 0.060 | 1.335 | G | G | L | V | C | N | D | G | V | V | F | W | L | C | D | S | 109 |
| Inhibitory peptide 69 | J398E01 | 36.9 | 0.053 | 1.969 | G | G | I | E | C | Y | P | G | F | W | A | L | D | C | L | Y | 110 |
| Inhibitory peptide 70 | J398E07 | 28.3 | 0.057 | 1.617 | G | G | V | T | C | S | L | G | N | V | F | Y | L | C | H | D | 111 |
| Inhibitory peptide 71 | J398E08 | 29.7 | 0.060 | 1.778 | G | G | Q | L | C | P | E | G | Y | Y | A | L | M | C | T | D | 112 |
| Inhibitory peptide 72 | J398E10 | 29.2 | 0.054 | 1.585 | G | G | L | T | C | S | S | Q | N | I | Y | Y | L | C | S | D | 113 |
| Inhibitory peptide 73 | J398E12 | 31.1 | 0.054 | 1.672 | G | G | I | V | C | S | V | G | L | I | Y | F | L | C | A | D | 114 |

FIG. 22A

| | | | | | | | | | | | | | | | | | | | | | |
|---|---|---|---|---|---|---|---|---|---|---|---|---|---|---|---|---|---|---|---|---|---|
| Inhibitory peptide 74 | J398F04 | 16.4 | 0.104 | 1.700 | G | G | F | H | C | G | G | L | V | Y | S | L | D | C | S | Y | 115 |
| Inhibitory peptide 74 | J448A03 | 32.0 | 0.061 | 1.953 | G | G | F | H | C | G | G | L | V | Y | S | L | D | C | S | Y | 116 |
| Inhibitory peptide 75 | J398G04 | 17.9 | 0.094 | 1.689 | G | G | V | H | C | G | D | N | I | W | S | L | H | C | F | L | 117 |
| Inhibitory peptide 76 | J398H12 | 22.4 | 0.057 | 1.277 | G | G | L | M | C | Y | L | D | G | N | S | S | I | C | V | S | 118 |
| Inhibitory peptide 77 | J399D01 | 28.4 | 0.058 | 1.649 | G | G | P | C | R | D | L | F | S | E | V | L | Y | P | C | L | 119 |
| Inhibitory peptide 78 | J403C06 | 15.5 | 0.060 | 0.922 | G | G | Y | C | W | L | D | Y | S | I | L | S | Q | D | C | I | 120 |
| Inhibitory peptide 79 | J406H01 | 43.5 | 0.055 | 2.372 | G | G | P | F | C | V | D | A | S | A | D | R | A | C | F | W | 121 |
| Inhibitory peptide 80 | J399B12 | 25.3 | 0.060 | 1.525 | G | G | P | C | D | N | I | Y | Y | K | Y | F | Y | T | C | L | 122 |
| Inhibitory peptide 81 | J399E02 | 32.3 | 0.060 | 1.932 | G | G | T | C | Y | S | E | D | G | A | Y | Y | Y | L | C | M | 123 |
| Inhibitory peptide 82 | J402C07 | 33.0 | 0.056 | 1.837 | G | G | D | T | C | V | H | N | G | V | Y | F | L | C | V | D | 124 |
| Inhibitory peptide 83 | J402D02 | 22.9 | 0.056 | 1.274 | G | G | L | V | C | N | M | G | E | M | Y | F | L | C | D | V | 125 |
| Inhibitory peptide 84 | J404C03 | 30.1 | 0.072 | 2.153 | G | G | L | T | C | N | R | D | N | V | F | Y | L | C | V | D | 126 |
| Inhibitory peptide 85 | J406B03 | 26.4 | 0.052 | 1.375 | G | G | S | L | C | S | D | G | Y | W | S | L | N | C | E | F | 127 |

FIG. 22B

| Inhibitory Peptide ID | Peptide Amino Acid Sequence – Binding to HIV TCR | ELISA | | Inhibitory Peptide + GGGGS Linker SEQ ID NO: |
| | | EC50 | IC50 | |
| | | uM | uM | |
| Inhibitory peptide 57 (SEQ ID NO: 98) | GGSNCYSLEPWIYCDTGGGGS[PEG4]Lys(biotin)-NH2 | 0.50 | | 128 |
| Inhibitory peptide 58 (SEQ ID NO: 99) | GGLVCNDGNIWWLCEDGGGGS[PEG4]Lys(biotin)-NH2 | 0.88 | | 129 |
| Inhibitory peptide 59 (SEQ ID NO: 100) | GGFTCVDGQVYYLCDSGGGGS[PEG4]Lys(biotin)-NH2 | 0.69 | | 130 |
| Inhibitory peptide 60 (SEQ ID NO: 101) | GGGTCFHGNTYFLCEDGGGGS[PEG4]Lys(biotin)-NH2 | 0.29 | | 131 |
| Inhibitory peptide 61 (SEQ ID NO: 102) | GGQTCIADNVYYLCPEGGGGS[PEG4]Lys(biotin)-NH2 | 0.82 | | 132 |
| Inhibitory peptide 62 (SEQ ID NO: 103) | GGMLCNEGYWALSCFLGGGGS[PEG4]Lys(biotin)-NH2 | 0.69 | | 133 |
| Inhibitory peptide 63 (SEQ ID NO: 104) | GGVICTADGVYWLCDLGGGGS[PEG4]Lys(biotin)-NH2 | 1.29 | | 134 |
| Inhibitory peptide 64 (SEQ ID NO: 105) | GGVTCNDGKIFYLCSDGGGGS[PEG4]Lys(biotin)-NH2 | 0.63 | | 135 |
| Inhibitory peptide 65 (SEQ ID NO: 106) | GGAFCVDTKPGLVCFEGGGGS[PEG4]Lys(biotin)-NH2 | 0.26 | 112 | 136 |
| Inhibitory peptide 66 (SEQ ID NO: 107) | GGATCHLDNVYFLCDIGGGGS[PEG4]Lys(biotin)-NH2 | 0.34 | | 137 |
| Inhibitory peptide 67 (SEQ ID NO: 108) | GGTTCLEGGVYFLCADGGGGS[PEG4]Lys(biotin)-NH2 | 0.74 | | 138 |
| Inhibitory peptide 68 (SEQ ID NO: 109) | GGLVCNDGVVFWLCDSGGGGS[PEG4]Lys(biotin)-NH2 | 0.81 | | 139 |
| Inhibitory peptide 69 (SEQ ID NO: 110) | GGIECYPGFWALDCLYGGGGS[PEG4]Lys(biotin)-NH2 | 0.43 | | 140 |
| Inhibitory peptide 70 (SEQ ID NO: 111) | GGVTCSLGNVFYLCHDGGGGS[PEG4]Lys(biotin)-NH2 | 0.39 | | 141 |
| Inhibitory peptide 71 (SEQ ID NO: 112) | GGQLCPEGYYALMCTDGGGGS[PEG4]Lys(biotin)-NH2 | 0.15 | | 142 |
| Inhibitory peptide 72 (SEQ ID NO: 113) | GGLTCSSQNIYYLCSDGGGGS[PEG4]Lys(biotin)-NH2 | 0.40 | | 143 |

FIG. 24A

| Inhibitory peptide 73 (SEQ ID NO: 114) | GGIVCSVGLIYFLCADGGGGS[PEG4]Lys(biotin)-NH2 | 0.36 | | 144 |
|---|---|---|---|---|
| Inhibitory peptide 74 (SEQ ID NO: 116) | GGFHCGGLVYSLDCSYGGGGS[PEG4]Lys(biotin)-NH2 | 0.33 | | 145 |
| Inhibitory peptide 75 (SEQ ID NO: 117) | GGVHCGDNIWSLHCFLGGGGS[PEG4]Lys(biotin)-NH2 | 1.44 | | 146 |
| Inhibitory peptide 77 (SEQ ID NO: 119) | GGPCRDLFSEVLYPCLGGGGS[PEG4]Lys(biotin)-NH2 | 0.39 | | 147 |
| Inhibitory peptide 78 (SEQ ID NO: 120) | GGYCWLDYSILSQDCIGGGGS[PEG4]Lys(biotin)-NH2 | 5.00 | | 148 |
| Inhibitory peptide 79 (SEQ ID NO: 121) | GGPFCVDASADRACFWGGGGS[PEG4]Lys(biotin)-NH2 | 7.00 | | 149 |
| Inhibitory peptide 80 (SEQ ID NO: 122) | GGPCDNIYYKYFYTCLGGGGS[PEG4]Lys(biotin)-NH2 | 0.10 | | 150 |

FIG. 24B

INHIBITORY T CELL RECEPTOR PEPTIDES AND DISCOVERY METHODS

CROSS-REFERENCE

This application is a national stage entry of International Application No. PCT/US2019/044552, filed Jul. 31, 2019, which claims the benefit of U.S. Provisional Application No. 62/712,521 filed Jul. 31, 2018, each of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Dec. 16, 2019, is named 52426-708831_SL.txt and is 60,814 bytes in size.

SUMMARY OF THE DISCLOSURE

Disclosed herein, in certain embodiments, are methods of inhibiting an interaction of a T cell receptor (TCR) with a peptide-major histocompatibility (pMHC) complex, the method comprising administering to a TCR an inhibitory peptide that binds to the TCR without the aid of a MHC, thereby inhibiting the interaction of the TCR with a pMHC complex. In some embodiments, the inhibitory peptide is a peptide derived from a non-native antigen. In some embodiments, the inhibitory peptide is not identical to a peptide of peptide-major histocompatibility complex (pMHC). In some embodiments, the inhibitory peptide is from a peptide library. In some embodiments, the peptide library is a random peptide library. In some embodiments, the inhibitory peptide has at least 5 amino acids. In some embodiments, the inhibitory peptide has at least 8 amino acids. In some embodiments, the inhibitory peptide has at least 10 amino acids. In some embodiments, the inhibitory peptide has at least 12 amino acids. In some embodiments, the inhibitory peptide has at least 15 amino acids. In some embodiments, the inhibitory peptide has at least 18 amino acids. In some embodiments, the inhibitory peptide has no more than 30 amino acids. In some embodiments, the inhibitory peptide binds to the TCR through ionic interactions, electrostatic interactions, hydrophobic interactions, Pi-stacking interactions, and H-bonding interactions, or a combination thereof. In some embodiments, the binding of the inhibitory peptide to the TCR blocks the interaction of the TCR with a pMHC complex. In some embodiments, the inhibitory peptide is a linear or a cyclic peptide. In some embodiments, the inhibitory peptide comprises a modified amino acid, a non-natural amino acid, a modified non-natural amino acid, or combination thereof. In some embodiments, the modified amino acid or modified non-natural amino acid comprises a post-translational modification. In some embodiments, the inhibitory peptide binds to an alpha extracellular domain of the TCR. In some embodiments, the inhibitory peptide binds to a beta extracellular domain of the TCR. In some embodiments, the inhibitory peptide binds to an alpha extracellular domain of the TCR and a beta extracellular domain of the TCR. In some embodiments, the inhibitory peptide binds to a constant region of the alpha extracellular domain of the TCR. In some embodiments, the inhibitory peptide binds to a constant region of the beta extracellular domain of the TCR. In some embodiments, the inhibitory peptide binds to a variable region of the alpha extracellular domain of the TCR. In some embodiments, the inhibitory peptide binds to a variable region of the beta extracellular domain of the TCR. In some embodiments, the inhibitory peptide binds to a variable region of the alpha extracellular domain of the TCR and a variable region of the beta extracellular domain of the TCR. In some embodiments, the inhibitory peptide binds to the TCR at or near a complementarity-determining region (CDR) of the TCR. In some embodiments, the inhibitory peptide binds to the TCR at or near a CDR1 of the TCR. In some embodiments, the inhibitory peptide binds to the TCR at or near a CDR2 of the TCR. In some embodiments, the inhibitory peptide binds to the TCR at or near a CDR3 of the TCR. In some embodiments, the inhibitory peptide binds to the TCR at or near a complementarity-determining region (CDR) of the variable region of the alpha extracellular domain of the TCR. In some embodiments, the inhibitory peptide binds to the TCR at or near a complementarity-determining region (CDR) of the variable region of the beta extracellular domain of the TCR. In some embodiments, the inhibitory peptide binds to the TCR at or near a complementarity-determining region (CDR) of the variable region of the alpha extracellular domain of the TCR and the variable region of the beta extracellular domain of the TCR. In some embodiments, the TCR is expressed on a surface of the T cell. In some embodiments, the TCR is a soluble TCR. In some embodiments, the TCR is an engineered TCR. In some embodiments, the TCR comprises a TCR alpha extracellular domain comprising a variable region of the alpha extracellular domain of the TCR and a TCR beta extracellular domain comprising a variable region of the beta extracellular domain of the TCR. In some embodiments, the TCR alpha extracellular domain comprises a mutation to increase binding affinity of the TCR to the inhibitory peptide. In some embodiments, the TCR alpha extracellular domain comprises a mutation to increase stability of the TCR. In some embodiments, the TCR beta extracellular domain comprises a mutation to increase binding affinity of the TCR to the inhibitory peptide. In some embodiments, the TCR beta extracellular domain comprises a mutation to increase stability of the TCR. In some embodiments, the TCR alpha extracellular domain comprises a mutation to increase binding affinity of the TCR to the pMHC complex. In some embodiments, the TCR beta extracellular domain comprises a mutation to increase binding affinity of the TCR to the pMHC complex. In some embodiments, the TCR is a Mage-A3 TCR. In some embodiments, the Mage-A3 TCR comprises an alpha domain comprising an amino acid sequence of SEQ ID NO: 3. In some embodiments, the Mage-A3 TCR comprises a beta domain comprising an amino acid sequence of SEQ ID NO: 4. In some embodiments, the inhibitory peptide is Inhibitory peptide 2 (SEQ ID NO: 11), Inhibitory peptide 3 (SEQ ID NO: 12), Inhibitory peptide 1 (SEQ ID NO: 15), Inhibitory peptide 6 (SEQ ID NO: 16), Inhibitory peptide 7 (SEQ ID NO: 17), Inhibitory peptide 9 (SEQ ID NO: 19), Inhibitory peptide 12 (SEQ ID NO: 22), Inhibitory peptide 13 (SEQ ID NO: 23), Inhibitory peptide 15 (SEQ ID NO: 25), or Inhibitory peptide 25 (SEQ ID NO: 1). In some embodiments, the inhibitory peptide is Inhibitory peptide 1. In some embodiments, the inhibitory peptide comprises the amino acid sequence of VSCKDVYDEAFCW (SEQ ID NO: 2). In some embodiments, the TCR with a bound inhibitory peptide comprises an amino acid sequence of SEQ ID NO: 5. In some embodiments, the TCR with a bound inhibitory peptide comprises an amino acid sequence of SEQ ID NO: 6. In some embodiments, the inhibitory peptide binds to the TCR at or near a CDR of the variable region of the alpha extracellular domain of the TCR at at least one amino acid residue at position according to SEQ ID NO: 3 selected from the list consisting of 32, 94, and 102. In some embodiments, the inhibitory peptide binds to the TCR at or near a CDR of the variable region of the alpha extracellular domain of the TCR at at least one amino acid residue according to SEQ ID NO: 3 selected from the list consisting of TYR32, ARG94, and PHE102. In some embodiments, the inhibitory peptide binds to the TCR at or near a CDR1, CDR2, and CDR3 of the variable region of the beta extracellular domain of the TCR. In some embodiments, the inhibitory peptide binds to the TCR at or near a CDR of the variable region of the beta extracellular domain of the TCR at at least one amino acid residue at position according to SEQ ID NO: 4 selected from the list consisting of 31, 49, 51, 56, and 98. In some embodiments, the inhibitory peptide binds to the TCR at or near a CDR of the variable region of the beta extracellular domain of the TCR at at least one amino acid residue according to SEQ ID NO: 4 selected from the list consisting of ARG31, GLU49, PHE51, ARG56, and MET98. In some embodiments, the TCR is a gp100 TCR. In some embodiments, the gp100 TCR comprises an alpha domain comprising an amino acid sequence of SEQ ID NO: 7. In some embodiments, the gp100 TCR comprises a beta domain comprising an amino acid sequence of SEQ ID NO: 8. In some embodiments, the inhibitory peptide is Inhibitory peptide 29 (SEQ ID NO: 61), Inhibitory peptide 30 (SEQ ID NO: 62), Inhibitory peptide 31 (SEQ ID NO: 63), Inhibitory peptide 35 (SEQ ID NO: 67), or Inhibitory peptide 37 (SEQ ID NO: 69). In some embodiments, the TCR is a HIV TCR. In some embodiments, the HIV TCR comprises an alpha domain comprising an amino acid sequence of SEQ ID NO: 9. In some embodiments, the HIV TCR comprises a beta domain comprising an amino acid sequence of SEQ ID NO: 10. In some embodiments, the inhibitory peptide is Inhibitory peptide 65 (SEQ ID NO: 106).

Disclosed herein, in certain embodiments, are methods of identifying a peptide that binds to a T cell receptor (TCR) without the aid of a MHC, the method comprising: (a) incubating a peptide from a peptide library and a TCR in a suitable medium at a neutral pH, wherein the peptide from the peptide library is expressed on a surface of a cell or a phage; (b) removing non-binding peptides by washing the medium at a neutral pH; (c) eluting the peptide that is bound to the TCR by altering the pH to an acidic pH, or a basic pH; and (d) identifying the peptide that is bound to the TCR without the aid of a MHC by sequencing DNA of the cell or the phage on which the peptide is expressed. In some embodiments, the neutral pH is from 7.0 to 7.8. In some embodiments, the neutral pH is 7.4. In some embodiments, the acidic pH is from 2.0 to 5.0. In some embodiments, the acidic pH is 2.2. In some embodiments, the basic pH is from 9.0 to 11.5. In some embodiments, the basic pH is 11.0. In some embodiments, steps (a)-(c) are repeated at least one time prior to step (d). In some embodiments, steps (a)-(c) are repeated at least two times prior to step (d). In some embodiments, steps (a)-(c) are repeated at least three times prior to step (d). In some embodiments, the peptide library is a phagemid peptide library. In some embodiments, the peptide of step (a) is expressed on a surface of an E. coli cell. In some embodiments, the peptide of step (a) is expressed on a surface of a yeast cell. In some embodiments, the peptide of step (a) is expressed on a surface of a phage. In some embodiments, the peptide is derived from a non-native antigen. In some embodiments, the peptide is not identical to a peptide of a peptide-major histocompatibility complex (pMHC). In some embodiments, the peptide library is a random peptide library. In some embodiments, the peptide has at least 5 amino acids. In some embodiments, the peptide has at least 8 amino acids. In some embodiments, the peptide has at least 10 amino acids. In some embodiments, the peptide has at least 12 amino acids. In some embodiments, the peptide has at least 15 amino acids. In some embodiments, the peptide has at least 18 amino acids. In some embodiments, the peptide has no more than 30 amino acids. In some embodiments, the peptide binds to the TCR through ionic interactions, electrostatic interactions, hydrophobic interactions, Pi-stacking interactions, and H-bonding interactions, or a combination thereof. In some embodiments, the peptide is a linear or a cyclic peptide. In some embodiments, the peptide comprises a modified amino acid, a non-natural amino acid, a modified non-natural amino acid, or combination thereof. In some embodiments, the modified amino acid or modified non-natural amino acid comprises a post-translational modification. In some embodiments, the inhibitory peptide binds to an alpha extracellular domain of the TCR. In some embodiments, the inhibitory peptide binds to a beta extracellular domain of the TCR. In some embodiments, the inhibitory peptide binds to an alpha extracellular domain of the TCR and a beta extracellular domain of the TCR. In some embodiments, the inhibitory peptide binds to a constant region of the alpha extracellular domain of the TCR. In some embodiments, the inhibitory peptide binds to a constant region of the beta extracellular domain of the TCR. In some embodiments, the inhibitory peptide binds to a variable region of the alpha extracellular domain of the TCR. In some embodiments, the inhibitory peptide binds to a variable region of the beta extracellular domain of the TCR. In some embodiments, the inhibitory peptide binds to a variable region of the alpha extracellular domain of the TCR and a variable region of the beta extracellular domain of the TCR. In some embodiments, the inhibitory peptide binds to the TCR at or near a complementarity-determining region (CDR) of the TCR. In some embodiments, the inhibitory peptide binds to the TCR at or near a CDR1 of the TCR. In some embodiments, the inhibitory peptide binds to the TCR at or near a CDR2 of the TCR. In some embodiments, the inhibitory peptide binds to the TCR at or near a CDR3 of the TCR. In some embodiments, the inhibitory peptide binds to the TCR at or near a complementarity-determining region (CDR) of the variable region of the alpha extracellular domain of the TCR. In some embodiments, the inhibitory peptide binds to the TCR at or near a complementarity-determining region (CDR) of the variable region of the beta extracellular domain of the TCR. In some embodiments, the inhibitory peptide binds to the TCR at or near a complementarity-determining region (CDR) of the variable region of the alpha extracellular domain of the TCR and the variable region of the beta extracellular domain of the TCR.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A illustrates the Mage-A3 sTCR exists as a heterodimer comprising a β-chain and an α-chain. FIG. 2B illustrates a size exclusion-high-performance liquid chromatography (SEC-HPLC) chromatogram of the Mage-A3 sTCR. FIG. 2C illustrates a liquid chromatograph-mass spectrometry (LC/MS) chromatogram of the Mage-A3 sTCR. FIG. 2D illustrates a bio-layer interferometry (BLI) sensorgram of binding between the Mage-A3 sTCR and the Mage-A3 peptide-major histocompatibility complex (pMHC) at four different concentrations of the Mage-A3 sTCR: 50 nM, 25 nM, 12.5 nM, and 6.25 nM. For each concentration, a pair of lines is shown representing the raw data as well as a curve fit for rate constant calculations. FIG. 2E shows the equilibrium dissociation constant (Kd), association rate constant ($k_{on}$), and dissociation rate constant ($k_{dis}$) of binding between Mage-A3 sTCR and Mage-A3 pMHC.

FIG. 3A is an exemplary phagemid competition ELISA from a collection of enriched clones isolated after three rounds of biopanning against soluble Mage-A3 TCR or a control (NeutrAvidin). FIG. 3B is an exemplary phagemid competition ELISA from a collect of enriched clones isolated after three rounds of biopanning against Mage-A3 TCR or a control (NeutrAvidin). FIG. 3C illustrates an anti-pMHC competition ELISA of select phage clones.

FIG. 4A is an exemplary bio-layer interferometry (BLI) sensorgram of binding between inhibitory peptide 1 (SEQ ID NO: 15), immobilized at 100 nM, and soluble Mage-A3 sTCR at seven different concentrations: 100 nM, 50 nM, 25 nM, 12.5 nM, 6.25 nM, 3.125 nM, and 1.5625 nM. FIG. 4B shows the equilibrium dissociation constant (Kd), association rate constant ($k_{on}$), and dissociation rate constant ($k_{dis}$) of binding between inhibitory peptide 1 and Mage-A3 sTCR.

FIG. 7A-FIG. 7B provide a summary of phagemid ELISA MAGE-A3 specificity binding and MAGE-A3 pMHC inhibitory ELISA results.

FIG. 10A-FIG. 10B provide a summary of phagemid ELISA MAGE-A3 binding and MAGE-A3 pMHC inhibitory ELISA results.

FIG. 11A illustrates the masked anti-MAGE-A3 sTCR exists as a heterodimer comprising a β-chain and an α-chain by non-reducing and reducing SDS-PAGE analysis. FIG. 11B illustrates a size exclusion-high-performance liquid chromatography (SEC-HPLC) chromatogram of the masked anti-MAGE-A3 sTCR FIG. 11C illustrates a liquid chromatograph-mass spectrometry (LC/MS) chromatogram of the masked anti-MAGE-A3 sTCR FIG. 12A illustrates the masked anti-MAGE-A3 sTCR exists as a heterodimer comprising a β-chain and an α-chain by non-reducing and reducing SDS-PAGE analysis. FIG. 12B illustrates a size exclusion-high-performance liquid chromatography (SEC-HPLC) chromatogram of the masked anti-MAGE-A3 sTCR FIG. 12C illustrates a liquid chromatograph-mass spectrometry (LC/MS) chromatogram of the masked anti-MAGE-A3 sTCR

FIG. 15A displays and designates specific residues interacting between Inhibitory peptide 1 and the MAGE-A3 alpha subunit. FIG. 15B displays and designates specific residues interacting between Inhibitory peptide 1 and the MAGE-A3 beta subunit.

FIG. 16A-FIG. 16E illustrate analytical and functional characterization of a functional gp100 soluble TCR FIG. 16A illustrates the gp100 sTCR exists as a heterodimer comprising a β-chain and an α-chain by non-reducing and reducing SDS-PAGE analysis. FIG. 16B illustrates a size exclusion-high-performance liquid chromatography (SEC-HPLC) chromatogram of the gp100 sTCR FIG. 16C illustrates a liquid chromatograph-mass spectrometry (LC/MS) chromatogram of the gp100 sTCR FIG. 16D illustrates a bio-layer interferometry (BLI) sensorgram of binding between the gp100 sTCR and the gp100 peptide-major histocompatibility complex (pMHC) at different concentrations of the gp100 sTCR: 100 nM, 50 nM, 25 nM, 12.5 nM, 6.25 nM, 3.13 nM, 1.63 nM, and 0 nM. For each concentration, a pair of lines is shown representing the raw data as well as a curve fit for rate constant calculations. FIG. 16E shows the equilibrium dissociation constant (Kd), association rate constant (kon), and dissociation rate constant (koff) of binding between gp100 sTCR and gp100 pMHC.

FIG. 17A-17B are a summary of phagemid ELISA specificity binding to gp100 TCR and respective sequence identity.

FIG. 20 is summary of synthetic inhibitory peptide screening against gp100 TCR

FIG. 21A illustrates the HIV sTCR exists as a heterodimer comprising a 0-chain and an α-chain by non-reducing and reducing SDS-PAGE analysis. FIG. 21B illustrates a bio-layer interferometry (BLI) sensorgram of binding between the HIV sTCR and the HIV peptide-major histocompatibility complex (pMHC) at different concentrations of the HIV sTCR: 50 nM, 25 nM, 12.5 nM, 6.25 nM, 3.13 nM, and 0 nM. For each concentration, a pair of lines is shown representing the raw data as well as a curve fit for rate constant calculations. FIG. 21C shows the equilibrium dissociation constant (Kd), association rate constant (kon), and dissociation rate constant (koff) of binding between HIV sTCR and HIV pMHC.

FIG. 22A-FIG. 22B are a summary of phagemid ELISA specificity binding to HIV and respective sequence identity.

FIG. 23A illustrates by ELISA binding HIV TCR binding to synthetic peptides. FIG. 23B illustrates by ELISA synthetic peptide HIV pMHC competition of HIV TCR binding.

FIG. 24A-FIG. 24B depict quantitative summary of synthetic inhibitory peptide binding and pMHC competition against HIV TCR

DETAILED DESCRIPTION

Figure 1:
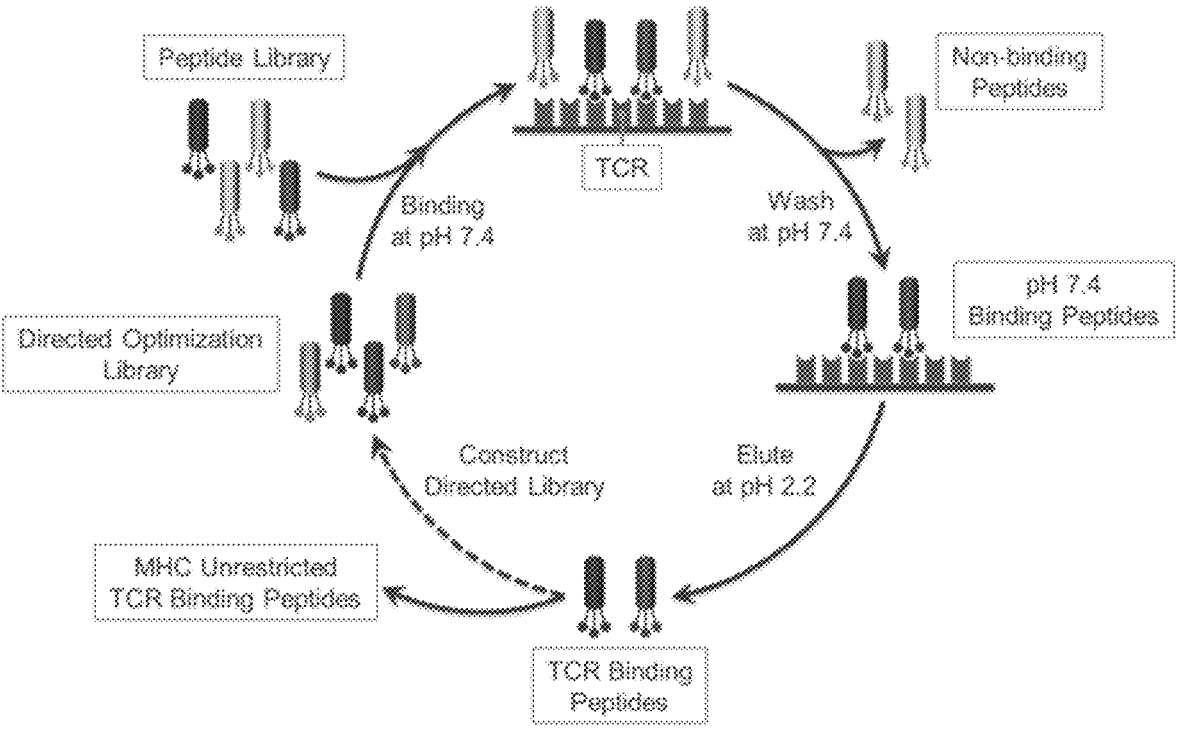
FIG. 1 is an exemplary schematic of phage peptide panning to identify TCR binding peptide candidates.

The ability of T cells to distinguish between self and non-self depends on the ability of the T cell receptor (TCR) to recognize fragments of antigens or peptides, when these peptides are presented to the TCR as a peptide-major histocompatibility complex (pMHC) molecules. The TCRs were thought to bind to a peptide only when the peptide was in a complex with a MHC. Disclosed herein, in some embodiments, are methods of inhibiting an interaction of a TCR with a peptide-major histocompatibility (pMHC) complex, the method comprising administering to a TCR an inhibitory peptide that binds to the TCR without the aid of a MHC. Further disclosed herein, in some embodiments, are methods of identifying peptides that bind to a TCR without the aid of a MHC.

Certain Definitions

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value.

"Transmembrane domain", as used herein, refers to the region of a receptor which crosses the plasma membrane. Examples include the transmembrane region of a transmembrane protein (for example a Type 1 transmembrane protein), an artificial hydrophobic sequence, and a combination thereof.

"Fragment" as used herein refers to a peptide or a polypeptide that comprises less than the full length amino acid sequence.

"Antigen-binding site" as used herein refers to the region of a polypeptide that interacts with an antigen. The antigen binding site includes amino acid residues that interact directly with an antigen and those amino acid residues that are within proximity to the antigen but that may not interact directly with the antigen.

"Target antigen" as used herein refers to a molecule that binds to a variable region of the TCR alpha extracellular domain or the variable region of the TCR beta extracellular domain or both.

T Cell Receptor (TCR)

Native TCRs are transmembrane receptors expressed on the surface of T cells that recognize antigens bound to major histocompatibility complex molecules (MHC). Native TCRs are heterodimeric, and comprise an alpha polypeptide chain and a beta polypeptide chain linked through a disulfide bond. The alpha polypeptide chain and the beta polypeptide chain are expressed as part of a complex with accessory proteins which include, for example, two CD3 epsilon polypeptides, one CD3 gamma polypeptide, one CD3 delta polypeptide, and two CD3 zeta polypeptides. When a TCR engages with a target antigen and MHC, the T cell is activated resulting in a series of signaling events mediated by associated enzymes, co-receptors, adapter molecules, and activated or released transcription factors.

In native TCRs, the alpha polypeptide chain and the beta polypeptide chain comprise an extracellular domain, a transmembrane domain, and a cytoplasmic domain. Each extracellular domain comprises a variable region (V), a joining region (J), and a constant region (C). The constant region is N-terminal to the transmembrane domain, and the transmembrane domain is N-terminal to the cytoplasmic domain. The variable regions of both the alpha polypeptide chain and the beta polypeptide chain comprise three hypervariable or complementarity determining regions (CDRs). The beta polypeptide chain usually contains a short diversity region between the variable and joining regions. The three CDRs are embedded into a framework sequence, with one CDR being the hypervariable region named CDR3. The alpha chain variable region (Vα) and the beta chain variable region (Vβ) are of several types that are distinguished by their framework sequences, CDR1 and CDR2 sequences, and a partly defined CDR3 sequence.

TCRs are described using the International Immunogenetics (IMGT) TCR nomenclature. The Vα in IMGT nomenclature is referred to by a unique "TRAV" number. In the same way, Vβ is referred to by a unique "TRBV" number. The corresponding joining and constant regions are referred to as TRAJ and TRAC, respectively for the α joining and constant regions, and TRBJ and TRBC, respectively for the β joining and constant regions. The sequences defined by the IMGT nomenclature are known in the art, and are contained within the online IMGT public database.

Methods of Inhibiting Interaction of a T Cell Receptor (TCR) with a Peptide-Major Histocompatibility Complex (pMHC)

Disclosed herein, in some embodiments, are methods of inhibiting an interaction of a T cell receptor (TCR) with a peptide-major histocompatibility (pMHC) complex, the method comprising administering to a TCR an inhibitory peptide that binds to the TCR without the aid of a MHC, thereby inhibiting the interaction of the TCR with a pMHC complex.

In some embodiments, the inhibitory peptide is a peptide derived from a non-native antigen.

In some embodiments, the inhibitory peptide is a non-human antigen. In some embodiments, the inhibitory peptide comprises a viral peptide sequence, bacterial peptide sequence, or a fungal peptide sequence.

In some embodiments, the inhibitory peptide is from a peptide library. In some embodiments, the peptide library is a phagemid peptide library. In some embodiments, the peptide from the peptide library is expressed on a surface of an *E. coli* cell. In some embodiments, the peptide from the peptide library is expressed on a surface of a yeast cell. In some embodiments, the peptide from the peptide library is expressed on a surface of a phage. In some embodiments, the peptide library comprises linear peptides. In some embodiments, the peptide library comprises cyclic peptides. In some embodiments, the peptide library is a random peptide library. In some embodiments, the random peptide library is randomized to contain all 20 amino acid residues at each position in the peptide library. In some embodiments, the random peptide library comprises a discrete subset of the 20 possible amino acids at each position in the peptide library. In some embodiments, the random peptide library comprises a single amino acid at one or more discrete positions within the peptide library. In some embodiments, the peptide libraries fix pairs of positions within the peptide library with cysteine residues for the production of disulfide linked cyclic peptide libraries. In some embodiments, the fixed pairs of cysteines are positioned such that the intervening peptide sequences are varied in length between 4 amino acids and 18 amino acids.

In some embodiments, the cyclic peptide library comprises randomized amino acids that flank the ring structure at the amino terminal, carboxyl terminal or both between 1 amino acid and 8 amino acids.

In some embodiments, the inhibitory peptide is not identical to a peptide of pMHC complex. In some embodiments, the inhibitory peptide contains no or substantially no homology to a peptide of pMHC complex. In some embodiments, the inhibitory peptide contains at least 5%, 10%, 15%, 20%, 25%, 30%, 35%, 40%, 45%, 50%, 55%, 60%, 65%, 70%, 75%, or 80% sequence identity to a peptide of pMHC complex. In some embodiments, the inhibitory peptide contains at least 5%, 10%, 15%, 20%, 25%, 30%, 35%, 40%, 45%, 50%, 55%, 60%, 65%, 70%, 75%, or 80% sequence identity to the target antigen.

In some embodiments, the inhibitory peptide comprises a peptide sequence of at least 5 amino acids in length. In some embodiments, the inhibitory peptide comprises a peptide sequence of at least 6 amino acids in length. In some embodiments, the inhibitory peptide comprises a peptide sequence of at least 7 amino acids in length. In some embodiments, the inhibitory peptide comprises a peptide sequence of at least 8 amino acids in length. In some embodiments, the inhibitory peptide comprises a peptide sequence of at least 9 amino acids in length. In some embodiments, the inhibitory peptide comprises a peptide sequence of at least 10 amino acids in length. In some embodiments, the inhibitory peptide comprises a peptide sequence of at least 11 amino acids in length. In some embodiments, the inhibitory peptide comprises a peptide sequence of at least 12 amino acids in length. In some embodiments, the inhibitory peptide comprises a peptide sequence of at least 13 amino acids in length. In some embodiments, the inhibitory peptide comprises a peptide sequence of at least 14 amino acids in length. In some embodiments, the inhibitory peptide comprises a peptide sequence of at least 15 amino acids in length. In some embodiments, the inhibitory peptide comprises a peptide sequence of at least 16 amino acids in length. In some embodiments, the inhibitory peptide comprises a peptide sequence of at least 17 amino acids in length. In some embodiments, the inhibitory peptide comprises a peptide sequence of at least 18 amino acids in length. In some embodiments, the inhibitory peptide comprises a peptide sequence of at least 19 amino acids in length. In some embodiments, the inhibitory peptide comprises a peptide sequence of at least 20 amino acids in length. In some embodiments, the inhibitory peptide comprises a peptide sequence of at least 25 amino acids in length. In some embodiments, the inhibitory peptide comprises a peptide sequence of no more than 30 amino acids in length. In some embodiments, the inhibitory peptide comprises a peptide sequence of at least 10 to 30 amino acids in length. In some embodiments, the inhibitory peptide is a linear peptide. In some embodiments, the inhibitory peptide is a cyclic peptide.

In some embodiments, the inhibitory peptide comprises a modified amino acid, a non-natural amino acid, a modified non-natural amino acid, or combination thereof. In some embodiments, the modified amino acid or modified non-natural amino acid comprises a post-translational modification. In some embodiments, the modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Modification are made anywhere on the inhibitory peptide including the peptide backbone, or the amino acid side chains. In some embodiments, the inhibitory peptide comprises an alkyne or dibenzocyclooctyne modified amino acid for reacting with an azide functionalized molecule. In some embodiments, the inhibitory peptide comprises a trans-cyclooctene, vinyl, or methylcyclopropene modified amino acid for reacting with a tetrazine functionalized molecule.

In some embodiments, the inhibitory peptide binds to the TCR through ionic interactions, electrostatic interactions, hydrophobic interactions, Pi-stacking interactions, and H-bonding interactions, or a combination thereof.

In some embodiments, the binding of the inhibitory peptide to the TCR conceals, sterically blocks, or inhibits the antigen binding site of TCR from interacting with a pMHC complex. In some embodiments, the binding of the inhibitory peptide to the TCR sterically blocks the interaction of the TCR with a pMHC complex. In some embodiments, the binding of the inhibitory peptide to the TCR conceals, blocks, or inhibits the antigen binding site of TCR from interacting with a pMHC complex. In some embodiments, the binding of the inhibitory peptide to the TCR blocks the interaction of the TCR with a pMHC complex.

In some embodiments, the inhibitory peptide binds to the TCR alpha extracellular domain, to the TCR beta extracellular domain, or both to conceal, sterically block, or inhibit the antigen binding site of the TCR from interacting with a pMHC complex. In some embodiments, the inhibitory peptide binds to the TCR alpha extracellular domain, to the TCR beta extracellular domain, or both to conceal, block, or inhibit the antigen binding site of the TCR from interacting with a pMHC complex. In some embodiments, the inhibitory peptide binds to a constant region of the alpha extracellular domain of the TCR, or to the constant region of the beta extracellular domain of the TCR. In some embodiments, the inhibitory peptide binds to a variable region of the alpha extracellular domain of the TCR, a variable region of the beta extracellular domain of the TCR, or both. In some embodiments, the inhibitory peptide binds to the TCR at or near a CDR of the TCR. In some embodiments, the inhibitory peptide binds to the TCR at or near a CDR1 of the TCR. In some embodiments, the inhibitory peptide binds to the TCR at or near a CDR2 of the TCR. In some embodiments, the inhibitory peptide binds to the TCR at or near a CDR3 of the TCR. In some embodiments, the inhibitory peptide binds to the TCR at or near a CDR1 and a CDR2 of the TCR. In some embodiments, the inhibitory peptide binds to the TCR at or near a CDR1 and a CDR3 of the TCR. In some embodiments, the inhibitory peptide binds to the TCR at or near a CDR2 and a CDR3 of the TCR. In some embodiments, the inhibitory peptide binds to the TCR at or near a CDR1, a CDR2, and a CDR3 of the TCR. In some embodiments, the inhibitory peptide binds to the TCR at or near a complementarity-determining region (CDR) of the variable region of the alpha extracellular domain of the TCR, to the TCR at or near a complementarity-determining region (CDR) of the variable region of the beta extracellular domain of the TCR, or both.

In some embodiments, the TCR is expressed on a surface of the T cell. In some embodiments, the TCR comprises a TCR alpha extracellular domain, and a transmembrane domain, and a TCR beta extracellular domain, and a transmembrane domain. In some embodiments, the TCR alpha extracellular domain comprises a variable region. In some embodiments, the TCR alpha extracellular domain comprises a variable region, a joining region, and a constant region. In some embodiments, the TCR alpha extracellular domain is a full length TCR alpha extracellular domain. In some embodiments, the TCR alpha extracellular domain comprises three hyper-variable complementarity determining regions (CDRs) within the variable region. In some embodiments, the TCR beta extracellular domain comprises a variable region. In some embodiments, the TCR beta extracellular domain comprises a variable region, a joining region, and a constant region. In some embodiments, the TCR beta extracellular domain is a full length TCR beta extracellular domain. In some embodiments, the TCR beta extracellular domain comprises three hyper-variable complementarity determining regions (CDRs).

In some embodiments, the TCR is a soluble TCR. In some embodiments, the TCR comprises a TCR alpha extracellular domain, and a TCR beta extracellular domain. In some embodiments, the TCR alpha extracellular domain comprises a variable region. In some embodiments, the TCR alpha extracellular domain comprises a variable region, a joining region, and a constant region. In some embodiments, the TCR alpha extracellular domain is a full length TCR alpha extracellular domain. In some embodiments, the TCR alpha extracellular domain comprises three hyper-variable complementarity determining regions (CDRs) within the variable region. In some embodiments, the TCR alpha extracellular domain further comprises a truncated transmembrane domain. In some embodiments, the TCR alpha extracellular domain lacks a transmembrane domain. In some embodiments, the TCR beta extracellular domain comprises a variable region. In some embodiments, the TCR beta extracellular domain comprises a variable region, a joining region, and a constant region. In some embodiments, the TCR beta extracellular domain is a full length TCR beta extracellular domain. In some embodiments, the TCR beta extracellular domain comprises three hyper-variable complementarity determining regions (CDRs). In some embodiments, the TCR beta extracellular domain further comprises a truncated transmembrane domain. In some embodiments, the TCR beta extracellular domain lacks a transmembrane domain.

In some embodiments, the TCR is an engineered TCR. In some embodiments, the engineered TCR is modified to increase binding affinity of the TCR to the inhibitory peptide. In some embodiments, the engineered TCR is modified to increase stability of the TCR. In some embodiments, the engineered TCR is modified to increase binding affinity of the TCR to the pMHC complex. In some embodiments, the engineered TCR is modified to decrease aggregation.

In some embodiments, the TCR alpha extracellular domain comprises a mutation to increase binding affinity of the TCR to the inhibitory peptide. In some embodiments, the TCR alpha extracellular domain comprises a mutation to increase stability of the TCR. In some embodiments, the TCR beta extracellular domain comprises a mutation to increase binding affinity of the TCR to the inhibitory peptide. In some embodiments, the TCR beta extracellular domain comprises a mutation to increase stability of the TCR. In some embodiments, the TCR alpha extracellular domain and the TCR beta extracellular domain comprises a mutation to increase the binding affinity of the TCR to the inhibitory peptide. In some embodiments, the TCR alpha extracellular domain and the TCR beta extracellular domain comprises a mutation to increase stability of the TCR. In some embodiments, the TCR alpha extracellular domain comprises a mutation to increase binding affinity of the TCR to the inhibitory peptide and the TCR alpha extracellular domain of the TCR comprises a mutation to increase stability of the TCR. In some embodiments, the TCR beta extracellular domain comprises a mutation to increase binding affinity of the TCR to the inhibitory peptide and the TCR beta extracellular domain of the TCR comprises a mutation to increase stability of the TCR. In some embodiments, the TCR alpha extracellular domain of the TCR comprises a mutation to increase binding affinity of the TCR to the inhibitory peptide and the TCR beta extracellular domain of the TCR comprises a mutation to increase binding affinity of the TCR to the inhibitory peptide. In some embodiments, the TCR alpha extracellular domain of the TCR comprises a mutation to increase stability of the TCR and the TCR beta extracellular domain of the TCR comprises a mutation to increase stability of the TCR. In some embodiments, the TCR alpha extracellular domain of the TCR comprises a mutation to increase binding affinity of the TCR to the inhibitory peptide and the TCR beta extracellular domain of the TCR comprises a mutation to increase stability of the TCR. In some embodiments, the TCR alpha extracellular domain of the TCR comprises a mutation to increase stability of the TCR and the TCR beta extracellular domain of the TCR comprises a mutation to increase binding affinity of the TCR to the inhibitory peptide.

In some embodiments, the TCR alpha extracellular domain comprises a mutation to increase binding affinity of the TCR to the pMHC complex. In some embodiments, the TCR beta extracellular domain comprises a mutation to increase binding affinity of the TCR to the pMHC complex. In some embodiments, the TCR alpha extracellular domain and the TCR beta extracellular domain comprises a mutation to increase binding affinity of the TCR to the pMHC complex.

In some embodiments, the TCR includes, but is not limited to, a PRAME TCR, a MAGE-A1 TCR, a MAGE-4 TCR, a MAGE-A10 TCR, a NY-ESO-1 TCR, an alpha fetoprotein (AFP) TCR, a Mage-A3 TCR, a gp100 TCR, and an HIV TCR. In some embodiments, the TCR is a PRAME TCR. In some embodiments, the TCR is a MAGE-A1 TCR. In some embodiments, the TCR is a MAGE-4 TCR. In some embodiments, the TCR is a MAGE-A10 TCR. In some embodiments, the TCR is a NY-ESO-1 TCR. In some embodiments, the TCR is an alpha fetoprotein (AFP) TCR.

In some embodiments, the TCR is a Mage-A3 TCR. In some embodiments, the Mage-A3 TCR comprises an alpha domain comprising an amino acid sequence of SEQ ID NO: 3. In some embodiments, the Mage-A3 TCR comprises a beta domain comprising an amino acid sequence of SEQ ID NO: 4. In some embodiments, the inhibitory peptide is a peptide listed in FIGS. 7A-7B. In some embodiments, the inhibitory peptide is a peptide listed in FIGS. 10A-10B. In some embodiments, the inhibitory peptide is Inhibitory peptide 2 (SEQ ID NO: 11), Inhibitory peptide 3 (SEQ ID NO: 12), Inhibitory peptide 4 (SEQ ID NO: 13), Inhibitory peptide 5 (SEQ ID NO: 14), Inhibitory peptide 1 (SEQ ID NO: 15), Inhibitory peptide 6 (SEQ ID NO: 16), Inhibitory peptide 7 (SEQ ID NO: 17), Inhibitory peptide 8 (SEQ ID NO: 18), Inhibitory peptide 9 (SEQ ID NO: 19), Inhibitory peptide 10 (SEQ ID NO: 20), Inhibitory peptide 11 (SEQ ID NO: 21), Inhibitory peptide 12 (SEQ ID NO: 22), Inhibitory peptide 13 (SEQ ID NO: 23), Inhibitory peptide 14 (SEQ ID NO: 24), Inhibitory peptide 15 (SEQ ID NO: 25), Inhibitory peptide 16 (SEQ ID NO: 26), Inhibitory peptide 17 (SEQ ID NO: 27), Inhibitory peptide 18 (SEQ ID NO: 28), Inhibitory peptide 19 (SEQ ID NO: 29), Inhibitory peptide 20 (SEQ ID NO: 30), Inhibitory peptide 25 (SEQ ID NO: 1), or Inhibitory peptide 26 (SEQ ID NO: 58). In some embodiments, the inhibitory peptide is Inhibitory peptide 2 (SEQ ID NO: 11), Inhibitory peptide 3 (SEQ ID NO: 12), Inhibitory peptide 1 (SEQ ID NO: 15), Inhibitory peptide 6 (SEQ ID NO: 16), Inhibitory peptide 7 (SEQ ID NO: 17), Inhibitory peptide 9 (SEQ ID NO: 19), Inhibitory peptide 12 (SEQ ID NO: 22), Inhibitory peptide 13 (SEQ ID NO: 23), Inhibitory peptide 15 (SEQ ID NO: 25), or Inhibitory peptide 25 (SEQ ID NO: 1). In some embodiments, the inhibitory peptide is Inhibitory peptide 2 (SEQ ID NO: 11). In some embodiments, the inhibitory peptide is Inhibitory peptide 3 (SEQ ID NO: 12). In some embodiments, the inhibitory peptide is Inhibitory peptide 4 (SEQ ID NO: 13). In some embodiments, the inhibitory peptide is Inhibitory peptide 5 (SEQ ID NO: 14). In some embodiments, the inhibitory peptide is Inhibitory peptide 1 (SEQ ID NO: 15). In some embodiments, the inhibitory peptide is Inhibitory peptide 6 (SEQ ID NO: 16). In some embodiments, the inhibitory peptide is Inhibitory peptide 7 (SEQ ID NO: 17). In some embodiments, the inhibitory peptide is Inhibitory peptide 8 (SEQ ID NO: 18). In some embodiments, the inhibitory peptide is Inhibitory peptide 9 (SEQ ID NO: 19). In some embodiments, the inhibitory peptide is Inhibitory peptide 10 (SEQ ID NO: 20). In some embodiments, the inhibitory peptide is Inhibitory peptide 11 (SEQ ID NO: 21). In some embodiments, the inhibitory peptide is Inhibitory peptide 12 (SEQ ID NO: 22). In some embodiments, the inhibitory peptide is Inhibitory peptide 13 (SEQ ID NO: 23). In some embodiments, the inhibitory peptide is Inhibitory peptide 14 (SEQ ID NO: 24). In some embodiments, the inhibitory peptide is Inhibitory peptide 15 (SEQ ID NO: 25). In some embodiments, the inhibitory peptide is Inhibitory peptide 16 (SEQ ID NO: 26). In some embodiments, the inhibitory peptide is Inhibitory peptide 17 (SEQ ID NO: 27). In some embodiments, the inhibitory peptide is Inhibitory peptide 18 (SEQ ID NO: 28). In some embodiments, the inhibitory peptide is Inhibitory peptide 19 (SEQ ID NO: 29). In some embodiments, the inhibitory peptide is Inhibitory peptide 20 (SEQ ID NO: 30). In some embodiments, the inhibitory peptide is Inhibitory peptide 25 (SEQ ID NO: 1). In some embodiments, the inhibitory peptide is Inhibitory peptide 26 (SEQ ID NO: 58). In some embodiments, the inhibitory peptide comprises the amino acid sequence of VSCKDVYDEAFCW (SEQ ID NO: 2). In some embodiments, the inhibitory peptide comprising the amino acid sequence of VSCKDVYDEAFCW (SEQ ID NO: 2) binds to a Mage-A3 TCR. In some embodiments, the TCR with a bound inhibitory peptide comprises an amino acid sequence of SEQ ID NO: 5. In some embodiments, the TCR with a bound inhibitory peptide comprises an amino acid sequence of SEQ ID NO: 6. In some embodiments, the inhibitory peptide binds to the TCR at or near a CDR of the variable region of the alpha extracellular domain of the TCR at at least one amino acid residue at position according to SEQ ID NO: 3 selected from the list consisting of 32, 94, and 102. In some embodiments, the inhibitory peptide binds to the TCR at or near a CDR of the variable region of the alpha extracellular domain of the TCR at at least one amino acid residue according to SEQ ID NO: 3 selected from the list consisting of TYR32, ARG94, and PHE102. In some embodiments, the inhibitory peptide binds to the TCR at or near a CDR1, CDR2, and CDR3 of the variable region of the beta extracellular domain of the TCR. In some embodiments, the inhibitory peptide binds to the TCR at or near a CDR of the variable region of the beta extracellular domain of the TCR at at least one amino acid residue at position according to SEQ ID NO: 4 selected from the list consisting of 31, 49, 51, 56, and 98. In some embodiments, the inhibitory peptide binds to the TCR at or near a CDR of the variable region of the beta extracellular domain of the TCR at at least one amino acid residue according to SEQ ID NO: 4 selected from the list consisting of ARG31, GLU49, PHE51, ARG56, and MET98.

In some embodiments, the TCR is a gp100 TCR. In some embodiments, the gp100 TCR comprises an alpha domain comprising an amino acid sequence of SEQ ID NO: 7. In some embodiments, the gp100 TCR comprises a beta domain comprising an amino acid sequence of SEQ ID NO: 8. In some embodiments, the inhibitory peptide is a peptide listed in FIGS. 17A-17B. In some embodiments, the inhibitory peptide is a peptide listed in FIG. 20. In some embodiments, the inhibitory peptide is Inhibitory peptide 28 (SEQ ID NO: 60), Inhibitory peptide 29 (SEQ ID NO: 61), Inhibitory peptide 30 (SEQ ID NO: 62), Inhibitory peptide 31 (SEQ ID NO: 63), Inhibitory peptide 32 (SEQ ID NO: 64), Inhibitory peptide 33 (SEQ ID NO: 65), Inhibitory peptide 34 (SEQ ID NO: 66), Inhibitory peptide 35 (SEQ ID NO: 67), Inhibitory peptide 36 (SEQ ID NO: 68), or Inhibitory peptide 37 (SEQ ID NO: 69). In some embodiments, the inhibitory peptide is Inhibitory peptide 29 (SEQ ID NO: 61), Inhibitory peptide 30 (SEQ ID NO: 62), Inhibitory peptide 31 (SEQ ID NO: 63), Inhibitory peptide 35 (SEQ ID NO: 67), or Inhibitory peptide 37 (SEQ ID NO: 69). In some embodiments, the inhibitory peptide is Inhibitory peptide 28 (SEQ ID NO: 60). In some embodiments, the inhibitory peptide is Inhibitory peptide 29 (SEQ ID NO: 61). In some embodiments, the inhibitory peptide is Inhibitory peptide 30 (SEQ ID NO: 62). In some embodiments, the inhibitory peptide is Inhibitory peptide 31 (SEQ ID NO: 63). In some embodiments, the inhibitory peptide is Inhibitory peptide 33 (SEQ ID NO: 65). In some embodiments, the inhibitory peptide is Inhibitory peptide 34 (SEQ ID NO: 66). In some embodiments, the inhibitory peptide is Inhibitory peptide 35 (SEQ ID NO: 67). In some embodiments, the inhibitory peptide is Inhibitory peptide 36 (SEQ ID NO: 68). In some embodiments, the inhibitory peptide is Inhibitory peptide 37 (SEQ ID NO: 69).

In some embodiments, the TCR is a HIV TCR. In some embodiments, the HIV TCR comprises an alpha domain comprising an amino acid sequence of SEQ ID NO: 9. In some embodiments, the HIV TCR comprises a beta domain comprising an amino acid sequence of SEQ ID NO: 10. In some embodiments, the inhibitory peptide is a peptide listed in FIGS. 22A-22B. In some embodiments, the inhibitory peptide is a peptide listed in FIGS. 24A-24B. In some embodiments, the inhibitory peptide is Inhibitory peptide 57 (SEQ ID NO: 98), Inhibitory peptide 58 (SEQ ID NO: 99), Inhibitory peptide 59 (SEQ ID NO: 100), Inhibitory peptide 60 (SEQ ID NO: 101), Inhibitory peptide 61 (SEQ ID NO: 102), Inhibitory peptide 62 (SEQ ID NO: 103), Inhibitory peptide 63 (SEQ ID NO: 104), Inhibitory peptide 64 (SEQ ID NO: 105), Inhibitory peptide 65 (SEQ ID NO: 106), Inhibitory peptide 66 (SEQ ID NO: 107), Inhibitory peptide 67 (SEQ ID NO: 108), Inhibitory peptide 68 (SEQ ID NO: 109), Inhibitory peptide 69 (SEQ ID NO: 110), Inhibitory peptide 70 (SEQ ID NO: 111), Inhibitory peptide 71 (SEQ ID NO: 112), Inhibitory peptide 72 (SEQ ID NO: 113), Inhibitory peptide 73 (SEQ ID NO: 114), Inhibitory peptide 74 (SEQ ID NO: 115), Inhibitory peptide 75 (SEQ ID NO: 117), Inhibitory peptide 77 (SEQ ID NO: 119), Inhibitory peptide 78 (SEQ ID NO: 120), Inhibitory peptide 79 (SEQ ID NO: 121), or Inhibitory peptide 80 (SEQ ID NO: 122). In some embodiments, the inhibitory peptide is Inhibitory peptide 57 (SEQ ID NO: 98). In some embodiments, the inhibitory peptide is Inhibitory peptide 58 (SEQ ID NO: 99). In some embodiments, the inhibitory peptide is Inhibitory peptide 59 (SEQ ID NO: 100). In some embodiments, the inhibitory peptide is Inhibitory peptide 60 (SEQ ID NO: 101). In some embodiments, the inhibitory peptide is Inhibitory peptide 61 (SEQ ID NO: 102). In some embodiments, the inhibitory peptide is Inhibitory peptide 62 (SEQ ID NO: 103). In some embodiments, the inhibitory peptide is Inhibitory peptide 63 (SEQ ID NO: 104). In some embodiments, the inhibitory peptide is Inhibitory peptide 64 (SEQ ID NO: 105). In some embodiments, the inhibitory peptide is Inhibitory peptide 65 (SEQ ID NO: 106). In some embodiments, the inhibitory peptide is Inhibitory peptide 66 (SEQ ID NO: 107). In some embodiments, the inhibitory peptide is Inhibitory peptide 67 (SEQ ID NO: 108). In some embodiments, the inhibitory peptide is Inhibitory peptide 68 (SEQ ID NO: 109). In some embodiments, the inhibitory peptide is Inhibitory peptide 69 (SEQ ID NO: 110). In some embodiments, the inhibitory peptide is Inhibitory peptide 70 (SEQ ID NO: 111). In some embodiments, the inhibitory peptide is Inhibitory peptide 71 (SEQ ID NO: 112). In some embodiments, the inhibitory peptide is Inhibitory peptide 72 (SEQ ID NO: 113). In some embodiments, the inhibitory peptide is Inhibitory peptide 73 (SEQ ID NO: 114). In some embodiments, the inhibitory peptide is Inhibitory peptide 74 (SEQ ID NO: 115). In some embodiments, the inhibitory peptide is Inhibitory peptide 75 (SEQ ID NO: 117). In some embodiments, the inhibitory peptide is Inhibitory peptide 77 (SEQ ID NO: 119). In some embodiments, the inhibitory peptide is Inhibitory peptide 78 (SEQ ID NO: 120). In some embodiments, the inhibitory peptide is Inhibitory peptide 79 (SEQ ID NO: 121). In some embodiments, the inhibitory peptide is Inhibitory peptide 80 (SEQ ID NO: 122).

Discovery Methods for Identifying Peptides that Bind to T Cell Receptors

Disclosed herein, in some embodiments, are methods of identifying a peptide that binds to a T cell receptor (TCR) without the aid of a MHC, the method comprising: (a) incubating a peptide from a peptide library and a TCR in a suitable medium at a neutral pH, wherein the peptide from the peptide library is expressed on a surface of a cell or a phage; (b) removing non-binding peptides by washing the medium at a neutral pH; (c) eluting the peptide that is bound to the TCR by altering the pH to an acidic pH, or a basic pH; and (d) identifying the peptide that is bound to the TCR without the aid of a MHC by sequencing DNA of the cell or the phage on which the peptide is expressed. FIG. 1 illustrates an exemplary schematic of phage peptide panning to identify TCR binding peptide candidates.

In some embodiments, the neutral pH is from 7.0 to 7.8. In some embodiments, the neutral pH is 7.4. In some embodiments, the acidic pH is from 2.0 to 5.0. In some embodiments, the acidic pH is 2.2. In some embodiments, the basic pH is from 9.0 to 11.5. In some embodiments, the basic pH is 11.0.

In some embodiments, steps (a)-(c) are repeated at least one time prior to step (d). In some embodiments, steps (a)-(c) are repeated at least two times prior to step (d). In some embodiments, steps (a)-(c) are repeated at least three times prior to step (d). In some embodiments, steps (a)-(c) are repeated two to five times prior to step (d). In some embodiments, steps (a)-(c) are repeated three to five times prior to step (d). In some embodiments, steps (a)-(c) are repeated four to six times prior to step (d).

In some embodiments, the peptide is a peptide derived from a non-native antigen. In some embodiments, the peptide is a non-human antigen. In some embodiments, the peptide comprises a viral peptide sequence, bacterial peptide sequence, or a fungal peptide sequence.

In some embodiments, the peptide library is a phagemid peptide library. In some embodiments, the peptide from the peptide library is expressed on a surface of an *E. coli* cell. In some embodiments, the peptide from the peptide library is expressed on a surface of a yeast cell. In some embodiments, the peptide from the peptide library is expressed on a surface of a phage. In some embodiments, the peptide library comprises linear peptides. In some embodiments, the peptide library comprises cyclic peptides. In some embodiments, the peptide library is a random peptide library. In some embodiments, the random peptide library is randomized to contain all 20 amino acid residues at each position in the peptide library. In some embodiments, the random peptide library comprises a discrete subset of the 20 possible amino acids at each position in the peptide library. In some embodiments, the random peptide library comprises a single amino acid at one or more discrete positions within the peptide library. In some embodiments, the peptide libraries fix pairs of positions within the peptide library with cysteine residues for the production of disulfide linked cyclic peptide libraries. In some embodiments, the fixed pairs of cysteines are positioned such that the intervening peptide sequences are varied in length between 4 amino acids and 18 amino acids. In some embodiments, the cyclic peptide library comprises randomized amino acids that flank the ring structure at the amino terminal, carboxyl terminal or both between 1 amino acid and 8 amino acids.

In some embodiments, the peptide is not identical to a peptide of pMHC complex. In some embodiments, the peptide contains no or substantially no homology to a peptide of pMHC complex. In some embodiments, the peptide contains at least 5%, 10%, 15%, 20%, 25%, 30%, 35%, 40%, 45%, 50%, 55%, 60%, 65%, 70%, 75%, or 80% sequence identity to a peptide of pMHC complex. In some embodiments, the peptide contains at least 5%, 10%, 15%, 20%, 25%, 30%, 35%, 40%, 45%, 50%, 55%, 60%, 65%, 70%, 75%, or 80% sequence identity to the target antigen.

In some embodiments, the peptide comprises a peptide sequence of at least 5 amino acids in length. In some embodiments, the peptide comprises a peptide sequence of at least 6 amino acids in length. In some embodiments, the peptide comprises a peptide sequence of at least 7 amino acids in length. In some embodiments, the peptide comprises a peptide sequence of at least 8 amino acids in length. In some embodiments, the peptide comprises a peptide sequence of at least 9 amino acids in length. In some embodiments, the peptide comprises a peptide sequence of at least 10 amino acids in length. In some embodiments, the peptide comprises a peptide sequence of at least 11 amino acids in length. In some embodiments, the peptide comprises a peptide sequence of at least 12 amino acids in length. In some embodiments, the peptide comprises a peptide sequence of at least 13 amino acids in length. In some embodiments, the peptide comprises a peptide sequence of at least 14 amino acids in length. In some embodiments, the peptide comprises a peptide sequence of at least 15 amino acids in length. In some embodiments, the peptide comprises a peptide sequence of at least 16 amino acids in length. In some embodiments, the peptide comprises a peptide sequence of at least 17 amino acids in length. In some embodiments, the peptide comprises a peptide sequence of at least 18 amino acids in length. In some embodiments, the peptide comprises a peptide sequence of at least 19 amino acids in length. In some embodiments, the peptide comprises a peptide sequence of at least 20 amino acids in length. In some embodiments, the peptide comprises a peptide sequence of at least 25 amino acids in length. In some embodiments, the peptide comprises a peptide sequence of no more than 30 amino acids in length. In some embodiments, the peptide comprises a peptide sequence of at least 10 to 30 amino acids in length. In some embodiments, the peptide is a linear peptide. In some embodiments, the peptide is a cyclic peptide.

In some embodiments, the peptide comprises a modified amino acid, a non-natural amino acid, a modified non-natural amino acid, or combination thereof. In some embodiments, the modified amino acid or modified non-natural amino acid comprises a post-translational modification. In some embodiments, the modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Modification are made anywhere on the peptide including the peptide backbone, or the amino acid side chains. In some embodiments, the peptide comprises an alkyne or dibenzocyclooctyne modified amino acid for reacting with an azide functionalized molecule. In some embodiments, the peptide comprises a trans-cyclooctene, vinyl, or methylcyclopropene modified amino acid for reacting with a tetrazine functionalized molecule.

In some embodiments, the peptide binds to the TCR through ionic interactions, electrostatic interactions, hydrophobic interactions, Pi-stacking interactions, and H-bonding interactions, or a combination thereof.

In some embodiments, the binding of the peptide to the TCR conceals, sterically blocks, or inhibits the antigen binding site of TCR from interacting with a pMHC complex. In some embodiments, the binding of the peptide to the TCR sterically blocks the interaction of the TCR with a pMHC complex. In some embodiments, the binding of the peptide to the TCR conceals, blocks, or inhibits the antigen binding site of TCR from interacting with a pMHC complex. In some embodiments, the binding of the peptide to the TCR blocks the interaction of the TCR with a pMHC complex.

In some embodiments, the inhibitory peptide binds to the TCR alpha extracellular domain, to the TCR beta extracellular domain, or both to conceal, sterically block, or inhibit the antigen binding site of the TCR from interacting with a pMHC complex. In some embodiments, the inhibitory peptide binds to the TCR alpha extracellular domain, to the TCR beta extracellular domain, or both to conceal, block, or inhibit the antigen binding site of the TCR from interacting with a pMHC complex. In some embodiments, the inhibitory peptide binds to a constant region of the alpha extracellular domain of the TCR, or to the constant region of the beta extracellular domain of the TCR. In some embodiments, the inhibitory peptide binds to a variable region of the alpha extracellular domain of the TCR, a variable region of the beta extracellular domain of the TCR, or both. In some embodiments, the inhibitory peptide binds to the TCR at or near a CDR of the TCR. In some embodiments, the inhibitory peptide binds to the TCR at or near a CDR1 of the TCR. In some embodiments, the inhibitory peptide binds to the TCR at or near a CDR2 of the TCR. In some embodiments, the inhibitory peptide binds to the TCR at or near a CDR3 of the TCR. In some embodiments, the inhibitory peptide binds to the TCR at or near a CDR1 and a CDR2 of the TCR. In some embodiments, the inhibitory peptide binds to the TCR at or near a CDR1 and a CDR3 of the TCR. In some embodiments, the inhibitory peptide binds to the TCR at or near a CDR2 and a CDR3 of the TCR. In some embodiments, the inhibitory peptide binds to the TCR at or near a CDR1, a CDR2, and a CDR3 of the TCR. In some embodiments, the inhibitory peptide binds to the TCR at or near a complementarity-determining region (CDR) of the variable region of the alpha extracellular domain of the TCR, to the TCR at or near a complementarity-determining region (CDR) of the variable region of the beta extracellular domain of the TCR, or both.

In some embodiments, the TCR is expressed on a surface of the T cell. In some embodiments, the TCR comprises a TCR alpha extracellular domain, and a transmembrane domain, and a TCR beta extracellular domain, and a transmembrane domain. In some embodiments, the TCR alpha extracellular domain comprises a variable region. In some embodiments, the TCR alpha extracellular domain comprises a variable region, a joining region, and a constant region. In some embodiments, the TCR alpha extracellular domain is a full length TCR alpha extracellular domain. In some embodiments, the TCR alpha extracellular domain comprises three hyper-variable complementarity determining regions (CDRs) within the variable region. In some embodiments, the TCR beta extracellular domain comprises a variable region. In some embodiments, the TCR beta extracellular domain comprises a variable region, a joining region, and a constant region. In some embodiments, the TCR beta extracellular domain is a full length TCR beta extracellular domain. In some embodiments, the TCR beta extracellular domain comprises three hyper-variable complementarity determining regions (CDRs).

In some embodiments, the TCR is a soluble TCR. In some embodiments, the TCR comprises a TCR alpha extracellular domain, and a TCR beta extracellular domain. In some embodiments, the TCR alpha extracellular domain comprises a variable region. In some embodiments, the TCR alpha extracellular domain comprises a variable region, a joining region, and a constant region. In some embodiments, the TCR alpha extracellular domain is a full length TCR alpha extracellular domain. In some embodiments, the TCR alpha extracellular domain comprises three hyper-variable complementarity determining regions (CDRs) within the variable region. In some embodiments, the TCR alpha extracellular domain further comprises a truncated transmembrane domain. In some embodiments, the TCR alpha extracellular domain lacks a transmembrane domain. In some embodiments, the TCR beta extracellular domain comprises a variable region. In some embodiments, the TCR beta extracellular domain comprises a variable region, a joining region, and a constant region. In some embodiments, the TCR beta extracellular domain is a full length TCR beta extracellular domain. In some embodiments, the TCR beta extracellular domain comprises three hyper-variable complementarity determining regions (CDRs). In some embodiments, the TCR beta extracellular domain further comprises a truncated transmembrane domain. In some embodiments, the TCR beta extracellular domain lacks a transmembrane domain.

In some embodiments, the TCR is an engineered TCR. In some embodiments, the engineered TCR is modified to increase binding affinity of the TCR to the peptide. In some embodiments, the engineered TCR is modified to increase stability of the TCR. In some embodiments, the engineered TCR is modified to increase binding affinity of the TCR to the pMHC complex. In some embodiments, the engineered TCR is modified to decrease aggregation.

In some embodiments, the TCR alpha extracellular domain comprises a mutation to increase binding affinity of the TCR to the peptide. In some embodiments, the TCR alpha extracellular domain comprises a mutation to increase stability of the TCR. In some embodiments, the TCR beta extracellular domain comprises a mutation to increase binding affinity of the TCR to the peptide. In some embodiments, the TCR beta extracellular domain comprises a mutation to increase stability of the TCR. In some embodiments, the TCR alpha extracellular domain and the TCR beta extracellular domain comprises a mutation to increase the binding affinity of the TCR to the peptide. In some embodiments, the TCR alpha extracellular domain and the TCR beta extracellular domain comprises a mutation to increase stability of the TCR. In some embodiments, the TCR alpha extracellular domain comprises a mutation to increase binding affinity of the TCR to the peptide and the TCR alpha extracellular domain of the TCR comprises a mutation to increase stability of the TCR. In some embodiments, the TCR beta extracellular domain comprises a mutation to increase binding affinity of the TCR to the peptide and the TCR beta extracellular domain of the TCR comprises a mutation to increase stability of the TCR. In some embodiments, the TCR alpha extracellular domain of the TCR comprises a mutation to increase binding affinity of the TCR to the peptide and the TCR beta extracellular domain of the TCR comprises a mutation to increase binding affinity of the TCR to the peptide. In some embodiments, the TCR alpha extracellular domain of the TCR comprises a mutation to increase stability of the TCR and the TCR beta extracellular domain of the TCR comprises a mutation to increase stability of the TCR. In some embodiments, the TCR alpha extracellular domain of the TCR comprises a mutation to increase binding affinity of the TCR to the peptide and the TCR beta extracellular domain of the TCR comprises a mutation to increase stability of the TCR. In some embodiments, the TCR alpha extracellular domain of the TCR comprises a mutation to increase stability of the TCR and the TCR beta extracellular domain of the TCR comprises a mutation to increase binding affinity of the TCR to the peptide. In some embodiments, the TCR alpha extracellular domain comprises a mutation to increase binding affinity of the TCR to the pMHC complex. In some embodiments, the TCR beta extracellular domain comprises a mutation to increase binding affinity of the TCR to the pMHC complex. In some embodiments, the TCR alpha extracellular domain and the TCR beta extracellular domain comprises a mutation to increase binding affinity of the TCR to the pMHC complex.

In some embodiments, the TCR includes, but is not limited to, a PRAME TCR, a MAGE-A1 TCR, a MAGE-4 TCR, a MAGE-A10 TCR, a NY-ESO-1 TCR, an alpha fetoprotein (AFP) TCR, a Mage-A3 TCR, a gp100 TCR, and an HIV TCR. In some embodiments, the TCR is a PRAME TCR. In some embodiments, the TCR is a MAGE-A1 TCR. In some embodiments, the TCR is a MAGE-4 TCR. In some embodiments, the TCR is a MAGE-A10 TCR. In some embodiments, the TCR is a NY-ESO-1 TCR. In some embodiments, the TCR is an alpha fetoprotein (AFP) TCR.

In some embodiments, the TCR is a Mage-A3 TCR. In some embodiments, the Mage-A3 TCR comprises an alpha domain comprising an amino acid sequence of SEQ ID NO: 3. In some embodiments, the Mage-A3 TCR comprises a beta domain comprising an amino acid sequence of SEQ ID NO: 4. In some embodiments, the inhibitory peptide is a peptide listed in FIGS. 7A-7B. In some embodiments, the inhibitory peptide is a peptide listed in FIGS. 10A-10B. In some embodiments, the inhibitory peptide is Inhibitory peptide 2 (SEQ ID NO: 11), Inhibitory peptide 3 (SEQ ID NO: 12), Inhibitory peptide 4 (SEQ ID NO: 13), Inhibitory peptide 5 (SEQ ID NO: 14), Inhibitory peptide 1 (SEQ ID NO: 15), Inhibitory peptide 6 (SEQ ID NO: 16), Inhibitory peptide 7 (SEQ ID NO: 17), Inhibitory peptide 8 (SEQ ID NO: 18), Inhibitory peptide 9 (SEQ ID NO: 19), Inhibitory peptide 10 (SEQ ID NO: 20), Inhibitory peptide 11 (SEQ ID NO: 21), Inhibitory peptide 12 (SEQ ID NO: 22), Inhibitory peptide 13 (SEQ ID NO: 23), Inhibitory peptide 14 (SEQ ID NO: 24), Inhibitory peptide 15 (SEQ ID NO: 25), Inhibitory peptide 16 (SEQ ID NO: 26), Inhibitory peptide 17 (SEQ ID NO: 27), Inhibitory peptide 18 (SEQ ID NO: 28), Inhibitory peptide 19 (SEQ ID NO: 29), Inhibitory peptide 20 (SEQ ID NO: 30), Inhibitory peptide 25 (SEQ ID NO: 1), or Inhibitory peptide 26 (SEQ ID NO: 58). In some embodiments, the inhibitory peptide is Inhibitory peptide 2 (SEQ ID NO: 11), Inhibitory peptide 3 (SEQ ID NO: 12), Inhibitory peptide 1 (SEQ ID NO: 15), Inhibitory peptide 6 (SEQ ID NO: 16), Inhibitory peptide 7 (SEQ ID NO: 17), Inhibitory peptide 9 (SEQ ID NO: 19), Inhibitory peptide 12 (SEQ ID NO: 22), Inhibitory peptide 13 (SEQ ID NO: 23), Inhibitory peptide 15 (SEQ ID NO: 25), or Inhibitory peptide 25 (SEQ ID NO: 1). In some embodiments, the inhibitory peptide is Inhibitory peptide 2 (SEQ ID NO: 11). In some embodiments, the inhibitory peptide is Inhibitory peptide 3 (SEQ ID NO: 12). In some embodiments, the inhibitory peptide is Inhibitory peptide 4 (SEQ ID NO: 13). In some embodiments, the inhibitory peptide is Inhibitory peptide 5 (SEQ ID NO: 14). In some embodiments, the inhibitory peptide is Inhibitory peptide 1 (SEQ ID NO: 15). In some embodiments, the inhibitory peptide is Inhibitory peptide 6 (SEQ ID NO: 16). In some embodiments, the inhibitory peptide is Inhibitory peptide 7 (SEQ ID NO: 17). In some embodiments, the inhibitory peptide is Inhibitory peptide 8 (SEQ ID NO: 18). In some embodiments, the inhibitory peptide is Inhibitory peptide 9 (SEQ ID NO: 19). In some embodiments, the inhibitory peptide is Inhibitory peptide 10 (SEQ ID NO: 20). In some embodiments, the inhibitory peptide is Inhibitory peptide 11 (SEQ ID NO: 21). In some embodiments, the inhibitory peptide is Inhibitory peptide 12 (SEQ ID NO: 22). In some embodiments, the inhibitory peptide is Inhibitory peptide 13 (SEQ ID NO: 23). In some embodiments, the inhibitory peptide is Inhibitory peptide 14 (SEQ ID NO: 24). In some embodiments, the inhibitory peptide is Inhibitory peptide 15 (SEQ ID NO: 25). In some embodiments, the inhibitory peptide is Inhibitory peptide 16 (SEQ ID NO: 26). In some embodiments, the inhibitory peptide is Inhibitory peptide 17 (SEQ ID NO: 27). In some embodiments, the inhibitory peptide is Inhibitory peptide 18 (SEQ ID NO: 28). In some embodiments, the inhibitory peptide is Inhibitory peptide 19 (SEQ ID NO: 29). In some embodiments, the inhibitory peptide is Inhibitory peptide 20 (SEQ ID NO: 30). In some embodiments, the inhibitory peptide is Inhibitory peptide 25 (SEQ ID NO: 1). In some embodiments, the inhibitory peptide is Inhibitory peptide 26 (SEQ ID NO: 58). In some embodiments, the inhibitory peptide comprises the amino acid sequence of VSCKDVYDEAFCW (SEQ ID NO: 2). In some embodiments, the inhibitory peptide comprising the amino acid sequence of VSCKDVYDEAFCW (SEQ ID NO: 2) binds to a Mage-A3 TCR. In some embodiments, the TCR with a bound inhibitory peptide comprises an amino acid sequence of SEQ ID NO: 5. In some embodiments, the TCR with a bound inhibitory peptide comprises an amino acid sequence of SEQ ID NO: 6. In some embodiments, the inhibitory peptide binds to the TCR at or near a CDR of the variable region of the alpha extracellular domain of the TCR at at least one amino acid residue at position according to SEQ ID NO: 3 selected from the list consisting of 32, 94, and 102. In some embodiments, the inhibitory peptide binds to the TCR at or near a CDR of the variable region of the alpha extracellular domain of the TCR at at least one amino acid residue according to SEQ ID NO: 3 selected from the list consisting of TYR32, ARG94, and PHE102. In some embodiments, the inhibitory peptide binds to the TCR at or near a CDR1, CDR2, and CDR3 of the variable region of the beta extracellular domain of the TCR. In some embodiments, the inhibitory peptide binds to the TCR at or near a CDR of the variable region of the beta extracellular domain of the TCR at at least one amino acid residue at position according to SEQ ID NO: 4 selected from the list consisting of 31, 49, 51, 56, and 98. In some embodiments, the inhibitory peptide binds to the TCR at or near a CDR of the variable region of the beta extracellular domain of the TCR at at least one amino acid residue according to SEQ ID NO: 4 selected from the list consisting of ARG31, GLU49, PHE51, ARG56, and MET98.

In some embodiments, the TCR is a gp100 TCR. In some embodiments, the gp100 TCR comprises an alpha domain comprising an amino acid sequence of SEQ ID NO: 7. In some embodiments, the gp100 TCR comprises a beta domain comprising an amino acid sequence of SEQ ID NO: 8. In some embodiments, the inhibitory peptide is a peptide listed in FIGS. 17A-17B. In some embodiments, the inhibitory peptide is a peptide listed in FIG. 20. In some embodiments, the inhibitory peptide is Inhibitory peptide 28 (SEQ ID NO: 60), Inhibitory peptide 29 (SEQ ID NO: 61), Inhibitory peptide 30 (SEQ ID NO: 62), Inhibitory peptide 31 (SEQ ID NO: 63), Inhibitory peptide 32, (SEQ ID NO: 64) Inhibitory peptide 33 (SEQ ID NO: 65), Inhibitory peptide 34 (SEQ ID NO: 66), Inhibitory peptide 35 (SEQ ID NO: 67), Inhibitory peptide 36 (SEQ ID NO: 68), or Inhibitory peptide 37 (SEQ ID NO: 69). In some embodiments, the inhibitory peptide is Inhibitory peptide 29 (SEQ ID NO: 61), Inhibitory peptide 30 (SEQ ID NO: 62), Inhibitory peptide 31 (SEQ ID NO: 63), Inhibitory peptide 35 (SEQ ID NO: 67), or Inhibitory peptide 37 (SEQ ID NO: 69). In some embodiments, the inhibitory peptide is Inhibitory peptide 28 (SEQ ID NO: 60). In some embodiments, the inhibitory peptide is Inhibitory peptide 29 (SEQ ID NO: 61). In some embodiments, the inhibitory peptide is Inhibitory peptide 30 (SEQ ID NO: 62). In some embodiments, the inhibitory peptide is Inhibitory peptide 31 (SEQ ID NO: 63). In some embodiments, the inhibitory peptide is Inhibitory peptide 33 (SEQ ID NO: 65). In some embodiments, the inhibitory peptide is Inhibitory peptide 34 (SEQ ID NO: 66). In some embodiments, the inhibitory peptide is Inhibitory peptide 35 (SEQ ID NO: 67). In some embodiments, the inhibitory peptide is Inhibitory peptide 36 (SEQ ID NO: 68). In some embodiments, the inhibitory peptide is Inhibitory peptide 37 (SEQ ID NO: 69).

In some embodiments, the TCR is a HIV TCR. In some embodiments, the HIV TCR comprises an alpha domain comprising an amino acid sequence of SEQ ID NO: 9. In some embodiments, the HIV TCR comprises a beta domain comprising an amino acid sequence of SEQ ID NO: 10. In some embodiments, the inhibitory peptide is a peptide listed in FIGS. 22A-22B. In some embodiments, the inhibitory peptide is a peptide listed in FIGS. 24A-24B. In some embodiments, the inhibitory peptide is Inhibitory peptide 57 (SEQ ID NO: 98), Inhibitory peptide 58 (SEQ ID NO: 99), Inhibitory peptide 59 (SEQ ID NO: 100), Inhibitory peptide 60 (SEQ ID NO: 101), Inhibitory peptide 61 (SEQ ID NO: 102), Inhibitory peptide 62 (SEQ ID NO: 103), Inhibitory peptide 63 (SEQ ID NO: 104), Inhibitory peptide 64 (SEQ ID NO: 105), Inhibitory peptide 65 (SEQ ID NO: 106), Inhibitory peptide 66 (SEQ ID NO: 107), Inhibitory peptide 67 (SEQ ID NO: 108), Inhibitory peptide 68 (SEQ ID NO: 109), Inhibitory peptide 69 (SEQ ID NO: 110), Inhibitory peptide 70 (SEQ ID NO: 111), Inhibitory peptide 71 (SEQ ID NO: 112), Inhibitory peptide 72 (SEQ ID NO: 113), Inhibitory peptide 73 (SEQ ID NO: 114), Inhibitory peptide 74 (SEQ ID NO: 115), Inhibitory peptide 75 (SEQ ID NO: 117), Inhibitory peptide 77 (SEQ ID NO: 119), Inhibitory peptide 78 (SEQ ID NO: 120), Inhibitory peptide 79 (SEQ ID NO: 121), or Inhibitory peptide 80 (SEQ ID NO: 122). In some embodiments, the inhibitory peptide is Inhibitory peptide 57 (SEQ ID NO: 98). In some embodiments, the inhibitory peptide is Inhibitory peptide 58 (SEQ ID NO: 99). In some embodiments, the inhibitory peptide is Inhibitory peptide 59 (SEQ ID NO: 100). In some embodiments, the inhibitory peptide is Inhibitory peptide 60 (SEQ ID NO: 101). In some embodiments, the inhibitory peptide is Inhibitory peptide 61 (SEQ ID NO: 102). In some embodiments, the inhibitory peptide is Inhibitory peptide 62 (SEQ ID NO: 103). In some embodiments, the inhibitory peptide is Inhibitory peptide 63 (SEQ ID NO: 104). In some embodiments, the inhibitory peptide is Inhibitory peptide 64 (SEQ ID NO: 105). In some embodiments, the inhibitory peptide is Inhibitory peptide 65 (SEQ ID NO: 106). In some embodiments, the inhibitory peptide is Inhibitory peptide 66 (SEQ ID NO: 107). In some embodiments, the inhibitory peptide is Inhibitory peptide 67 (SEQ ID NO: 108). In some embodiments, the inhibitory peptide is Inhibitory peptide 68 (SEQ ID NO: 109). In some embodiments, the inhibitory peptide is Inhibitory peptide 69 (SEQ ID NO: 110). In some embodiments, the inhibitory peptide is Inhibitory peptide 70 (SEQ ID NO:

111). In some embodiments, the inhibitory peptide is Inhibitory peptide 71 (SEQ ID NO: 112). In some embodiments, the inhibitory peptide is Inhibitory peptide 72 (SEQ ID NO: 113). In some embodiments, the inhibitory peptide is Inhibitory peptide 73 (SEQ ID NO: 114). In some embodiments, the inhibitory peptide is Inhibitory peptide 74 (SEQ ID NO: 115). In some embodiments, the inhibitory peptide is Inhibitory peptide 75 (SEQ ID NO: 117). In some embodiments, the inhibitory peptide is Inhibitory peptide 77 (SEQ ID NO: 119). In some embodiments, the inhibitory peptide is Inhibitory peptide 78 (SEQ ID NO: 120). In some embodiments, the inhibitory peptide is Inhibitory peptide 79 (SEQ ID NO: 121). In some embodiments, the inhibitory peptide is Inhibitory peptide 80 (SEQ ID NO: 122).

EXAMPLES

Example 1. Screening of Candidate Peptides

Peptides with the ability to bind to a T cell receptor (TCR) of interest are identified by biopanning a phagemid-display libraries of candidate peptides (FIG. 1). Libraries are created via the introduction of recombinant expression of peptides fused to the m13 bacteriophage coat protein III (pIII), resulting in display of the candidate peptides on the surface of the secreted bacteriophage. The candidate peptide libraries have variable amino acid sequences and collectively variable amino acid lengths.

Biopanning of m13 phagemid p3 displayed peptide libraries is performed with biotin-conjugated Mage-A3 TCR immobilized on streptavidin coated paramagnetic beads. Following binding to the target at pH 7.4 and subsequent washing steps, specifically bound phage are recovered by elution at pH 2.2, or at pH 11.0. Though individual clones can be sequenced or tested after a single round, enrichment of specific binding clones is typically accomplished by 2-4 rounds of successive biopanning and amplification. Following the enrichment of pools, phage biopanning phage pools are infected into TG1 cells and plated out on LB-ampicillin/ agar plates for subsequent clonal isolation and characterization.

Example 2. Preparation of Soluble TCRs

Expression plasmids encoding the TCR alpha and beta chains or the TCR gamma and delta chains were produced using standard molecular biology techniques. Plasmids were transformed into chemically-competent cells and grown overnight at 37° C. Protein expression was induced by the addition of Isopropyl β-D-1-thiogalactopyranoside (IPTG) to 1 mM and bacteria were grown for a further 3 hours at 37° C. Bacteria were harvested by centrifugation at 4000×g for 15 minutes and lysed in a protein extraction reagent containing DNAse. Lysis proceeded for 1 hour at room temperature with agitation before inclusion bodies were harvested by centrifugation at 10000×g for 5 minutes. Pellets were washed twice with a detergent buffer containing 1% Triton X100 and resuspended in a buffered saline solution.

Soluble TCRs were prepared by dissolving alpha and beta inclusion bodies in 6M guanidine-HCl containing 10 mM dithiothreitol and incubating at 37° C. for 30 minutes. Samples were diluted into 1 ml urea folding buffer (5 M urea; 0.4 M L-arginine; 0.1 M Tris-CI, pH 8.1; 2 mM EDTA; 6.5 mM β-mercapthoethylamine; 1.9 mM cystamine) and dialysed against eight volumes of water overnight at 4° C., followed by dialysis for a further 24 hours in eight volumes of 10 mM Tris (8.1), with one buffer change. Dialysate (30 ml) was concentrated to 1 ml. Concentrated protein was diluted to 5 ml in phosphate-buffered saline and concentrated to 0.5 ml.

Figure 2A:
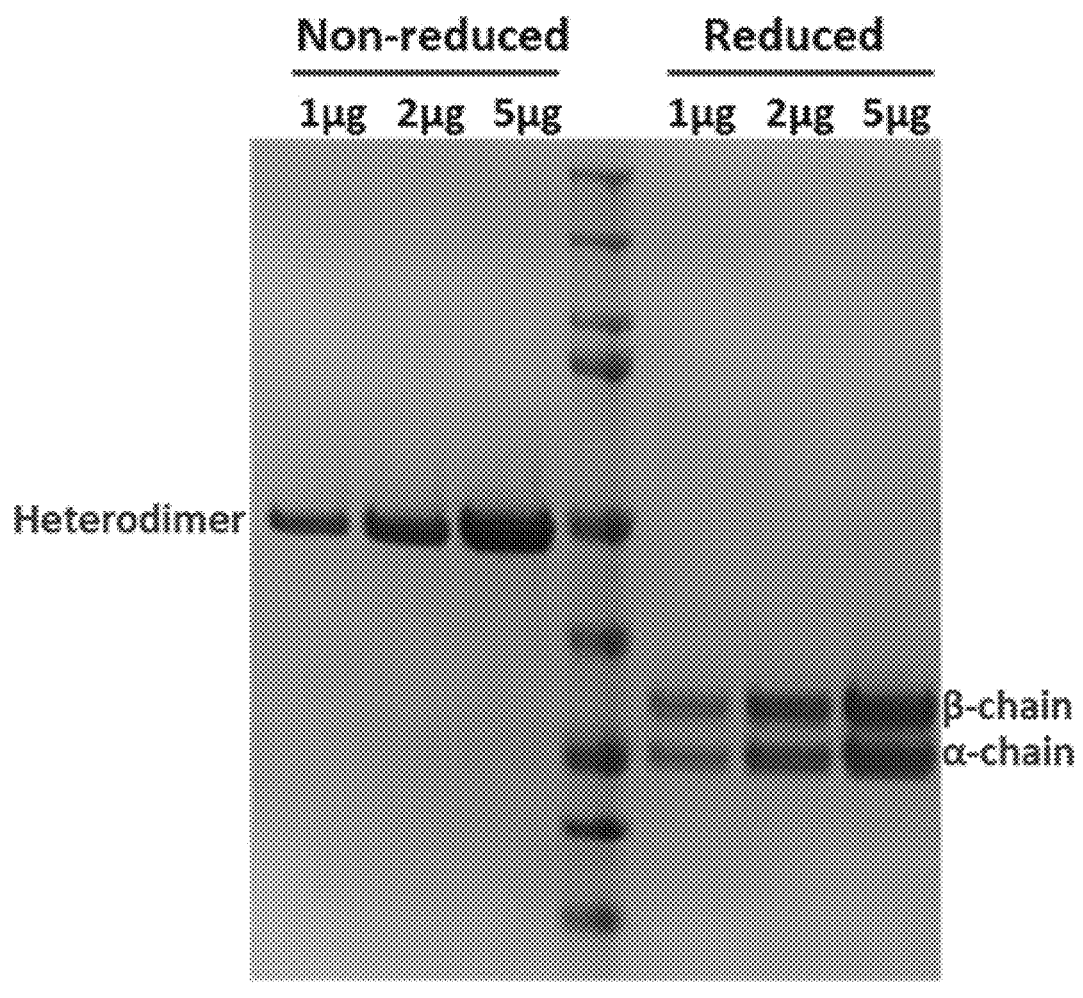
FIG. 2A-FIG. 2E illustrate analytical and functional characterization of a functional Mage-A3 soluble TCR.
Figure 2B:
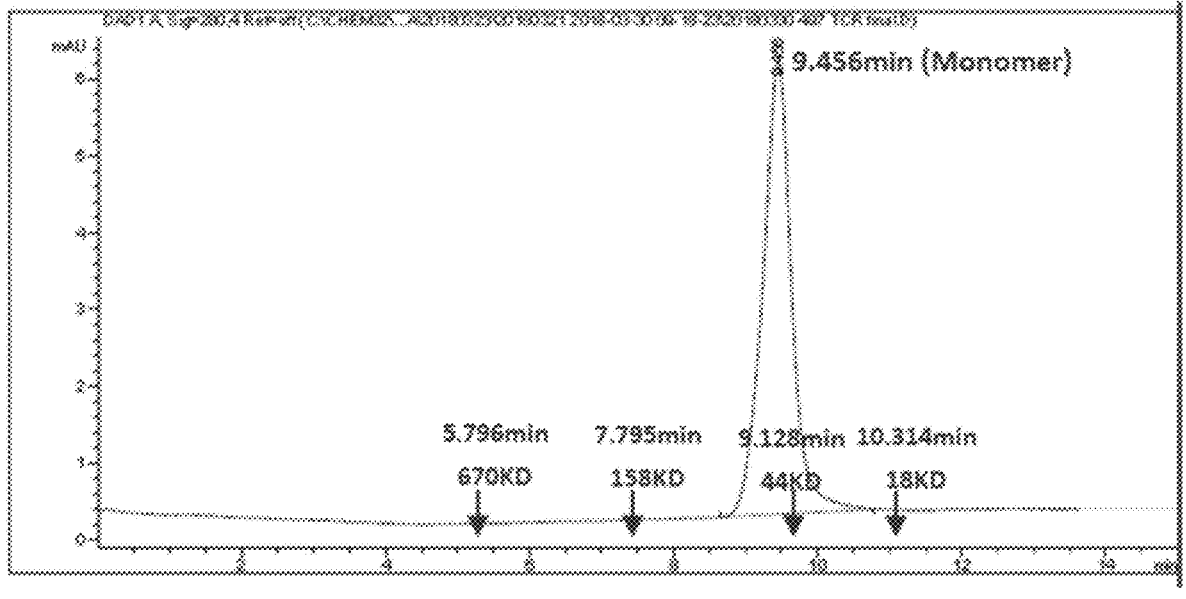
Figure 2C:
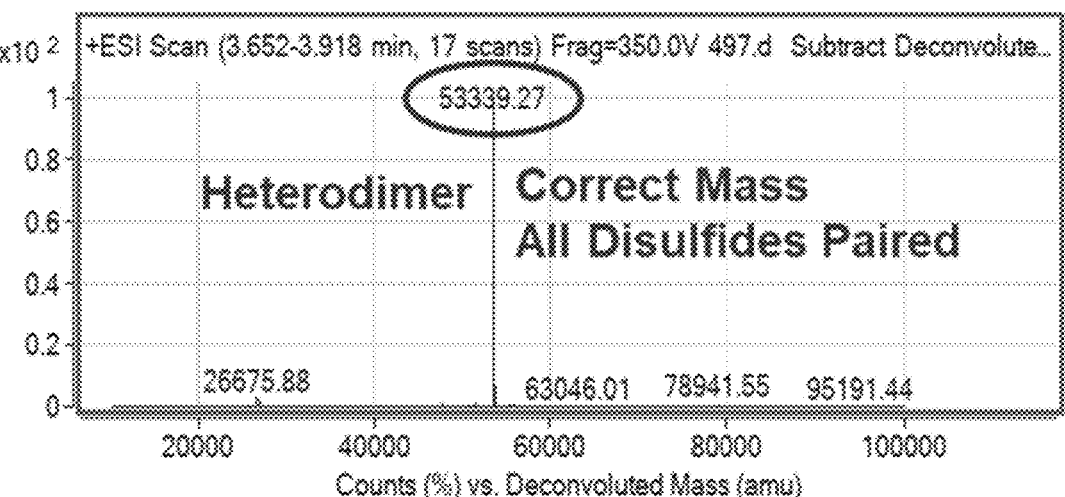

The resulting soluble TCRs were tested for their biochemical integrity by three methods. First, portions of the resulting TCRs were tested by heating in loading buffer in the presence or absence of reducing agent. Several concentrations of total protein were then examined by SDS-PAGE analysis to insure consistent results. Second, a portion of the resulting TCR was tested by size exclusion chromatography to determine whether there were smaller or larger than expected molecular weight components, indicating undimerized monomer or aggregating protein, respectively (FIG. 2A). Finally, the molecular mass by LC-MS methods was measured to further prove correct disulfide pairing was present in the reconstituted heterodimeric TCR (FIG. 2B, FIG. 2C).

TCR fusion constructs were either produced in *E. coli* cells similar to methods described above or transiently produced in suspension mammalian HEK293 cells according to known methods.

Example 3. Kinetic Binding of Soluble TCR to pMHC

Figures 2D, 2E:
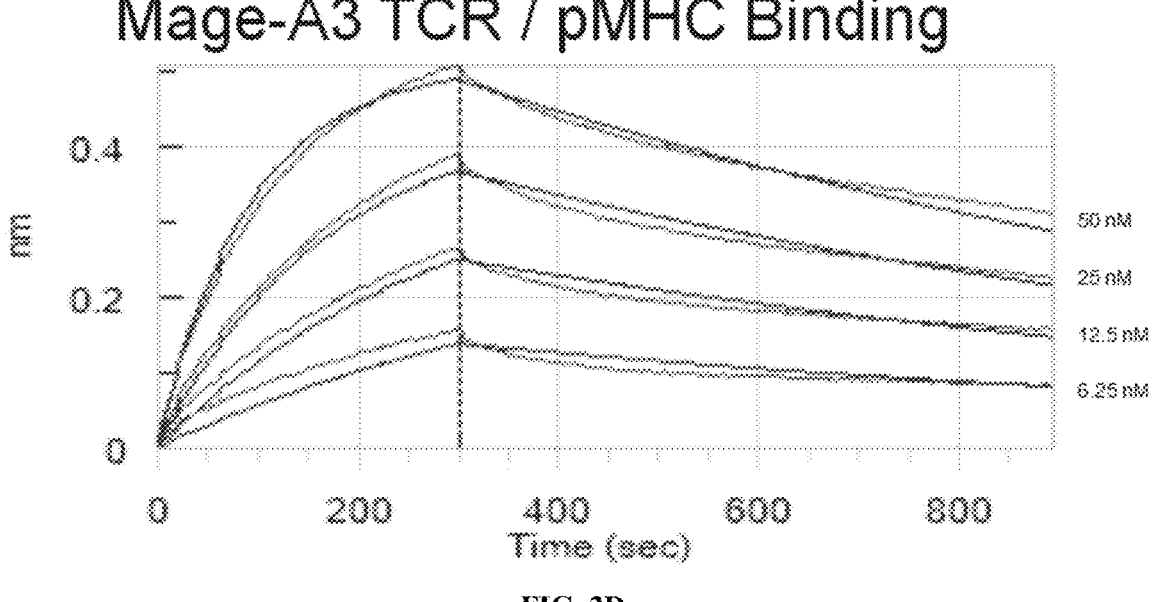

Kinetic binding of soluble TCR to pMHC was measured using a ForteBio Octet RED96 instrument. Biotinylated pMHC was first captured on streptavidin biosensors. Sensors were quenched using excess biocytin and then baselined in buffer. TCR was titrated in a 2-fold dilution series starting from 50 nM and was associated onto the pMHC loaded biosensor. Association signal was monitored in real-time. Biosensors were then transferred to buffer and the dissociation of TCR was measured in real-time. Data was background corrected, fit to a classic 1:1 binding model, and used to calculate kinetic rate constants. (FIG. 2D, FIG. 2E)

Example 4. Identification and Confirmation of Phagemid-Displayed Peptides that Bind Directly to the Mage-A3 sTCR and are Competed by DMHC Phagemid Hit Identification ELISA For hit identification, individual colonies were grown in 96-deep well plates for 2-4 hours and infected with helper phage to produce peptide displayed phagemid following an overnight growth. The next day the deep well plates were centrifuged to separate the soluble phagemid from the *E. coli* cells. The phagemid containing supernatants were then combined with PBS-Tween 20 (0.05%)+BSA (1%) pH neutral blocking buffer and incubated in previously Mage-A3 TCR coated and blocked wells. After binding at 4° C. the plates were washed, and specifically bound phage were detected by anti-m13 HRP conjugated antibodies using standard TMB-based chromogenic ELISA procedures. Daughter plates or individual wells were subjected to standard DNA sequencing for peptide identification.

Figure 3A:
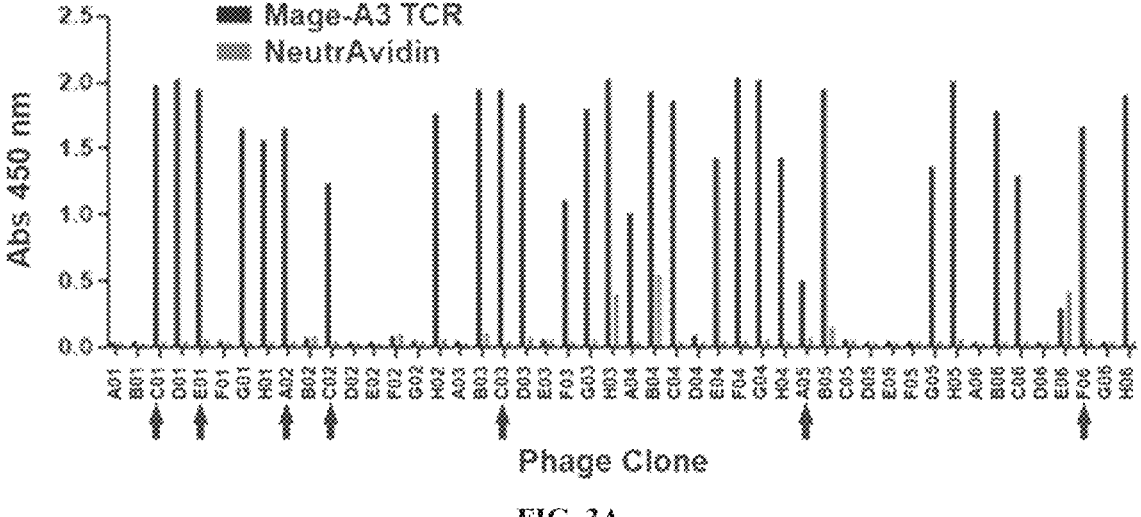
FIG. 3A-FIG. 3C illustrate identification and confirmation of peptides that bind directly to the Mage-A3 sTCR and inhibit TCR/Mage-A3 pMHC binding.
Figure 3B:
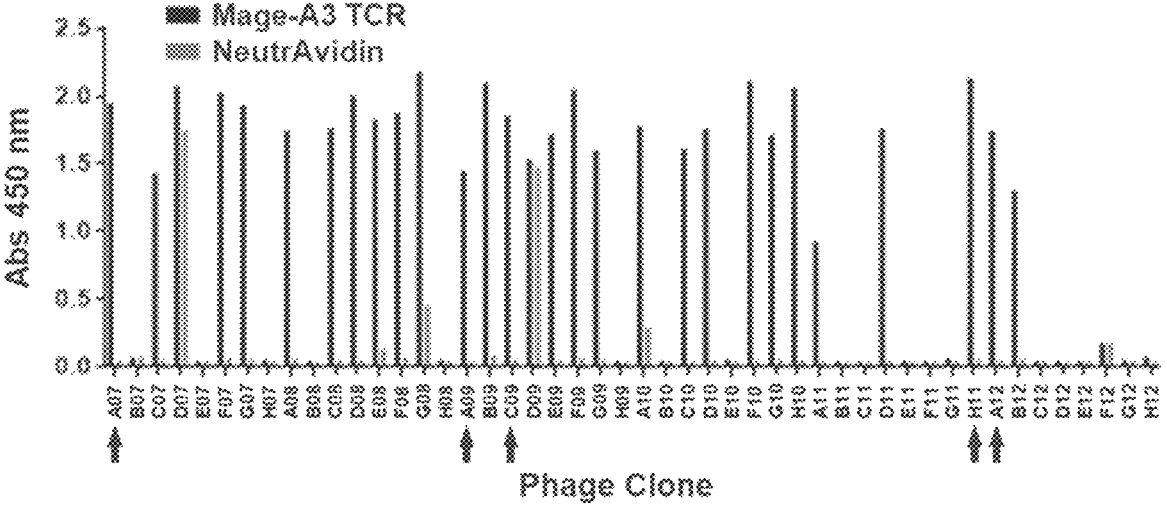

Representative examples are seen in FIG. 3A and FIG. 3B of phagemid ELISA of a collection of enriched clones resulting from three rounds of biopanning against Mage-A3 TCR Phagemid Competition ELISA Assay Phagemid peptide clones were next tested to determine whether they bound within the antigen binding space of the antibody, by target-based competition assay. Biotin-Mage-A3 TCR were immobilized and blocked 96-well ELISA plates similar to above. Next, Mage-A3 pMHC was added to the well to block the antigen binding site. After a brief incubation period phagemid supernatants were next added to the wells. Following an incubation at 4° C. the plates were washed, and specifically bound phage were detected by anti-m13 HRP conjugated antibodies using standard TMB-based chromogenic ELISA procedures. Phagemid clones binding within the pMHC binding pocket of the TCR would be blocked and be identified by a decreased ELISA signal, compared to a well lacking previous antigen blockade. Sequences are shown in Table 1.

TABLE 1

| Name | Sequence | SEQ ID NO: |
| --- | --- | --- |
| MAGE-A3 | EVDPIGHLY | 1 |
| Inhibitory peptide 1 | VSCKDVYDE AFCW | 2 |

Figure 3C:
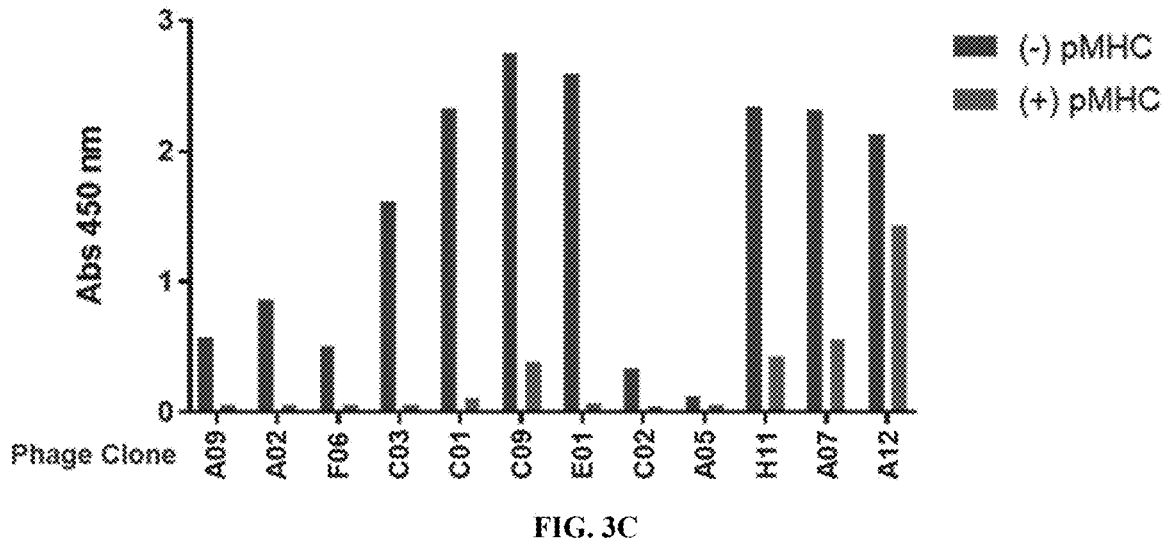

A representative example of the phagemid competition ELISA is seen in FIG. 3C from a collection of enriched clones isolated after three rounds of biopanning against Mage-A3 TCR A quantitative summary of selected unique clones and their respective peptide sequences are shown in FIGS. 7A-7B.

Figures 4A, 4B:
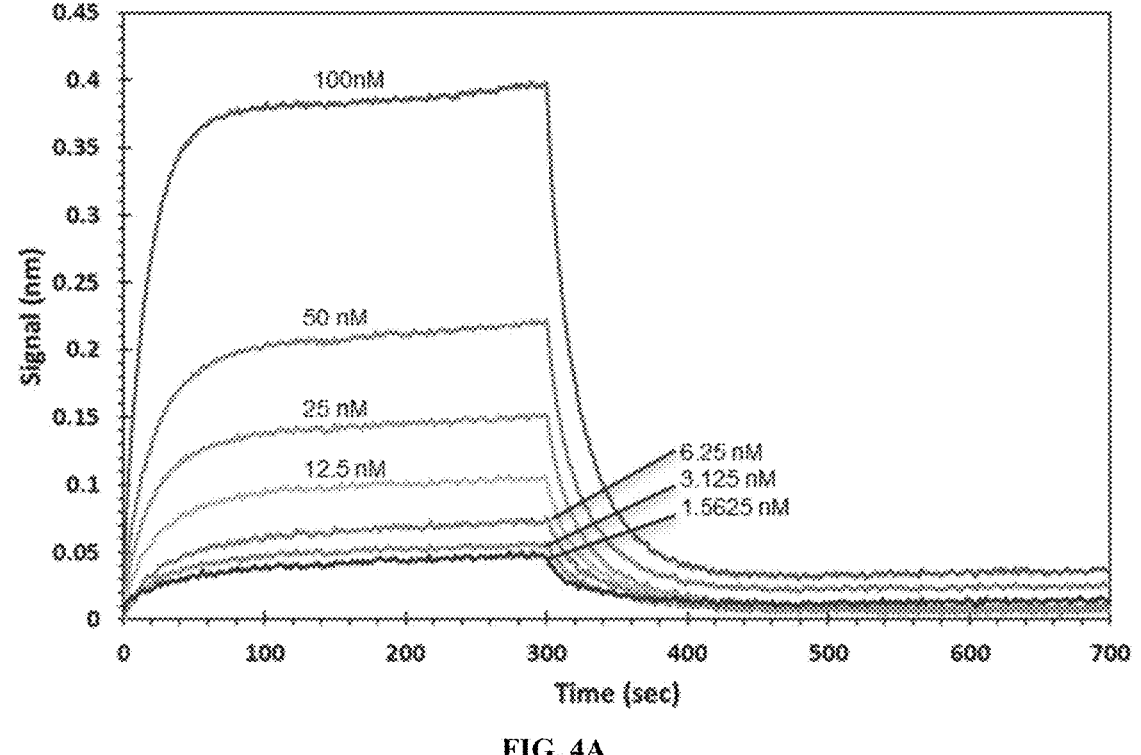
FIG. 4A-FIG. 4B illustrate functional characterization of binding between inhibitory peptide 1 and Mage-A3 sTCR.

Example 5. Functional Characterization of Binding Between Inhibitory Peptide 1 and Mage-3A sTCR Kinetic Binding of TCR to Inhibitory Peptide:

Kinetic binding of soluble TCR to inhibitory peptides was measured using an ForteBio Octet RED96 instrument. Biotinylated inhibitory peptide was first captured on streptavidin biosensors. Sensors were quenched using excess biocytin and then baselined in buffer. TCR was titrated in a 2-fold dilution series starting from 100 nM and was associated onto the inhibitory peptide loaded biosensor. Association signal was monitored in real-time. Biosensors were then transferred to buffer and the dissociation of TCR was measured in real-time. Data was baseline corrected, fit to a classic 1:1 binding model, and used to calculate kinetic rate constants. (FIG. 4A-FIG. 4B).

Figures 5, 6:
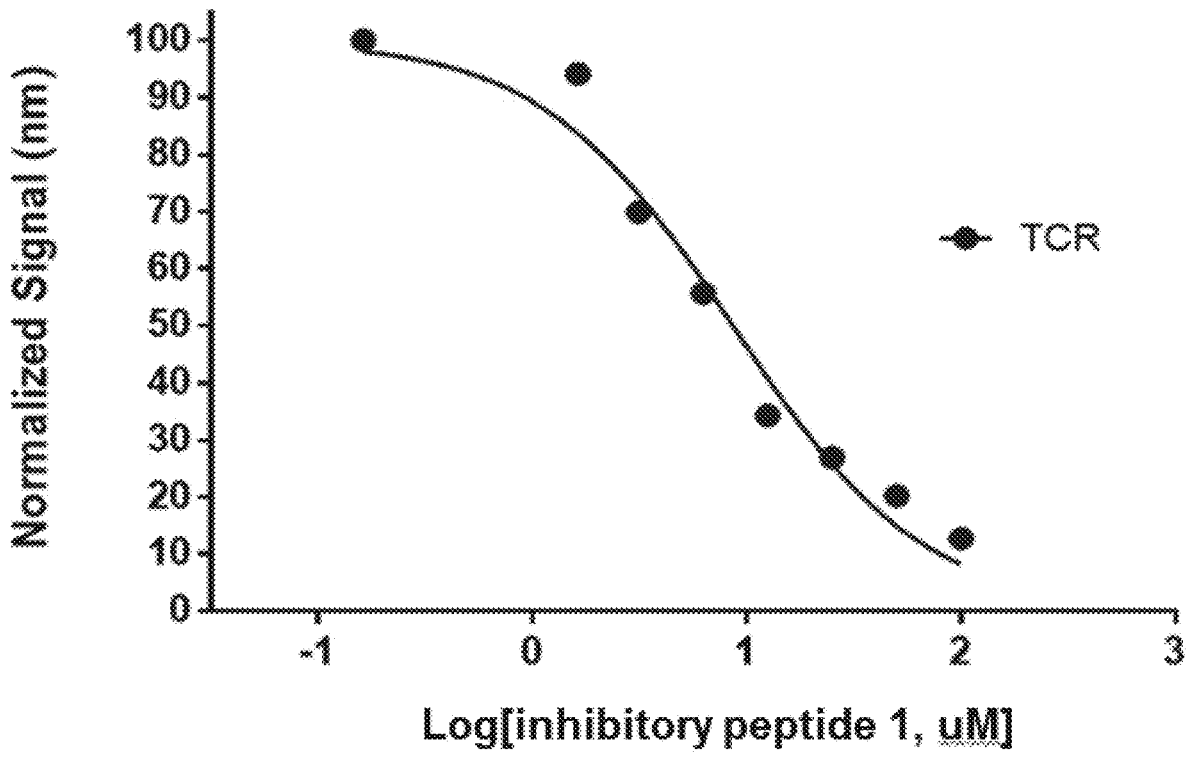
FIG. 5 is an exemplary competitive inhibition curve of TCR/Mage-A3 pMHC binding in the presence of varying concentrations of inhibitory peptide 1 (SEQ ID NO: 15) concentration.
FIG. 6 provides a comparison of the portion of the amino acid sequence of the Mage-A3 pMHC which binds to the Mage-A3 TCR and the portion of the amino acid sequence of inhibitory peptide 1 which binds to the Mage-A3 TCR.

Inhibition of Kinetic Binding for Soluble TCR to pMHC Using Inhibitory Peptide:

Inhibition of kinetic binding for soluble TCR to pMHC was measured using an ForteBio Octet RED96 instrument. Inhibitory peptide titrated in a 2-fold dilution series starting from 100 uM was first incubated with a constant concentration of 50 nM TCR (FIG. 5). Zero concentration of inhibitory peptide or zero concentration of TCR was used as a control. Biotinylated pMHC was captured on streptavidin biosensors. Sensors were quenched using excess biocytin and then baselined in buffer. Inhibitory peptide and TCR mixtures were associated onto the pMHC loaded biosensor. Association signal was monitored in real-time. Biosensors were then transferred to buffer and the dissociation signal was measured in real-time. Data was baseline corrected. The maximal association signal was normalized from 100% (0 nM inhibitory peptide control) to 0% (0 nM TCR control) and plotted versus log-scale inhibitory peptide concentration.

Example 6. Identifying the Inhibitory Peptide Bound to the TCR by Clonal Analysis (Phagemid And NGS)

Though numerous recombinant methods are possible, irrespective of display technique DNA sequencing is used to determine the encoded peptide candidate(s) of interest. Typically, systems are devised where the DNA (or RNA) is segregated physically to link genotype to the phenotype of target binding. Next step is to progress the previously target enriched clones into sequencing. Often the physically displayed peptides are tested in clonal isolation for their specific binding to the target of interest and often compared to a non-specific control. Clonal collections are grown segregated in 96-well format and then a phagemid ELISA assessment is utilized to determine the relevance of each clonal phagemid peptide-displayed sequence as a specific binder, non-binder, or non-specific binder. Specific binders are identified through this approach. Elements necessary for specific binding are identified and new binders with improved specificity or affinity are designed through expanded examination of collections of other specific binders. Comparison of the specific binders to non-specific binders also helps to identify and refine additional elements necessary for specific binding and for ways to improve specificity.

In yet another strategy to analyze recombinant clones, large collections of target-enriched clonal peptides sequences are compared against collections of peptide collections enriched to appropriate controls without performing any clonal physical binding assays to confirm their specificity by using Next Generation Sequencing (NGS) derived data. In this case the propensity for a clone to appear in a biased manner towards a target versus a control indirectly provides evidence of target specific binding. Furthermore, peptides similar to this highly biased sequence gives additional information towards additional peptides with similar properties. This compares to a manner similar to that described above that used ELISA assessment to concretely identify binders.

Still yet another strategy is to combine clonal ELISA analysis with broadened analysis through NGS-derived sequence collections.

In yet other methods discrete synthetic peptide coated beads are tested for binding and then directly sequenced for their peptide sequences.

Figure 8:
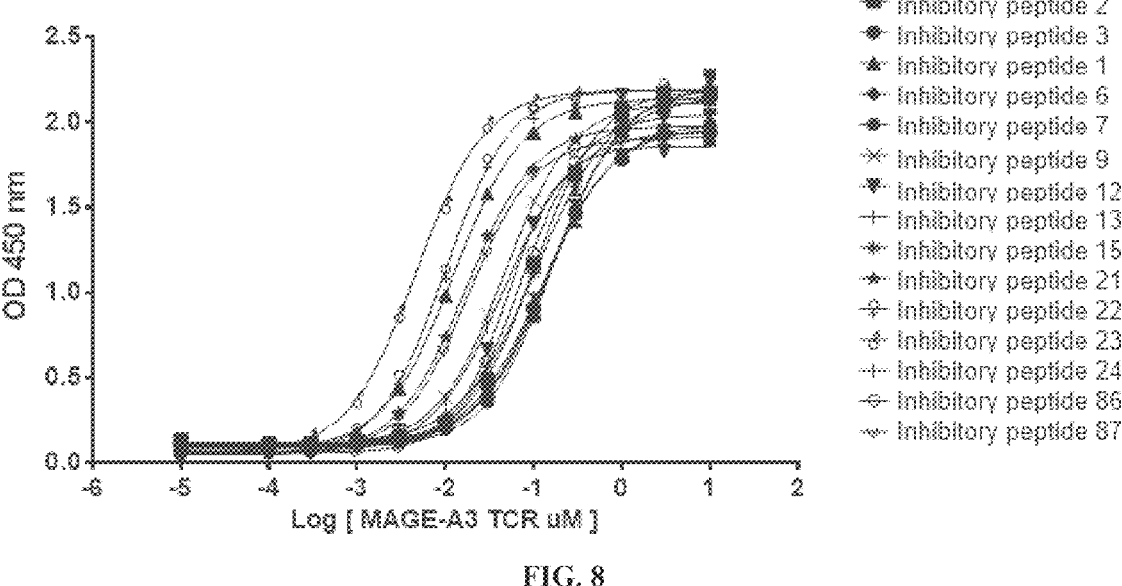
FIG. 8 illustrates peptide specificity MAGE-A3 TCR binding ELISA results.

Example 7. Synthetic Peptide Testing for MAGE-A3 TCR pMHC Competition by ELISA High binding plates were first coated with neutravidin. Neutravidin coated plates were blocked using bovine serum albumin in buffer and washed. Biotinylated inhibitory peptide at a single concentration of 100 nM was captured on neutravidin coated plates and washed. MAGE-A3-TCR was prepared in a half-log dilution series starting from 10 μM. MAGE-A3-TCR was then titrated onto the peptide captured plates for 1 hour and washed. A secondary horse radish peroxidase antibody conjugate that recognizes the MAGE-A3-TCR was then added to the plate at 1 μg/mL for 1 hour and washed. Plates were then developed using tetramethylbenzidine (TMB) for 5-10 min and stopped using acid. Absorbance at 450 nm was measured for each plate and plotted versus log-scale TCR concentration (FIG. 8). Biotinylated MAGE-A3 pMHC was used as a positive control. The concentration of MAGE-A3-TCR required to observe half maximal binding (EC50) was then calculated in Graphpad Prism 6.0 (FIGS. 10A-10B).

Figure 9:
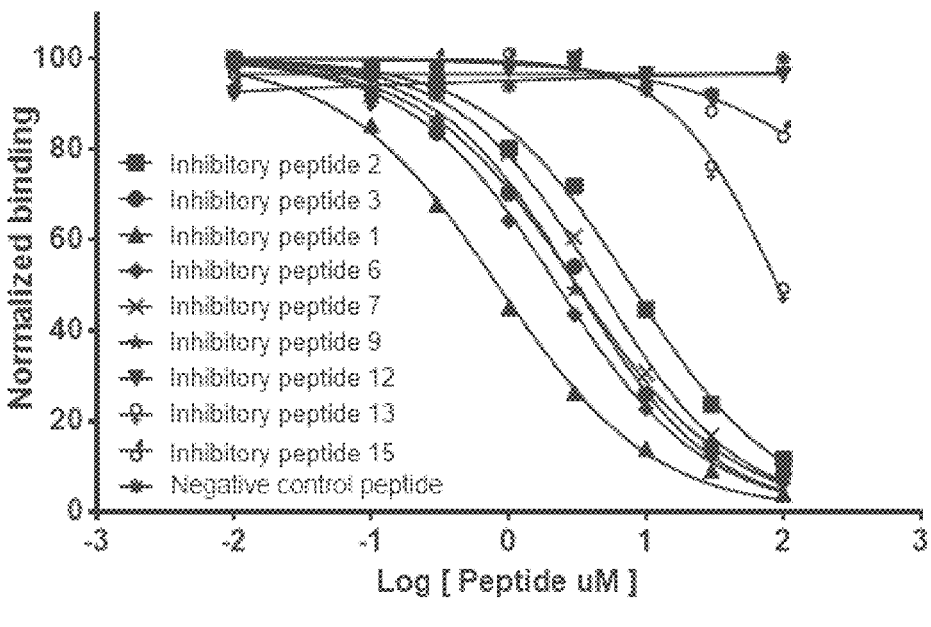
FIG. 9 illustrates peptide MAGE-A3 pMHC competition MAGE-A3 TCR binding ELISA results.

Inhibition of equilibrium binding for soluble MAGE-A3-TCR to MAGE-A3 pMHC was measured in an ELISA format. Briefly, high binding plates were first coated with neutravidin. Neutravidin coated plates were blocked using bovine serum albumin in buffer and washed. Biotinylated MAGE-A3 pMHC at a single concentration of 100 nM was captured on neutravidin coated plates, quenched using excess biocytin, and washed. Inhibitory peptide was titrated in a half-log dilution series starting from 100 uM and incubated with a constant concentration of 1 nM soluble MAGE-A3-TCR. Inhibitory peptide and TCR mixtures were then added to the pMHC captured plates for 30 min and washed. A secondary horse radish peroxidase antibody conjugate that recognizes the TCR was then added to the plate at 1 ug/mL for 30 min and washed. Plates were then developed using tetramethylbenzidine (TMB) for 5-10 min and stopped using acid. Absorbance at 450 nm was measured for each plate and normalized. The OD 450 nm signal was normalized from 100% (0 nM inhibitory peptide control) to 0% (0 nM TCR control) and plotted versus log-scale inhibitory peptide concentration (FIG. 5 and FIG. 9). Graphpad Prism 6.0 was used to calculate the inhibitory concentration of peptide required to achieve 50% maximal signal (IC50) (FIGS. 10A-10B).

Figure 11A:
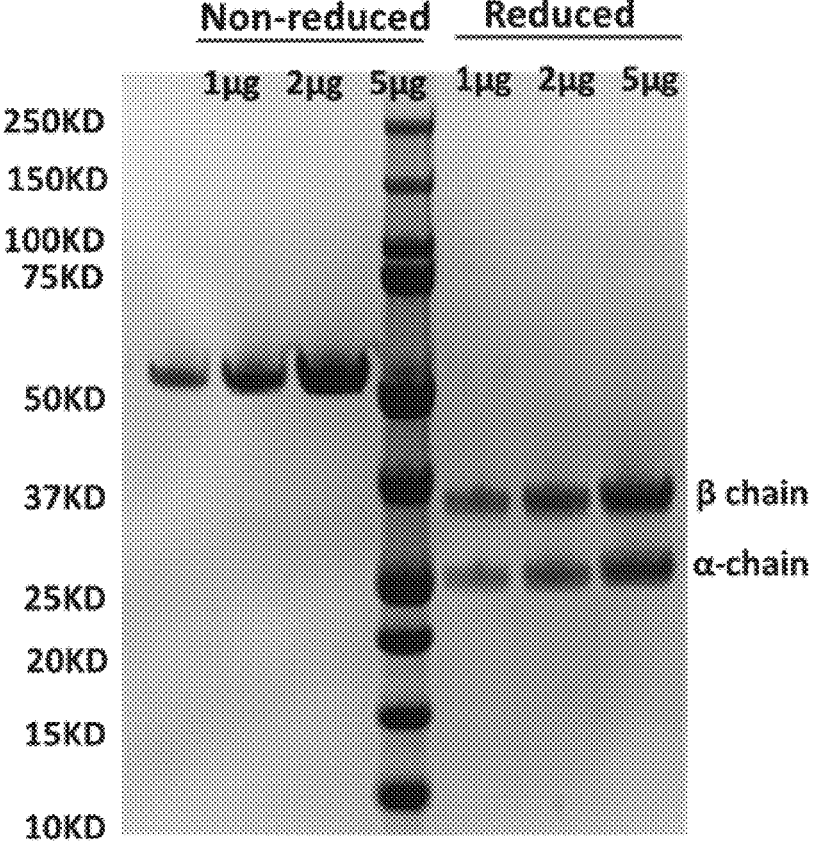
FIG. 11A-FIG. 11C illustrate analytical and functional characterization of a masked anti-MAGE-A3 soluble TCR where the mask is fused to the TCR beta subunit.
Figure 11B:
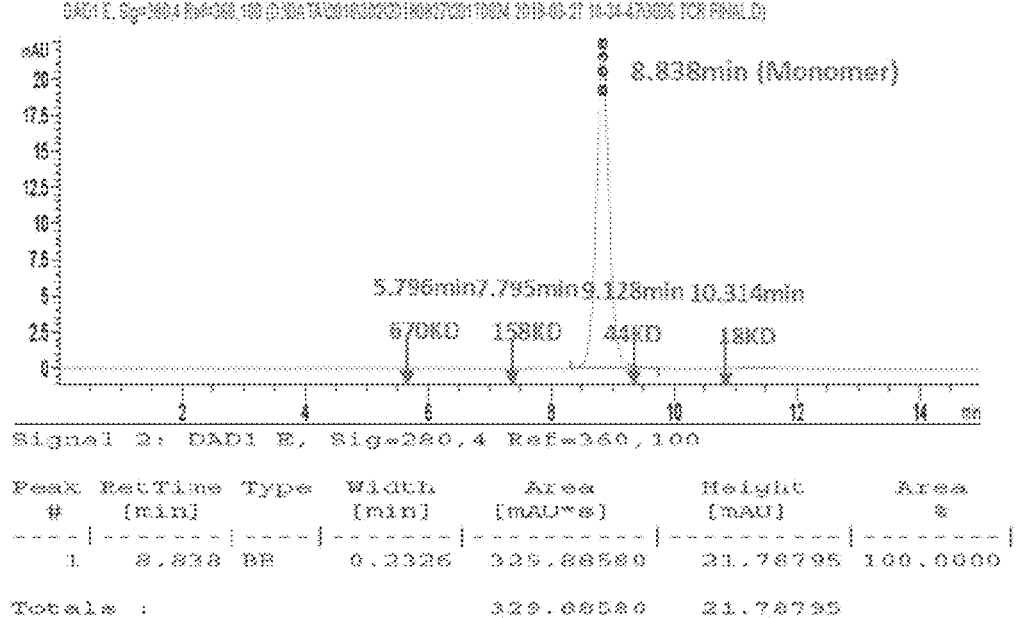
Figure 11C:
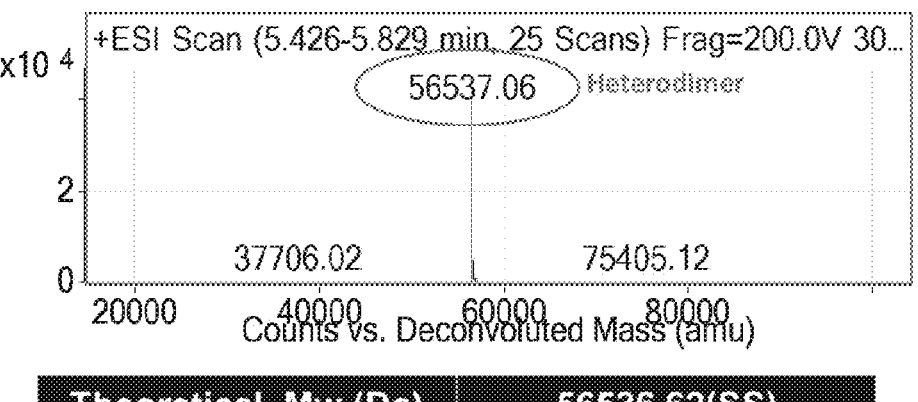
Figure 12A:
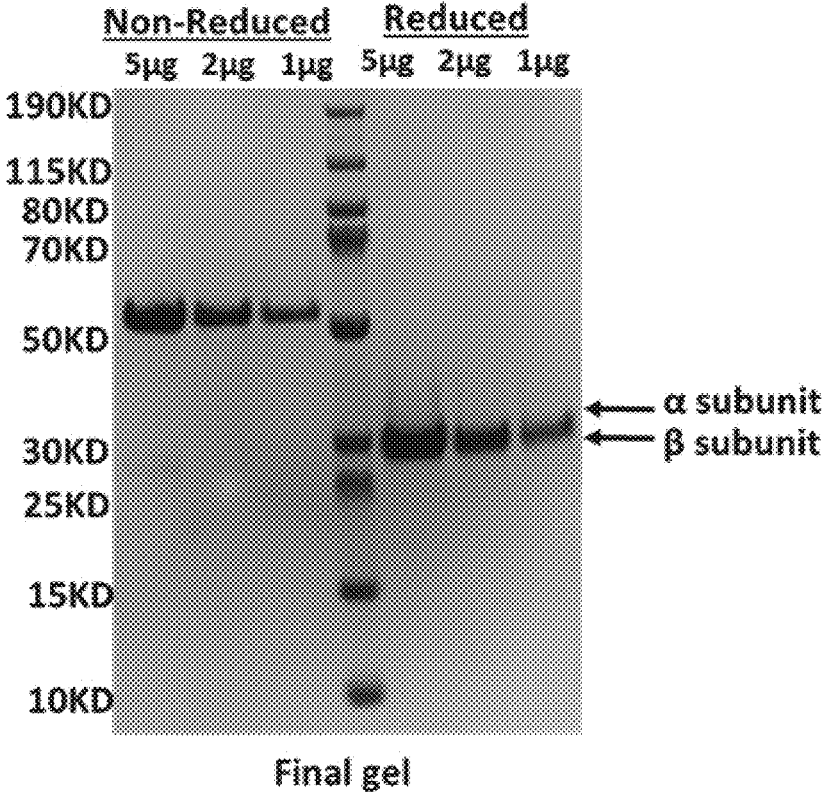
FIG. 12A-FIG. 12C illustrate analytical and functional characterization of a masked anti-MAGE-A3 soluble TCR where the mask is fused to the TCR alpha subunit.
Figure 12B:
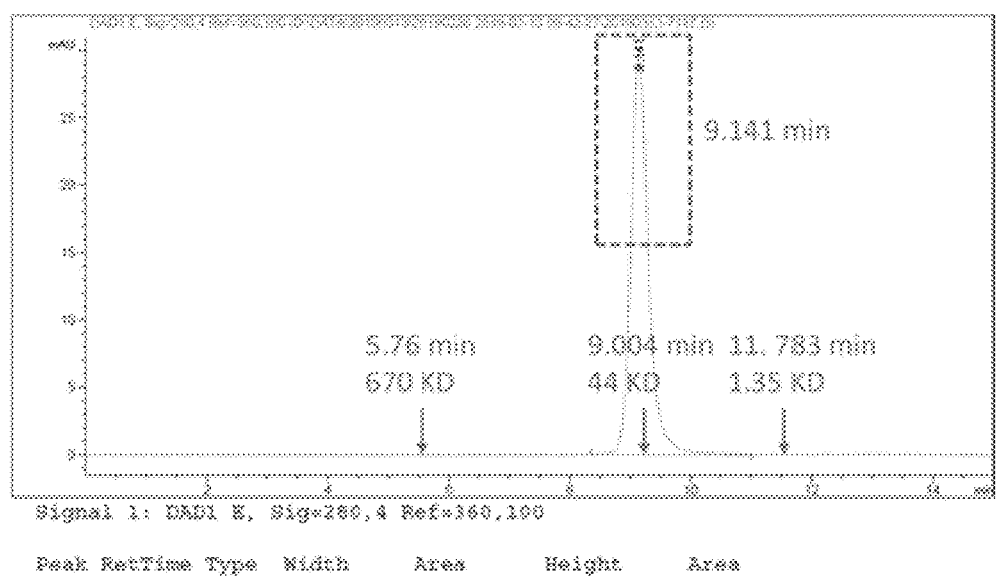
Figure 12C:
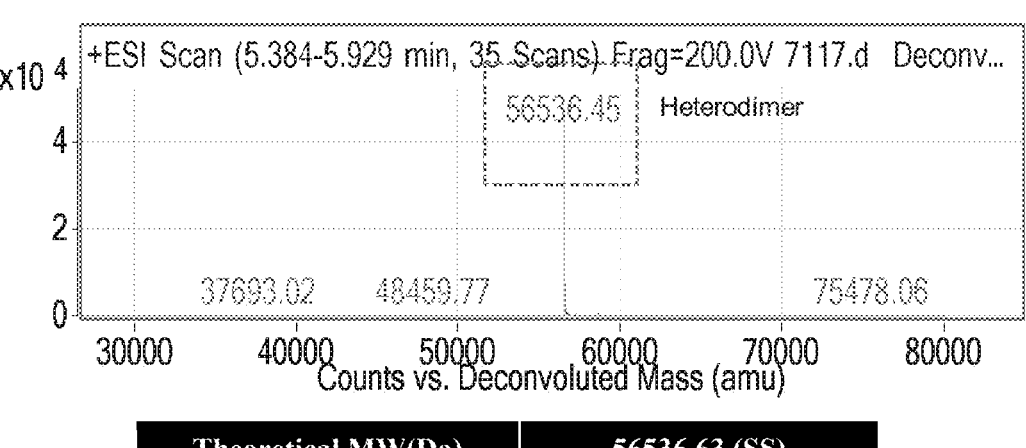

Example 8. Preparation and Characterization of Soluble Masked Anti-MAGE-A3 TCR Anti-MAGE-A3 sTCR was produced with a cleavable linker and Inhibitory peptide 1 fused to the N-terminus of the alpha or beta chain essentially as described in Example 2. The resulting masked soluble MAGE-A3 TCR (Sequences for masked MAGE-A3 TCR alpha and beta subunits are included in Table 2) was analyzed for biochemical integrity by SDS-PAGE analysis (FIG. 11A and FIG. 12A), size exclusion chromatography (FIG. 11B and FIG. 12B), and LC-MS analysis (FIG. 11C and FIG. 12C).

TABLE 2

MAGE-A3 TCR sequences

| Name | Sequence | SEQ ID NO: |
|---|---|---|
| MAGE-A3 alpha subunit | MKQEVTQIPAALSVPEGENLVLNCSFTDSAIYNLQ WFRQDPGKGLTSLLYVRPYQREQTSGRLNASLDKS SGRSTLYIAASQPGDSATYLCAVRPGGAGPFFVVF GKGTKLSVIPNIQNPDPAVYQLRDSKSSDKSVCLF TDFDSQTNVSQSKDSDVYITDKCVLDMRSMDFKSN SAVAWSNKSDFACANAFNNSIIPEDTFFPSPESSG GHHHHHHHH | 3 |
| MAGE-A3 beta subunit | MKAGVTQTPRYLIKTRGQQVTLSCSPISGHRSVSW YQQTPGQGLQFLFEYFSETQRNKGNFPGRFSGRQF SNSRSEMNVSTLELGDSALYLCASSFNMATGQYFG PGTRLTVTEDLKNVFPPEVAVFEPSEAEISHTQKA TLVCLATGFYPDHVELSWWVNGKEVHSGVCTDPQP LKEQPALNDSRYALSSRLRVSATFWQNPRNHFRCQ VQFYGLSENDEWTQDRAKPVTQIVSAEAWGRADGG GLNDIFEAQKIEWHE | 4 |
| MAGE-A3 alpha + Inhibitory peptide 1 fusion subunit | MGGVSCKDVYDEAFCWTGGGGSLSGRSDNHGSSGT KQEVTQIPAALSVPEGENLVLNCSFTDSAIYNLQW FRQDPGKGLTSLLYVRPYQREQTSGRLNASLDKSS GRSTLYIAASQPGDSATYLCAVRPGGAGPFFVVFG KGTKLSVIPNIQNPDPAVYQLRDSKSSDKSVCLFT DFDSQTNVSQSKDSDVYITDKCVLDMRSMDFKSNS AVAWSNKSDFACANAFNNSIIPEDTFFPSPESSGG HHHHHHHH | 5 |

TABLE 2-continued

MAGE-A3 TCR sequences

| Name | Sequence | SEQ ID NO: |
|---|---|---|
| MAGE-A3 beta + Inhibitory peptide 1 fusion subunit | MGGVSCKDVYDEAFCWTGGGGSLSGRSDNHGSSGT KAGVTQTPRYLIKTRGQQVTLSCSPISGHRSVSWY QQTPGQGLQFLFEYFSETQRNKGNFPGRFSGRQFS NSRSEMNVSTLELGDSALYLCASSFNMATGQYFGP GTRLTVTEDLKNVFPPEVAVFEPSEAEISHTQKAT LVCLATGFYPDHVELSWWVNGKEVHSGVCTDPQPL KEQPALNDSRYALSSRLRVSATFWQNPRNHFRCQV QFYGLSENDEWTQDRAKPVTQIVSAEAWGRADgGG LNDIFEAQKIEWHE | 6 |

Figure 13:
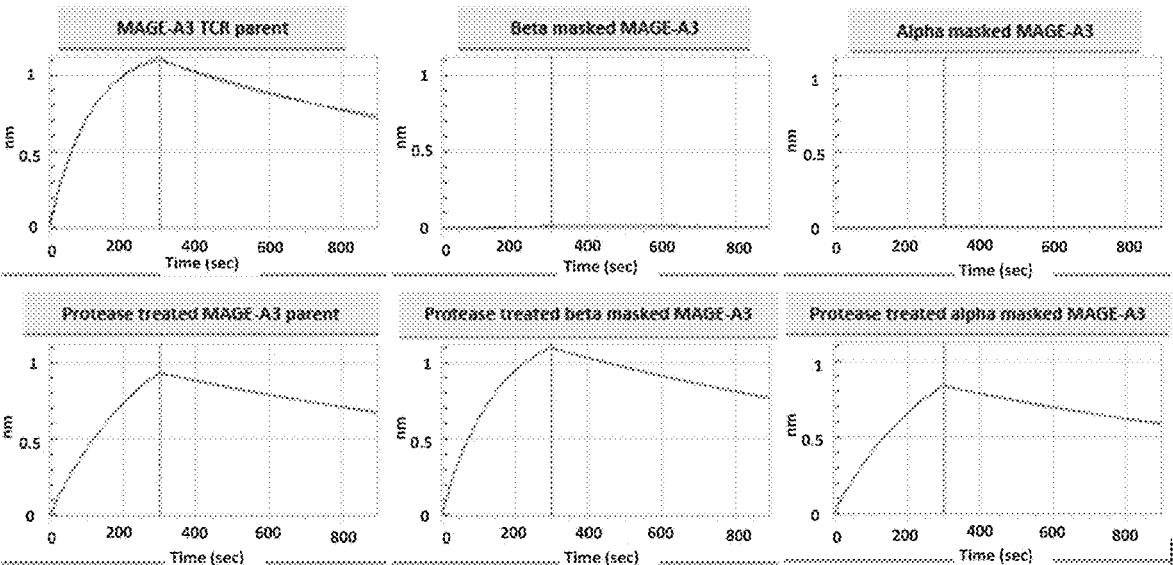
FIG. 13 illustrates the kinetic binding of masked anti-MAGE-A3 TCR to its cognate MAGE-A3 pMHC before and after urokinase treatment of the TCR.

Without being bound by theory, the results of these analyses provided supporting evidence for proper disulfide pairing and excellent biophysical properties of the reconstituted heterodimeric masked anti-MAGE-A3 TCR BLI based kinetic binding of masked anti-MAGE-A3 TCRs to the cognate MAGE-A3 pMHC was measured pre and post urokinase treatment of the TCR analogous to Example 5 (FIG. 13). Briefly, biotinylated pMHC was first captured on streptavidin biosensors. Sensors were quenched using excess biocytin and then baselined in buffer. TCRs were treated with recombinant urokinase overnight where indicated. TCRs were associated at 100 nM onto the pMHC loaded biosensor. Association signal was monitored in real-time. Biosensors were then transferred to buffer and the dissociation of TCR was measured in real-time. The results supported functional masking of a TCR using a inhibitory peptide fusion. While the fused peptide completely inhibits TCR recognition of its cognate pMHC, removal of the peptide fusion using a cleavable substrate and a relevant protease completely restored TCR functional binding to its cognate pMHC.

Figure 14:
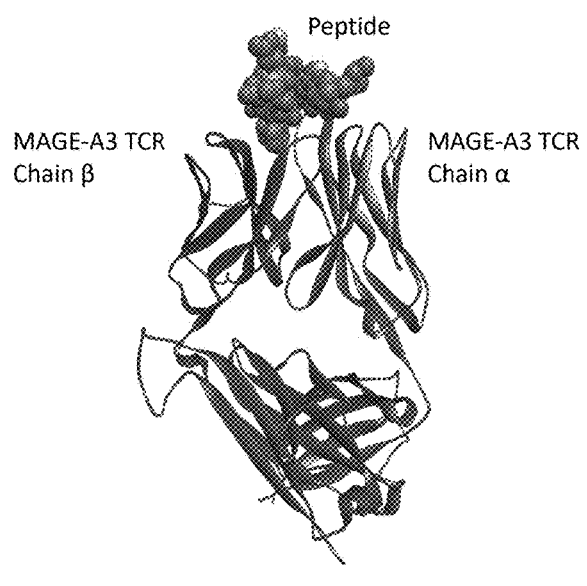
FIG. 14 illustrates an exemplary crystal structure of recombinant MAGE-A3 TCR and Inhibitory peptide 1 fusion.
Figure 15A:
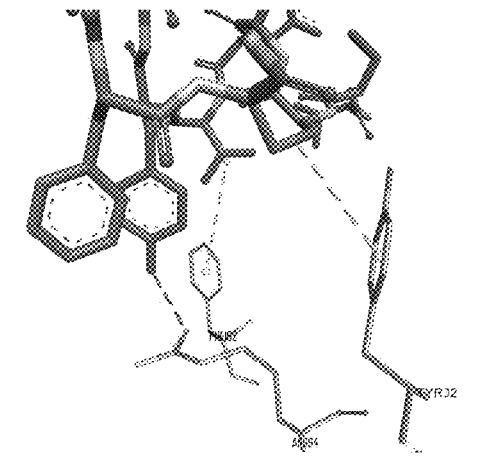
FIG. 15A-FIG. 15B illustrate specific peptide interactions of Inhibitory peptide 1 with the MAGE-A3 alpha and beta subunits.
Figure 15B:
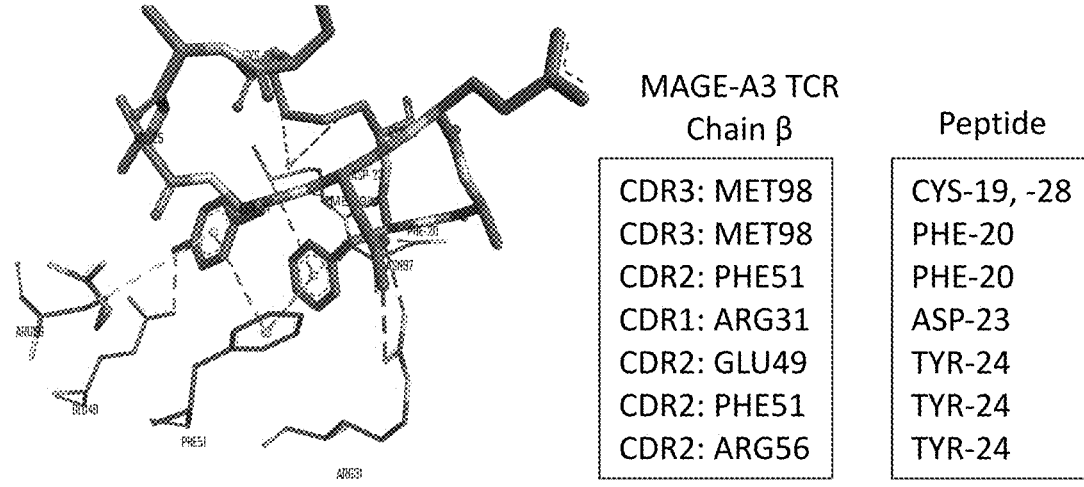

Example 9. Crystal Structure of Recombinant MAGE-A3 TCR. Inhibitory Peptide 1 Fusion Inhibitory peptide 1 was fused to MAGE-A3 TCR alpha chain separated by a linker. Protein was produced in a bacterial host system, refolded, and purified as described in Example 2. Purified peptide TCR fusion was then buffer exchanged in 20 mM Hepes and 150 mM NaCl pH 7 and concentrated to 9 mg/mL prior to crystallization screening. Peptide TCR fusion was crystalized using 15.5% PEG 3350 and 0.2 M NaNO3. Crystals were then harvested and frozen in 25% PEG 20% glycerol prior to analysis. A complete dataset was collected at the Advanced Light Source in Berkeley on BCSB beamline 5.0.2 from a single crystal. Data was processed using XDS software and scaled with the CCP4 suite to a resolution of 2.3 Å resolution. The space group is P21 with cell dimension: 64.45 114.53 80.70 90 113 90 and 2 molecules in the asymmetric unit. Structure was solved by molecular replacement (MR) with Phaser (CCP4) using chains D and E of the 5BRZ structural model (100% sequence homology with the target sequence). The MR search provided a unique solution with an initial Rfactor of 48.6%. Automatic fitting followed by manual rebuilding of the model and refinement in Refmac5 decreased the Rfactor/Rfree. At this point, clear density was visible for the cyclic peptide between the α and β subunits (FIG. 14). No clear density was visible for the flexible linker between the peptide and TCR alpha chain. The peptide sequence was built into the observed density and the model further refined to a final Rfactor/Rfree of 19.7%/25.7%. The expected disulfide bond was clearly visible between the two cystines of the peptide. Review of the resolved structure revealed specific interactions within the TCR CDR1, CDR2, and CDR3 domains and the conserved residues within the peptide sequence, Cys-19, Cys-28, Tyr-24, Asp-23, Phe-20, and Val-25. The peptide clearly forms specific interaction within the TCR CDR domains whose residues are responsible for the recognition of cognate MAGE-A3 pMHC antigen (FIG. 15A and FIG. 15B).

Example 10. Preparation and Panning of Soluble Anti-Gp100 TCRs

Figure 16A:
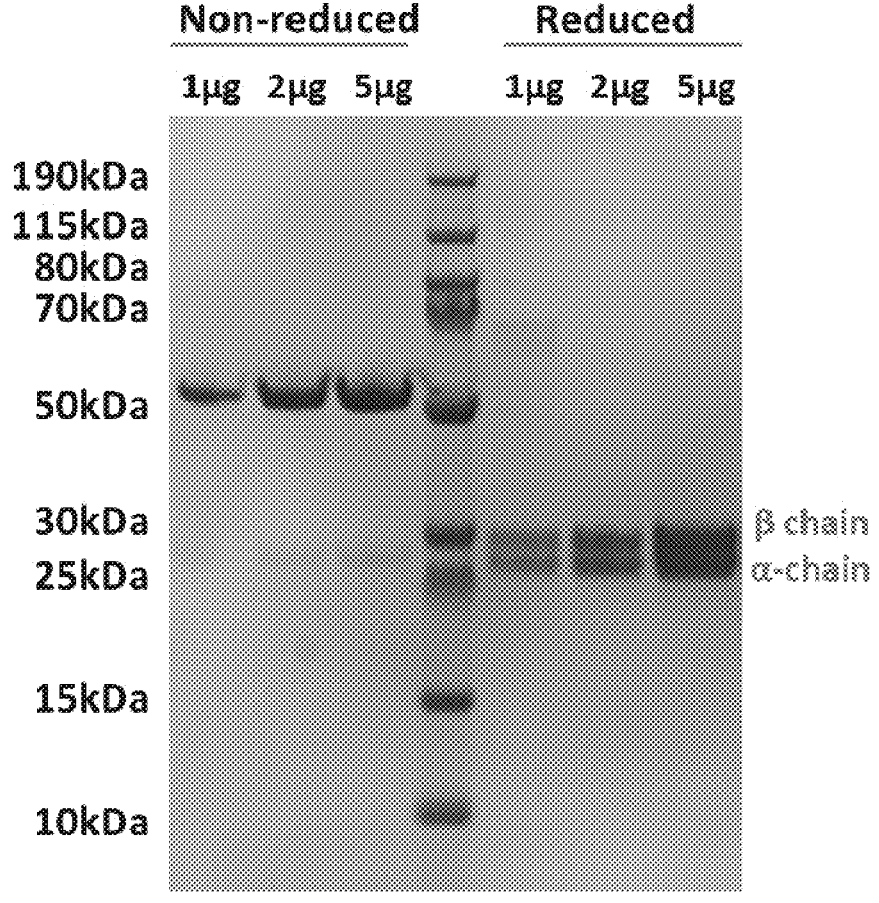
Figure 16B:
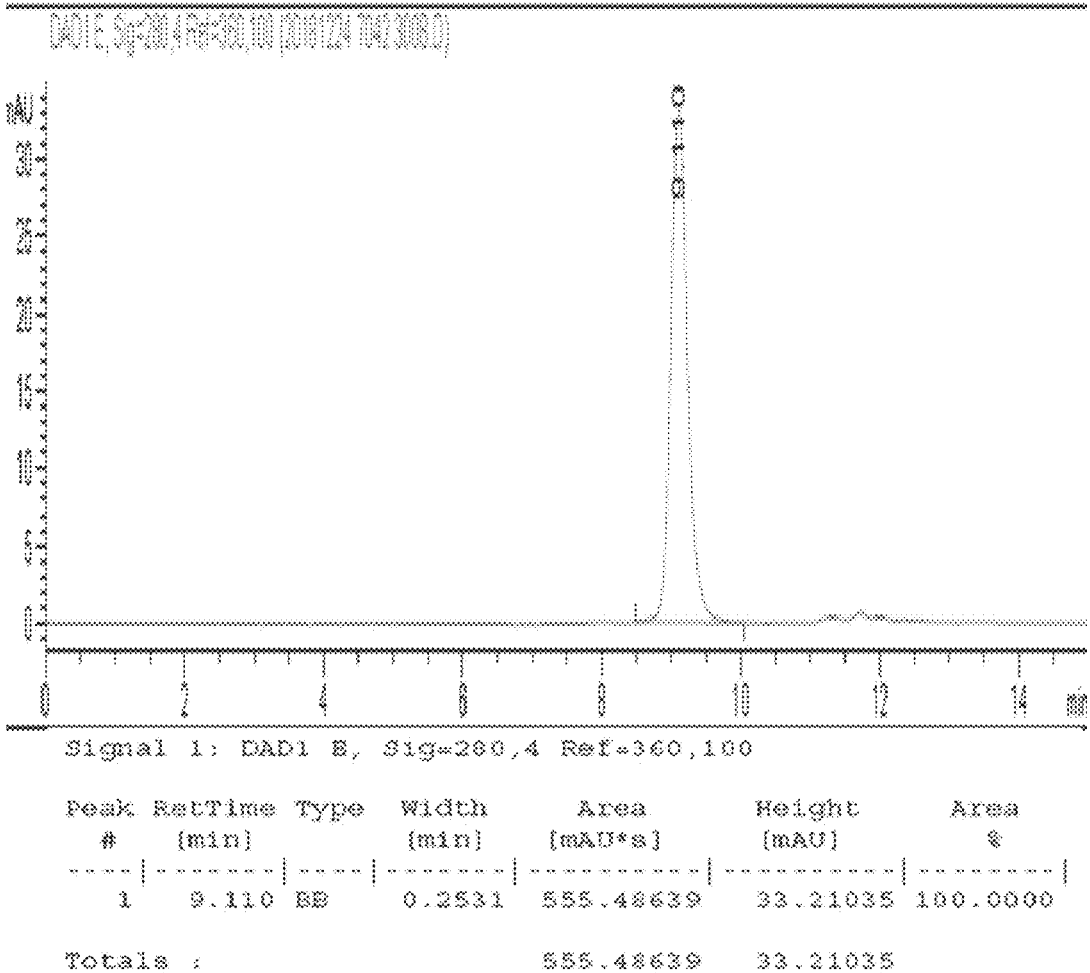

Anti-gp100 sTCR was produced as described in Example 2. The resulting soluble gp100 TCR (Sequences for gp100 alpha and beta subunits are included in Table 3) was analyzed for biochemical integrity by SDS-PAGE analysis (FIG. 16A), size exclusion chromatography (FIG. 16B), and LC-MS analysis (FIG. 16C).

TABLE 3 gp100 TCR sequences

| Name | Sequence | SEQ ID NO: |
|---|---|---|
| gp100 alpha subunit | MSQQGEEDPQALSIQEGENATMNCSYKTSINNLQW YRQNSGRGLVHLILIRSNEREKHSGRLRVTLDTSK KSSSLLITASRAADTASYFCATDGSTPMQFGKGTR LSVIANIQKPDPAVYQLRDSKSSDKSVCLFTDFDS QTNVSQSKDSDVYITDKCVLDMRSMDFKSNSAVAW SNKSDFACANAFNNSIIPEDTFFPSPESSGGHHHH HHHH | 7 |
| gp100 beta subunit | MDGGITQSPKYLFRKEGQNVTLSCEQNLNHDAMYW YRQDPGQGLRLIYYSWAQGDFQKGDIAEGYSVSRE KKESFPLTVTSAQKNPTAFYLCASSWGAPYEQYFG PGTRLTVTEDLKNVFPPEVAVFEPSEAEISHTQKA TLVCLATGFYPDHVELSWWVNGKEVHSGVCTDPQP LKEQPALNDSRYALSSRLRVSATFWQDPRNHFRCQ VQFYGLSENDEWTQDRAKPVTQIVSAEAWGRADGG GLNDIFEAQKIEWHE | 8 |

Figures 16D, 16E:
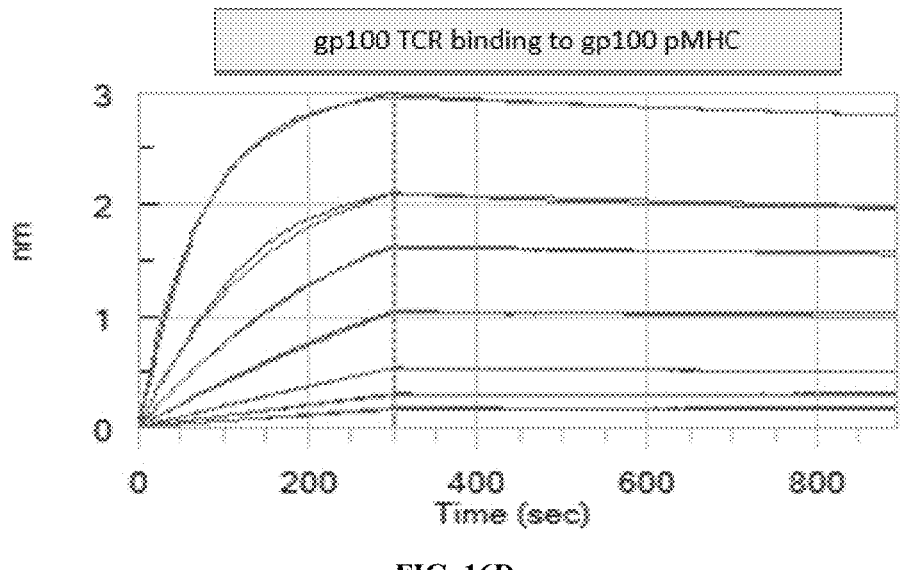
Figure 18:
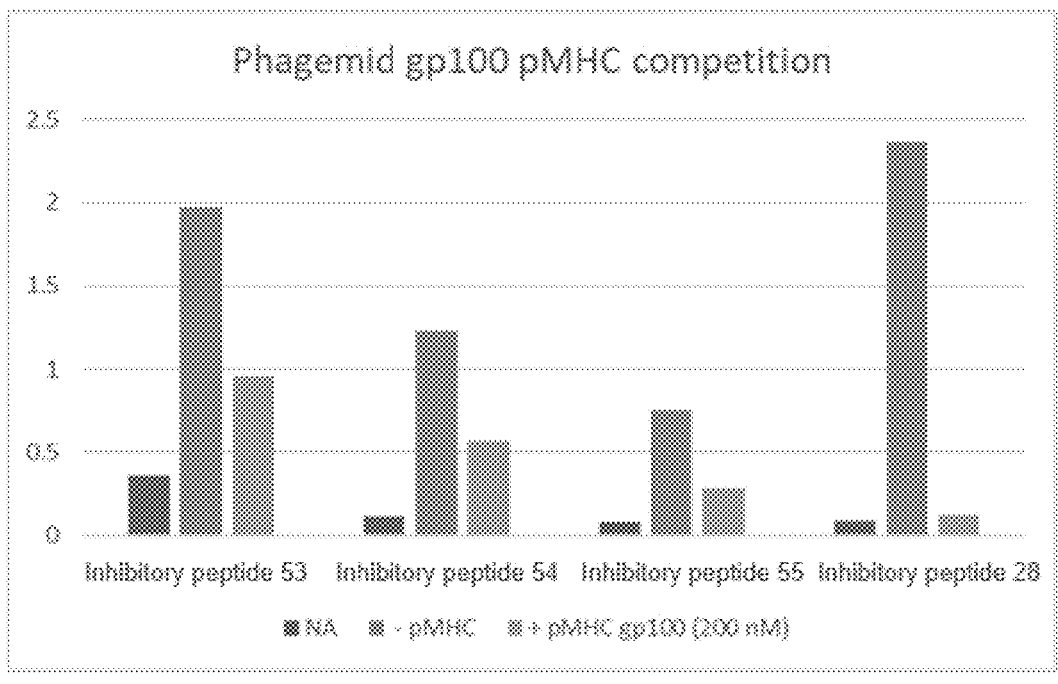
FIG. 18 illustrates phagemid competition binding to gp100 TCR with gp100 pMHC.

The results of these analyses provided supporting evidence for proper disulfide pairing and excellent biophysical properties of the reconstituted heterodimeric anti-gp100 TCR. After the gp100 sTCR was enzymatically biotinylated it was further tested by kinetic binding of gp100 TCR to its cognate gp100 pMHC (and as indicated), and $K_D$, $k_{on}$, and $k_{off}$ were calculated (FIG. 16D and FIG. 16E) essentially as described in Example 3. Following protein analysis, the biotinylated gp100 sTCR was used for biopanning essentially as also described above in Example 1 to pan p3 and p8 phagemid peptide display libraries. Following 2-4 rounds of panning individual phagemid expressing clonal isolates were tested, as described in Example 4, for binding to gp100 sTCR by phagemid ELISA. Phagemid results are summarized in FIGS. 17A-17B. Next, select phage clones were tested for pMHC competition and results graphed (FIG. 18).

Example 11. Synthetic Peptide Testing for gp100 TCR Binding by ELISA

Figure 19:
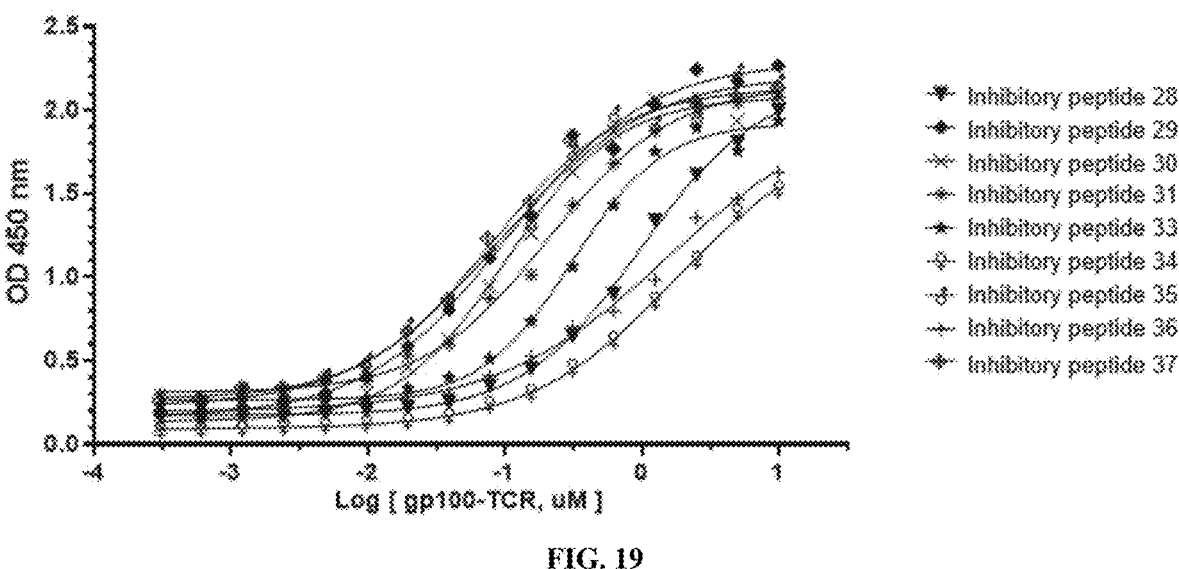
FIG. 19 illustrates by ELISA binding gp100 TCR binding to synthetic peptides.

Select peptides were selected following sequence identification and/or functional phage testing for chemical synthesis. Resulting peptides were tested for TCR binding by ELISA (FIG. 19), as described in Example 7 and their calculated EC50 values along with sequence identities are summarized in FIG. 20.

Example 12. Preparation and Panning of Soluble Anti-HIV TCR

Figure 21A:
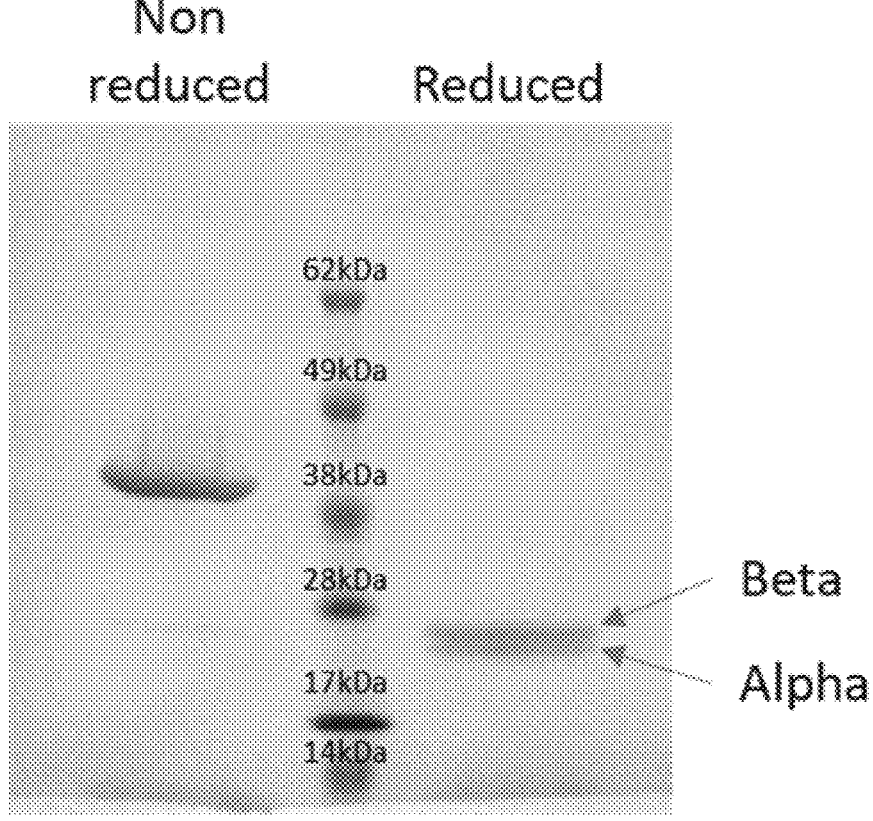
FIG. 21A-FIG. 21C illustrate analytical and functional characterization of a functional HIV soluble TCR.
Figures 21B, 21C:
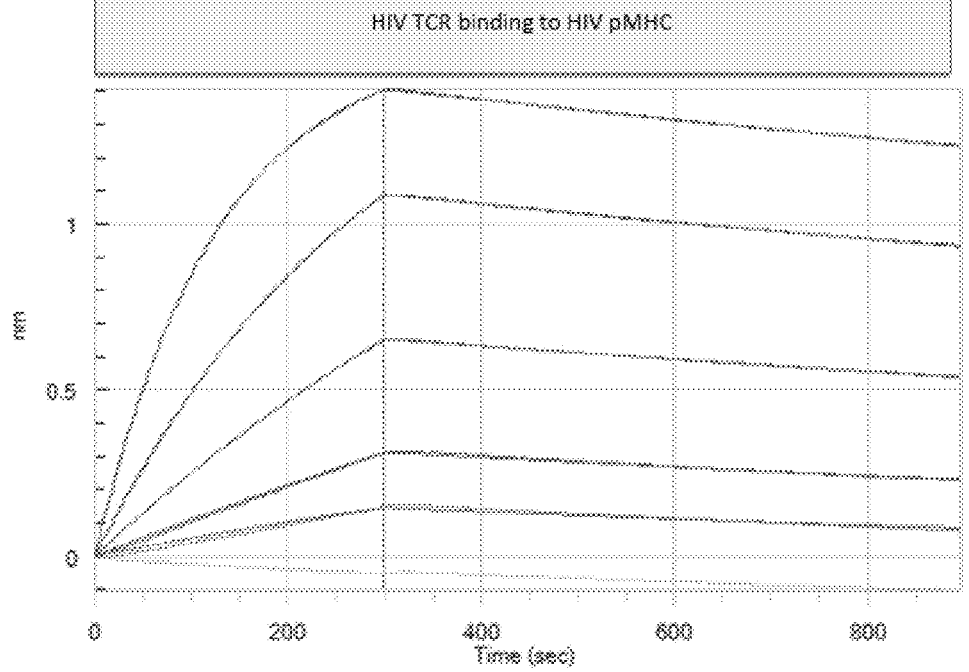

Anti-HIV TCR was produced as described in Example 2 above. The resulting soluble HIV TCR (Sequences for HIV alpha and beta subunits are included in Table 4) was analyzed for biochemical integrity by SDS-PAGE analysis (FIG. 21A) and after the HIV TCR was enzymatically biotinylated it was further tested by kinetic binding of HIV TCR to its cognate HIV pMHC (and as indicated), and $K_D$, $k_{on}$, and $k_{off}$ were calculated (FIG. 21B and FIG. 21C) essentially as described in Example 3.

TABLE 4

HIV TCR sequences

| Name | Sequence | SEQ ID NO: |
|---|---|---|
| HIV TCR alpha subunit | MQKEVEQNSGPLSVPEGAIASLNCTYSDRGSQSFF WYRQYSGKSPELIMFIYSNGDKEDGRFTAQLNKAS QYISLLIRDSKLSDSATYLCAVRGAHDYALNFGKG TSLLVTPHIQKPDPAVYQLRDSKSSDKSVCLFTDF DSQTNVSQSKDSDVYITDKCVLDMRSMDFKSNSAV AWSNKSDFACANAFNNSIIPEDTFFPSPESSGGHH HHHHHH | 9 |
| HIV TCR beta subunit | MEAGVTQSPTHLIKTRGQQVTLRCSPKSGHDTVSW YQQALGQGPQFIFQYALGEERQRGNFPDRFSGHQF PNYSSELNVNALLLGDSALYLCASSDTVSYEQYFG PGTRLTVTEDLKNVFPPEVAVFEPSEAEISHTQKA TLVCLATGFYPDHVELSWWVNGKEVHSGVCTDPQP LKEQPALNDSRYALSSRLRVSATFWQDPRNHFRCQ VQFYGLSENDEWTQDRAKPVTQIVSAEAWGRADGG GLNDIFEAQKIEWHE | 10 |

Following protein analysis, the biotinylated HIV TCR was used for biopanning essentially as described in Example 1 to pan p3 and p8 phagemid peptide display libraries. Following 2-4 rounds of panning individual phagemid expressing clonal isolates were tested for binding specificity to HIV TCR by phagemid ELISA as described in Example 4 and results summarized (FIGS. 22A-22B).

Figure 23A:
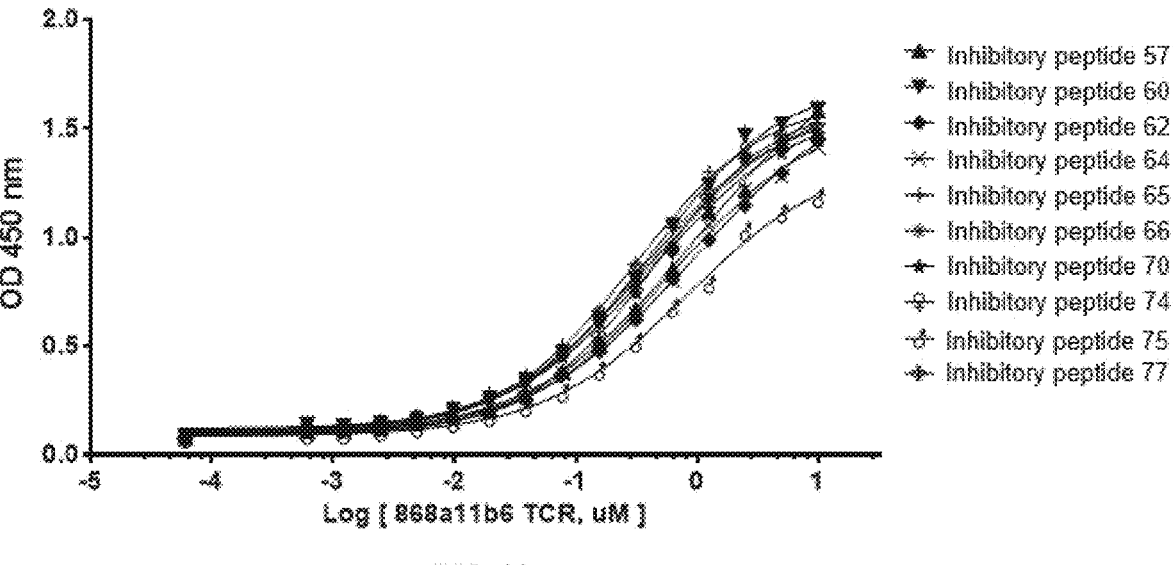
FIG. 23A-FIG. 23B illustrate synthetic peptide TCR binding and pMHC competition with HIV pMHC.
Figure 23B:
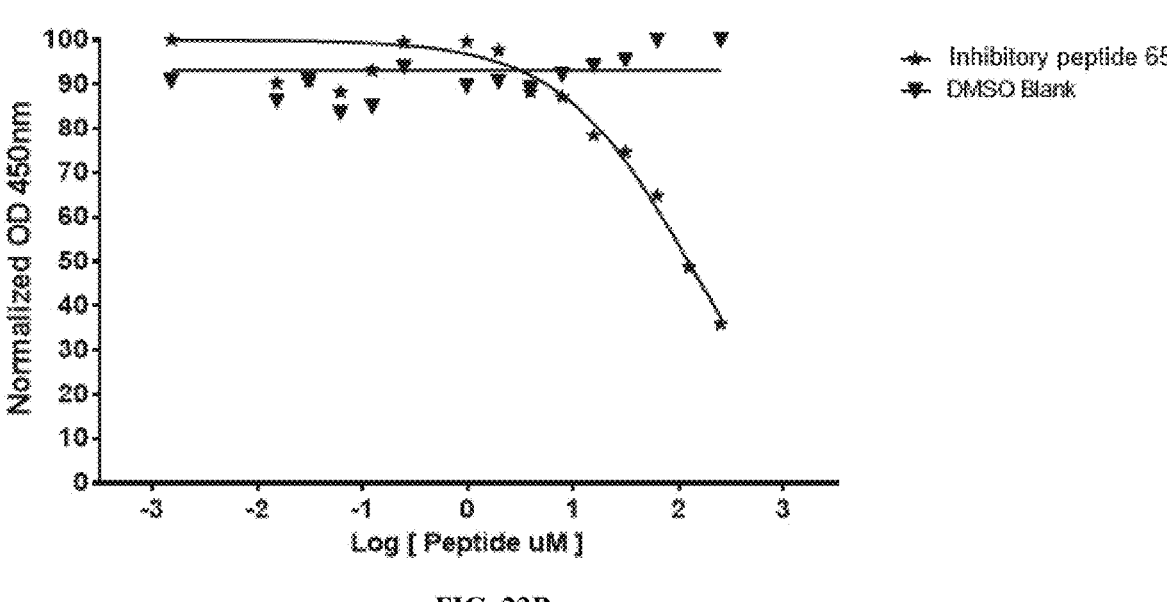

Example 13. Synthetic Peptide Testing for HIV TCR Binding and DMHC Competition by ELISA and Kinetic Analysis Select peptides were chosen following sequence identification. Resulting peptides were tested as described in Example 7 for TCR binding by ELISA (FIG. 23A), and calculated EC50 values along with sequence identities for each of the peptides are found in FIGS. 24A-24B. Next peptides were tested by ELISA to determine their capacity to inhibit HIV pMHC binding to anti-HIV TCR binding (FIG. 23B). Calculated IC50 values and sequence identities are found in FIGS. 24A-24B.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Certain Embodiments

Embodiment 1 provides a method of inhibiting an interaction of a T cell receptor (TCR) with a peptide-major histocompatibility (pMHC) complex, the method comprising administering to a TCR an inhibitory peptide that binds to the TCR without the aid of a MHC, thereby inhibiting the interaction of the TCR with a pMHC complex.

Embodiment 2 provides the method of embodiment 1, wherein the inhibitory peptide is a peptide derived from a non-native antigen.

Embodiment 3 provides the method of embodiment 1, wherein the inhibitory peptide is not identical to a peptide of peptide-major histocompatibility complex (pMHC).

Embodiment 4 provides the method of embodiment 1, wherein the inhibitory peptide is a non-human antigen.

Embodiment 5 provides the method of embodiment 1, wherein the inhibitory peptide comprises a viral peptide sequence, bacterial peptide sequence, or a fungal peptide sequence.

Embodiment 6 provides the method of embodiment 1, wherein the inhibitory peptide is from a peptide library.

Embodiment 7 provides the method of embodiment 6, wherein the peptide library is a random peptide library.

Embodiment 8 provides the method of any one of embodiments 1-7, wherein the inhibitory peptide has at least 5 amino acids.

Embodiment 9 provides the method of any one of embodiments 1-8, wherein the inhibitory peptide has at least 8 amino acids.

Embodiment 10 provides the method of any one of embodiments 1-9, wherein the inhibitory peptide has at least 10 amino acids.

Embodiment 11 provides the method of any one of embodiments 1-10, wherein the inhibitory peptide has at least 12 amino acids.

Embodiment 12 provides the method of any one of embodiments 1-11, wherein the inhibitory peptide has at least 15 amino acids.

Embodiment 13 provides the method of any one of embodiments 1-12, wherein the inhibitory peptide has at least 18 amino acids.

Embodiment 14 provides the method of any one of embodiments 1-13, wherein the inhibitory peptide has no more than 30 amino acids.

Embodiment 15 provides the method of any one of embodiments 1-14, wherein the inhibitory peptide binds to the TCR at or near a complementarity-determining region (CDR) of the TCR.

Embodiment 16 provides the method of any one of embodiments 1-15, wherein the inhibitory peptide binds to an alpha extracellular domain of the TCR Embodiment 17 provides the method of any one of embodiments 1-16, wherein the inhibitory peptide binds to a beta extracellular domain of the TCR Embodiment 18 provides the method of any one of embodiments 1-17, wherein the inhibitory peptide binds to an alpha extracellular domain of the TCR and a beta extracellular domain of the TCR Embodiment 19 provides the method of any one of embodiments 1-18, wherein the inhibitory peptide binds to the TCR through ionic interactions, electrostatic interactions, hydrophobic interactions, Pi-stacking interactions, and H-bonding interactions, or a combination thereof.

Embodiment 20 provides the method of any one of embodiments 1-19, wherein the binding of the inhibitory peptide to the TCR sterically blocks the interaction of the TCR with a pMHC complex.

Embodiment 21 provides the method of any one of embodiments 1-20, wherein the inhibitory peptide is a linear or a cyclic peptide.

Embodiment 22 provides the method of any one of embodiments 1-21, wherein the inhibitory peptide comprises a modified amino acid, a non-natural amino acid, a modified non-natural amino acid, or combination thereof.

Embodiment 23 provides the method of embodiment 22, wherein the modified amino acid or modified non-natural amino acid comprises a post-translational modification.

Embodiment 24 provides the method of any one of embodiments 1-23, wherein the inhibitory peptide comprises an alkyne or dibenzocyclooctyne modified amino acid for reacting with an azide functionalized molecule.

Embodiment 25 provides the method of any one of embodiments 1-23, wherein the inhibitory peptide comprises a trans-cyclooctene, vinyl, or methylcyclopropene modified amino acid for reacting with a tetrazine functionalized molecule.

Embodiment 26 provides the method of any one of embodiments 1-25, wherein the inhibitory peptide comprises the amino acid sequence of VSCKDVYDEAFCW (SEQ ID NO: 2).

Embodiment 27 provides the method of any one of embodiments 1-26, wherein the TCR is expressed on a surface of the T cell.

Embodiment 28 provides the method of any one of embodiments 1-26, wherein the TCR is a soluble TCR.

Embodiment 29 provides the method of any one of embodiments 1-26, wherein the TCR is an engineered TCR.

Embodiment 30 provides the method of any one of embodiments 1-29, wherein the TCR is a Mage-A3 TCR Embodiment 31 provides the method of any one of embodiments 1-30, wherein the TCR comprises a TCR alpha extracellular domain and a TCR beta extracellular domain.

Embodiment 32 provides the method of embodiment 31, wherein the TCR alpha extracellular domain comprises a mutation to increase binding affinity of the TCR to the inhibitory peptide.

Embodiment 33 provides the method of embodiment 31, wherein the TCR alpha extracellular domain comprises a mutation to increase stability of the TCR Embodiment 34 provides the method of embodiment 31, wherein the TCR beta extracellular domain comprises a mutation to increase binding affinity of the TCR to the inhibitory peptide.

Embodiment 35 provides the method of embodiment 31, wherein the TCR beta extracellular domain comprises a mutation to increase stability of the TCR Embodiment 36 provides the method of embodiment 31, wherein the TCR alpha extracellular domain comprises a mutation to increase binding affinity of the TCR to the pMHC complex.

Embodiment 37 provides the method of embodiment 31, wherein the TCR beta extracellular domain comprises a mutation to increase binding affinity of the TCR to the pMHC complex.

Embodiment 38 provides a method of identifying a peptide that binds to a T cell receptor (TCR) without the aid of a MHC, the method comprising: (a) incubating a peptide from a peptide library and a TCR in a suitable medium at a neutral pH, wherein the peptide from the peptide library is expressed on a surface of a cell or a phage; (b) removing non-binding peptides by washing the medium at a neutral pH; (c) eluting the peptide that is bound to the TCR by altering the pH to an acidic pH, or a basic pH; and (d) identifying the peptide that is bound to the TCR without the aid of a MHC by sequencing DNA of the cell or the phage on which the peptide is expressed.

Embodiment 39 provides the method of embodiment 38, wherein the neutral pH is from 7.0 to 7.8.

Embodiment 40 provides the method of embodiment 39, wherein the neutral pH is 7.4.

Embodiment 41 provides the method of any one of embodiments 38-40, wherein the acidic pH is from 2.0 to 5.0.

Embodiment 42 provides the method of embodiment 41, wherein the acidic pH is 2.2.

Embodiment 43 provides the method of any one of embodiments 38-40, wherein the basic pH is from 9.0 to 11.5.

Embodiment 44 provides the method of embodiment 43, wherein the basic pH is 11.0.

Embodiment 45 provides the method of any one of embodiments 38-44, wherein steps (a)-(c) are repeated at least one time prior to step (d).

Embodiment 46 provides the method of any one of embodiments 38-44, wherein steps (a)-(c) are repeated at least two times prior to step (d).

Embodiment 47 provides the method of any one of embodiments 38-44, wherein steps (a)-(c) are repeated at least three times prior to step (d).

Embodiment 48 provides the method of any one of embodiments 38-47, wherein the peptide library is a phagemid peptide library.

Embodiment 49 provides the method of any one of embodiments 38-47, wherein the peptide of step (a) is expressed on a surface of an *E. coli* cell.

Embodiment 50 provides the method of any one of embodiments 38-47, wherein the peptide of step (a) is expressed on a surface of a yeast cell.

Embodiment 51 provides the method of any one of embodiments 38-47, wherein the peptide of step (a) is expressed on a surface of a phage.

Embodiment 52 provides the method of any one of embodiments 38-51, wherein the peptide is derived from a non-native antigen.

Embodiment 53 provides the method of any one of embodiments 38-51, wherein the peptide is not identical to a peptide of a peptide-major histocompatibility complex (pMHC).

Embodiment 54 provides the method of any one of embodiments 38-51, wherein the peptide is a non-human antigen.

Embodiment 55 provides the method of any one of embodiments 38-51, wherein the peptide comprises a viral peptide sequence, bacterial peptide sequence, or a fungal peptide sequence.

Embodiment 56 provides the method of embodiment 38, wherein the peptide library is a random peptide library.

Embodiment 57 provides the method of any one of embodiments 38-56, wherein the peptide has at least 5 amino acids.

Embodiment 58 provides the method of any one of embodiments 38-57, wherein the peptide has at least 8 amino acids.

Embodiment 59 provides the method of any one of embodiments 38-58, wherein the peptide has at least 10 amino acids.

Embodiment 60 provides the method of any one of embodiments 38-59, wherein the peptide has at least 12 amino acids.

Embodiment 61 provides the method of any one of embodiments 38-60, wherein the peptide has at least 15 amino acids.

Embodiment 62 provides the method of any one of embodiments 38-61, wherein the peptide has at least 18 amino acids.

Embodiment 63 provides the method of any one of embodiments 38-62, wherein the peptide has no more than 30 amino acids.

Embodiment 64 provides the method of any one of embodiments 38-63, wherein the peptide binds to the TCR at or near a complementarity-determining region (CDR) of the TCR Embodiment 65 provides the method of any one of embodiments 38-64, wherein the peptide binds to an alpha extracellular domain of the TCR Embodiment 66 provides the method of any one of embodiments 38-64, wherein the peptide binds to a beta extracellular domain of the TCR.

Embodiment 67 provides the method of any one of embodiments 38-64, wherein the peptide binds to an alpha extracellular domain of the TCR and a beta extracellular domain of the TCR.

Embodiment 68 provides the method of any one of embodiments 38-67, wherein the peptide binds to the TCR through ionic interactions, electrostatic interactions, hydrophobic interactions, Pi-stacking interactions, and H-bonding interactions, or a combination thereof.

Embodiment 69 provides the method of any one of embodiments 38-68, wherein the peptide is a linear or a cyclic peptide.

Embodiment 70 provides the method of any one of embodiments 38-69, wherein the peptide comprises a modified amino acid, a non-natural amino acid, a modified non-natural amino acid, or combination thereof.

Embodiment 71 provides the method of embodiment 70, wherein the modified amino acid or modified non-natural amino acid comprises a post-translational modification.

Embodiment 72 provides the method of any one of embodiments 38-71, wherein the peptide comprises an alkyne or dibenzocyclooctyne modified amino acid for reacting with an azide functionalized molecule.

Embodiment 73 provides the method of any one of embodiments 38-71, wherein the peptide comprises a transcyclooctene, vinyl, or methylcyclopropene modified amino acid for reacting with a tetrazine functionalized molecule.

What is claimed is:

1. A method of inhibiting an interaction of a T cell receptor (TCR) with a peptide-major histocompatibility (pMHC) complex, the method comprising administering to the TCR and the pMHC an inhibitory peptide that binds to the TCR without the aid of a MHC, thereby inhibiting the interaction of the TCR with the pMHC complex, wherein the TCR comprises a TCR alpha extracellular domain comprising a variable region of the alpha extracellular domain of the TCR and a TCR beta extracellular domain comprising a variable region of the beta extracellular domain of the TCR, wherein the TCR is a Mage-A3 TCR, and wherein the inhibitory peptide comprises an amino acid sequence according to any one of SEQ ID NOs: 11, 12, 15, 16, 17, 19, 22, 23, and 25.

2. The method of claim 1, wherein the Mage-A3 TCR comprises an alpha domain comprising an amino acid sequence of SEQ ID NO: 3 and the Mage-A3 TCR comprises a beta domain comprising an amino acid sequence of SEQ ID NO: 4.

3. A method of inhibiting an interaction of a T cell receptor (TCR) with a peptide-major histocompatibility (pMHC) complex, the method comprising administering to the TCR and the pMHC an inhibitory peptide that binds to the TCR without the aid of a MHC, thereby inhibiting the interaction of the TCR with the pMHC complex, wherein the TCR comprises a TCR alpha extracellular domain comprising a variable region of the alpha extracellular domain of the TCR and a TCR beta extracellular domain comprising a variable region of the beta extracellular domain of the TCR; and wherein the TCR is a gp100 TCR, and wherein the inhibitory peptide comprises an amino acid sequence according to any one of SEQ ID NOs: 61, 62, 63, 67, and 69.

4. The method of claim 3, wherein the gp100 TCR comprises an alpha domain comprising the amino acid sequence of SEQ ID NO: 7 and the gp100 TCR comprises a beta domain comprising the amino acid sequence of SEQ ID NO: 8.

5. A method of inhibiting an interaction of a T cell receptor (TCR) with a peptide-major histocompatibility (pMHC) complex, the method comprising administering to the TCR and the pMHC an inhibitory peptide that binds to the TCR without the aid of a MHC, thereby inhibiting the interaction of the TCR with the pMHC complex, wherein the TCR comprises a TCR alpha extracellular domain comprising a variable region of the alpha extracellular domain of the TCR and a TCR beta extracellular domain comprising a variable region of the beta extracellular domain of the TCR; and wherein the TCR is a HIV TCR, and wherein the inhibitory peptide comprises an amino acid sequence according to SEQ ID NO: 106.

6. The method of claim 5, wherein the HIV TCR comprises an alpha domain comprising the amino acid sequence of SEQ ID NO: 9 and the HIV TCR comprises a beta domain comprising the amino acid sequence of SEQ ID NO: 10.

\* \* \* \* \*

SEQUENCE LISTING

<160> NUMBER OF SEQ ID NOS: 150

<210> SEQ ID NO 1
<211> LENGTH: 9
<212> TYPE: PRT

<213> ORGANISM: Artificial Sequence
<220> FEATURE:
<223> OTHER INFORMATION: Description of Artificial Sequence: Synthetic
    peptide

<400> SEQUENCE: 1

Glu Val Asp Pro Ile Gly His Leu Tyr
1               5

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 2

Val Ser Cys Lys Asp Val Tyr Asp Glu Ala Phe Cys Trp
1               5                   10

<210> SEQ ID NO 3
<211> LENGTH: 219
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 3

Met Lys Gln Glu Val Thr Gln Ile Pro Ala Ala Leu Ser Val Pro Glu
1               5                   10                  15

Gly Glu Asn Leu Val Leu Asn Cys Ser Phe Thr Asp Ser Ala Ile Tyr
                20                  25                  30

Asn Leu Gln Trp Phe Arg Gln Asp Pro Gly Lys Gly Leu Thr Ser Leu
            35                  40                  45

Leu Tyr Val Arg Pro Tyr Gln Arg Glu Gln Thr Ser Gly Arg Leu Asn
        50                  55                  60

Ala Ser Leu Asp Lys Ser Ser Gly Arg Ser Thr Leu Tyr Ile Ala Ala
65                  70                  75                  80

Ser Gln Pro Gly Asp Ser Ala Thr Tyr Leu Cys Ala Val Arg Pro Gly
                85                  90                  95

Gly Ala Gly Pro Phe Phe Val Val Phe Gly Lys Gly Thr Lys Leu Ser
                100                 105                 110

Val Ile Pro Asn Ile Gln Asn Pro Asp Pro Ala Val Tyr Gln Leu Arg
            115                 120                 125

Asp Ser Lys Ser Ser Asp Lys Ser Val Cys Leu Phe Thr Asp Phe Asp
        130                 135                 140

Ser Gln Thr Asn Val Ser Gln Ser Lys Asp Ser Asp Val Tyr Ile Thr
145                 150                 155                 160

Asp Lys Cys Val Leu Asp Met Arg Ser Met Asp Phe Lys Ser Asn Ser
            165                 170                 175

Ala Val Ala Trp Ser Asn Lys Ser Asp Phe Ala Cys Ala Asn Ala Phe
            180                 185                 190

Asn Asn Ser Ile Ile Pro Glu Asp Thr Phe Phe Pro Ser Pro Glu Ser
        195                 200                 205

Ser Gly Gly His His His His His His His
    210                 215

<210> SEQ ID NO 4

```
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Lys Ala Gly Val Thr Gln Thr Pro Arg Tyr Leu Ile Lys Thr Arg
1               5                   10                  15

Gly Gln Gln Val Thr Leu Ser Cys Ser Pro Ile Ser Gly His Arg Ser
                20                  25                  30

Val Ser Trp Tyr Gln Gln Thr Pro Gly Gln Gly Leu Gln Phe Leu Phe
            35                  40                  45

Glu Tyr Phe Ser Glu Thr Gln Arg Asn Lys Gly Asn Phe Pro Gly Arg
        50                  55                  60

Phe Ser Gly Arg Gln Phe Ser Asn Ser Arg Ser Glu Met Asn Val Ser
65                  70                  75                  80

Thr Leu Glu Leu Gly Asp Ser Ala Leu Tyr Leu Cys Ala Ser Ser Phe
                85                  90                  95

Asn Met Ala Thr Gly Gln Tyr Phe Gly Pro Gly Thr Arg Leu Thr Val
                100                 105                 110

Thr Glu Asp Leu Lys Asn Val Phe Pro Pro Glu Val Ala Val Phe Glu
            115                 120                 125

Pro Ser Glu Ala Glu Ile Ser His Thr Gln Lys Ala Thr Leu Val Cys
        130                 135                 140

Leu Ala Thr Gly Phe Tyr Pro Asp His Val Glu Leu Ser Trp Trp Val
145                 150                 155                 160

Asn Gly Lys Glu Val His Ser Gly Val Cys Thr Asp Pro Gln Pro Leu
                165                 170                 175

Lys Glu Gln Pro Ala Leu Asn Asp Ser Arg Tyr Ala Leu Ser Ser Arg
                180                 185                 190

Leu Arg Val Ser Ala Thr Phe Trp Gln Asn Pro Arg Asn His Phe Arg
            195                 200                 205

Cys Gln Val Gln Phe Tyr Gly Leu Ser Glu Asn Asp Glu Trp Thr Gln
        210                 215                 220

Asp Arg Ala Lys Pro Val Thr Gln Ile Val Ser Ala Glu Ala Trp Gly
225                 230                 235                 240

Arg Ala Asp Gly Gly Gly Leu Asn Asp Ile Phe Glu Ala Gln Lys Ile
                245                 250                 255

Glu Trp His Glu
            260

<210> SEQ ID NO 5
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Gly Gly Val Ser Cys Lys Asp Val Tyr Asp Glu Ala Phe Cys Trp
1               5                   10                  15

Thr Gly Gly Gly Gly Ser Leu Ser Gly Arg Ser Asp Asn His Gly Ser
                20                  25                  30

Ser Gly Thr Lys Gln Glu Val Thr Gln Ile Pro Ala Ala Leu Ser Val
            35                  40                  45
```

-continued

```
Pro Glu Gly Glu Asn Leu Val Leu Asn Cys Ser Phe Thr Asp Ser Ala
    50              55              60

Ile Tyr Asn Leu Gln Trp Phe Arg Gln Asp Pro Gly Lys Gly Leu Thr
65              70              75              80

Ser Leu Leu Tyr Val Arg Pro Tyr Gln Arg Glu Gln Thr Ser Gly Arg
            85              90              95

Leu Asn Ala Ser Leu Asp Lys Ser Ser Gly Arg Ser Thr Leu Tyr Ile
            100             105             110

Ala Ala Ser Gln Pro Gly Asp Ser Ala Thr Tyr Leu Cys Ala Val Arg
            115             120             125

Pro Gly Gly Ala Gly Pro Phe Phe Val Val Phe Gly Lys Gly Thr Lys
    130             135             140

Leu Ser Val Ile Pro Asn Ile Gln Asn Pro Asp Pro Ala Val Tyr Gln
145             150             155             160

Leu Arg Asp Ser Lys Ser Ser Asp Lys Ser Val Cys Leu Phe Thr Asp
            165             170             175

Phe Asp Ser Gln Thr Asn Val Ser Gln Ser Lys Asp Ser Asp Val Tyr
            180             185             190

Ile Thr Asp Lys Cys Val Leu Asp Met Arg Ser Met Asp Phe Lys Ser
            195             200             205

Asn Ser Ala Val Ala Trp Ser Asn Lys Ser Asp Phe Ala Cys Ala Asn
    210             215             220

Ala Phe Asn Asn Ser Ile Ile Pro Glu Asp Thr Phe Phe Pro Ser Pro
225             230             235             240

Glu Ser Ser Gly Gly His His His His His His His
            245             250
```

```
<210> SEQ ID NO 6
<211> LENGTH: 294
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6
```

```
Met Gly Gly Val Ser Cys Lys Asp Val Tyr Asp Glu Ala Phe Cys Trp
1               5               10              15

Thr Gly Gly Gly Gly Ser Leu Ser Gly Arg Ser Asp Asn His Gly Ser
            20              25              30

Ser Gly Thr Lys Ala Gly Val Thr Gln Thr Pro Arg Tyr Leu Ile Lys
            35              40              45

Thr Arg Gly Gln Gln Val Thr Leu Ser Cys Ser Pro Ile Ser Gly His
    50              55              60

Arg Ser Val Ser Trp Tyr Gln Gln Thr Pro Gly Gln Gly Leu Gln Phe
65              70              75              80

Leu Phe Glu Tyr Phe Ser Glu Thr Gln Arg Asn Lys Gly Asn Phe Pro
            85              90              95

Gly Arg Phe Ser Gly Arg Gln Phe Ser Asn Ser Arg Ser Glu Met Asn
            100             105             110

Val Ser Thr Leu Glu Leu Gly Asp Ser Ala Leu Tyr Leu Cys Ala Ser
            115             120             125

Ser Phe Asn Met Ala Thr Gly Gln Tyr Phe Gly Pro Gly Thr Arg Leu
    130             135             140

Thr Val Thr Glu Asp Leu Lys Asn Val Phe Pro Pro Glu Val Ala Val
```

-continued

```
145                 150                 155                 160

Phe Glu Pro Ser Glu Ala Glu Ile Ser His Thr Gln Lys Ala Thr Leu
            165             170             175

Val Cys Leu Ala Thr Gly Phe Tyr Pro Asp His Val Glu Leu Ser Trp
            180             185             190

Trp Val Asn Gly Lys Glu Val His Ser Gly Val Cys Thr Asp Pro Gln
            195             200             205

Pro Leu Lys Glu Gln Pro Ala Leu Asn Asp Ser Arg Tyr Ala Leu Ser
        210             215             220

Ser Arg Leu Arg Val Ser Ala Thr Phe Trp Gln Asn Pro Arg Asn His
    225             230             235             240

Phe Arg Cys Gln Val Gln Phe Tyr Gly Leu Ser Glu Asn Asp Glu Trp
                245             250             255

Thr Gln Asp Arg Ala Lys Pro Val Thr Gln Ile Val Ser Ala Glu Ala
            260             265             270

Trp Gly Arg Ala Asp Gly Gly Gly Leu Asn Asp Ile Phe Glu Ala Gln
            275             280             285

Lys Ile Glu Trp His Glu
    290

<210> SEQ ID NO 7
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Ser Gln Gln Gly Glu Glu Asp Pro Gln Ala Leu Ser Ile Gln Glu
1               5                   10                  15

Gly Glu Asn Ala Thr Met Asn Cys Ser Tyr Lys Thr Ser Ile Asn Asn
            20              25              30

Leu Gln Trp Tyr Arg Gln Asn Ser Gly Arg Gly Leu Val His Leu Ile
        35              40              45

Leu Ile Arg Ser Asn Glu Arg Glu Lys His Ser Gly Arg Leu Arg Val
    50              55              60

Thr Leu Asp Thr Ser Lys Lys Ser Ser Ser Leu Leu Ile Thr Ala Ser
65              70              75              80

Arg Ala Ala Asp Thr Ala Ser Tyr Phe Cys Ala Thr Asp Gly Ser Thr
            85              90              95

Pro Met Gln Phe Gly Lys Gly Thr Arg Leu Ser Val Ile Ala Asn Ile
            100             105             110

Gln Lys Pro Asp Pro Ala Val Tyr Gln Leu Arg Asp Ser Lys Ser Ser
        115             120             125

Asp Lys Ser Val Cys Leu Phe Thr Asp Phe Asp Ser Gln Thr Asn Val
        130             135             140

Ser Gln Ser Lys Asp Ser Asp Val Tyr Ile Thr Asp Lys Cys Val Leu
145             150             155             160

Asp Met Arg Ser Met Asp Phe Lys Ser Asn Ser Ala Val Ala Trp Ser
            165             170             175

Asn Lys Ser Asp Phe Ala Cys Ala Asn Ala Phe Asn Asn Ser Ile Ile
            180             185             190

Pro Glu Asp Thr Phe Phe Pro Ser Pro Glu Ser Ser Gly Gly His His
        195             200             205
```

-continued

```
His His His His His His
    210

<210> SEQ ID NO 8
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Asp Gly Gly Ile Thr Gln Ser Pro Lys Tyr Leu Phe Arg Lys Glu
1               5                   10                  15

Gly Gln Asn Val Thr Leu Ser Cys Glu Gln Asn Leu Asn His Asp Ala
            20                  25                  30

Met Tyr Trp Tyr Arg Gln Asp Pro Gly Gln Gly Leu Arg Leu Ile Tyr
        35                  40                  45

Tyr Ser Trp Ala Gln Gly Asp Phe Gln Lys Gly Asp Ile Ala Glu Gly
    50                  55                  60

Tyr Ser Val Ser Arg Glu Lys Lys Glu Ser Phe Pro Leu Thr Val Thr
65                  70                  75                  80

Ser Ala Gln Lys Asn Pro Thr Ala Phe Tyr Leu Cys Ala Ser Ser Trp
                85                  90                  95

Gly Ala Pro Tyr Glu Gln Tyr Phe Gly Pro Gly Thr Arg Leu Thr Val
            100                 105                 110

Thr Glu Asp Leu Lys Asn Val Phe Pro Pro Glu Val Ala Val Phe Glu
        115                 120                 125

Pro Ser Glu Ala Glu Ile Ser His Thr Gln Lys Ala Thr Leu Val Cys
    130                 135                 140

Leu Ala Thr Gly Phe Tyr Pro Asp His Val Glu Leu Ser Trp Trp Val
145                 150                 155                 160

Asn Gly Lys Glu Val His Ser Gly Val Cys Thr Asp Pro Gln Pro Leu
                165                 170                 175

Lys Glu Gln Pro Ala Leu Asn Asp Ser Arg Tyr Ala Leu Ser Ser Arg
            180                 185                 190

Leu Arg Val Ser Ala Thr Phe Trp Gln Asp Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240

Arg Ala Asp Gly Gly Gly Leu Asn Asp Ile Phe Glu Ala Gln Lys Ile
                245                 250                 255

Glu Trp His Glu
            260

<210> SEQ ID NO 9
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Gln Lys Glu Val Glu Gln Asn Ser Gly Pro Leu Ser Val Pro Glu
1               5                   10                  15
```

-continued

```
Gly Ala Ile Ala Ser Leu Asn Cys Thr Tyr Ser Asp Arg Gly Ser Gln
         20                  25                  30

Ser Phe Phe Trp Tyr Arg Gln Tyr Ser Gly Lys Ser Pro Glu Leu Ile
         35                  40                  45

Met Phe Ile Tyr Ser Asn Gly Asp Lys Glu Asp Gly Arg Phe Thr Ala
         50                  55                  60

Gln Leu Asn Lys Ala Ser Gln Tyr Ile Ser Leu Leu Ile Arg Asp Ser
65                  70                  75                  80

Lys Leu Ser Asp Ser Ala Thr Tyr Leu Cys Ala Val Arg Gly Ala His
                 85                  90                  95

Asp Tyr Ala Leu Asn Phe Gly Lys Gly Thr Ser Leu Leu Val Thr Pro
             100                 105                 110

His Ile Gln Lys Pro Asp Pro Ala Val Tyr Gln Leu Arg Asp Ser Lys
         115                 120                 125

Ser Ser Asp Lys Ser Val Cys Leu Phe Thr Asp Phe Asp Ser Gln Thr
     130                 135                 140

Asn Val Ser Gln Ser Lys Asp Ser Asp Val Tyr Ile Thr Asp Lys Cys
145                 150                 155                 160

Val Leu Asp Met Arg Ser Met Asp Phe Lys Ser Asn Ser Ala Val Ala
                 165                 170                 175

Trp Ser Asn Lys Ser Asp Phe Ala Cys Ala Asn Ala Phe Asn Asn Ser
             180                 185                 190

Ile Ile Pro Glu Asp Thr Phe Phe Pro Ser Pro Glu Ser Ser Gly Gly
             195                 200                 205

His His His His His His His His
     210                 215

<210> SEQ ID NO 10
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Glu Ala Gly Val Thr Gln Ser Pro Thr His Leu Ile Lys Thr Arg
1               5                   10                  15

Gly Gln Gln Val Thr Leu Arg Cys Ser Pro Lys Ser Gly His Asp Thr
             20                  25                  30

Val Ser Trp Tyr Gln Gln Ala Leu Gly Gln Gly Pro Gln Phe Ile Phe
         35                  40                  45

Gln Tyr Ala Leu Gly Glu Glu Arg Gln Arg Gly Asn Phe Pro Asp Arg
     50                  55                  60

Phe Ser Gly His Gln Phe Pro Asn Tyr Ser Ser Glu Leu Asn Val Asn
65                  70                  75                  80

Ala Leu Leu Leu Gly Asp Ser Ala Leu Tyr Leu Cys Ala Ser Ser Asp
                 85                  90                  95

Thr Val Ser Tyr Glu Gln Tyr Phe Gly Pro Gly Thr Arg Leu Thr Val
             100                 105                 110

Thr Glu Asp Leu Lys Asn Val Phe Pro Pro Glu Val Ala Val Phe Glu
         115                 120                 125

Pro Ser Glu Ala Glu Ile Ser His Thr Gln Lys Ala Thr Leu Val Cys
     130                 135                 140

Leu Ala Thr Gly Phe Tyr Pro Asp His Val Glu Leu Ser Trp Trp Val
145                 150                 155                 160
```

-continued

```
Asn Gly Lys Glu Val His Ser Gly Val Cys Thr Asp Pro Gln Pro Leu
            165                 170                 175

Lys Glu Gln Pro Ala Leu Asn Asp Ser Arg Tyr Ala Leu Ser Ser Arg
            180                 185                 190

Leu Arg Val Ser Ala Thr Phe Trp Gln Asp Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240

Arg Ala Asp Gly Gly Gly Leu Asn Asp Ile Phe Glu Ala Gln Lys Ile
            245                 250                 255

Glu Trp His Glu
            260
```

```
<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Glu Ser Cys Gln Ser Val Tyr Asp Ser Ser Phe Cys Tyr Asp
1               5                   10                  15
```

```
<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Asn Ala Cys Glu Met Thr Tyr Asp His Thr Phe Cys Asp Pro
1               5                   10                  15
```

```
<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Arg Ile Cys Glu Glu Val Tyr Asp Trp Ile Phe Cys Glu Ser
1               5                   10                  15
```

```
<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Gly Arg Arg Cys Val Asp Val Tyr Asp Asn Ala Phe Cys Leu Ile
1               5                   10                  15
```

```
<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Gly Val Ser Cys Lys Asp Val Tyr Asp Glu Ala Phe Cys Trp Thr
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gly Thr Ser Cys Ala Gln Ile Tyr Asp Phe Glu Phe Cys Tyr Ser
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gly Ser Leu Cys Ser Leu Val Tyr Asp Gln Asp Phe Cys Glu Ser
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Gly Asn Ser Cys Ser Leu Val Tyr Asp Lys Ala Phe Cys Leu Phe
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Gly Asn Gln Cys Trp Glu Val Tyr Asp Gln Glu Phe Cys Ser Leu
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20
```

Gly Gly Ser Ala Cys Ser Arg Ile Tyr Asp Phe Ala Phe Cys His Thr
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gly Thr Phe Cys Tyr Phe Asp His Gly Leu Val Asn Cys Gln Trp
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Gly His Cys Phe Val Ser Pro Ala Ser Gly Glu Trp Trp Cys Val
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Cys Ser Trp Ile Phe Asp Gly Leu Arg Tyr Phe Ser Lys Cys
1               5                   10                  15

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Val Arg Thr Trp Phe Glu Lys Phe Pro Glu Leu Val
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Leu Val Trp Gly Cys Ile Trp Asp Asp Met Cys Ser
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Trp His Trp Glu Pro Ser Met Val Trp Gly Met Leu
1               5                   10

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Gly Gly Cys Phe Val Ser Pro Ala Thr Gly Phe Thr Trp Cys Val
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Gly Asp Cys Gln Pro Asp Ser Val Trp Ser Tyr Trp Tyr Cys Arg
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Gly Cys Thr Phe Val Asp Trp Trp Val Leu Gly Ser Pro Tyr Cys
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Gly Cys Leu Met Asn Asp Tyr Tyr Tyr Leu Trp Gly Gly His Cys
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Gly Ala Ser Cys Lys Asp Val Tyr Asp Glu Ala Phe Cys Trp Thr
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Gly Val Ala Cys Lys Asp Val Tyr Asp Glu Ala Phe Cys Trp Thr
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Gly Val Ser Cys Ala Asp Val Tyr Asp Glu Ala Phe Cys Trp Thr
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Gly Val Ser Cys Lys Asp Val Tyr Asp Ala Ala Phe Cys Trp Thr
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Gly Val Ser Cys Lys Asp Val Tyr Asp Glu Ala Phe Cys Ala Thr
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Gly Val Ser Cys Lys Asp Val Tyr Asp Glu Ala Phe Cys Trp Ala
1               5                   10                  15

<210> SEQ ID NO 37
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 37

Gly Gly Glu Ser Cys Gln Ser Val Tyr Asp Ser Ser Phe Cys Tyr Asp
1               5                   10                  15

Gly Gly Gly Gly Ser
            20

<210> SEQ ID NO 38
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Gly Asn Ala Cys Glu Met Thr Tyr Asp His Thr Phe Cys Asp Pro
1               5                   10                  15

Gly Gly Gly Gly Ser
            20

<210> SEQ ID NO 39
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Gly Arg Ile Cys Glu Glu Val Tyr Asp Trp Ile Phe Cys Glu Ser
1               5                   10                  15

Gly Gly Gly Gly Ser
            20

<210> SEQ ID NO 40
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Gly Arg Arg Cys Val Asp Val Tyr Asp Asn Ala Phe Cys Leu Ile
1               5                   10                  15

Gly Gly Gly Gly Ser
            20

<210> SEQ ID NO 41
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Gly Val Ser Cys Lys Asp Val Tyr Asp Glu Ala Phe Cys Trp Thr
1               5                   10                  15

Gly Gly Gly Gly Ser
            20

<210> SEQ ID NO 42
<211> LENGTH: 21
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Gly Thr Ser Cys Ala Gln Ile Tyr Asp Phe Glu Phe Cys Tyr Ser
1               5                   10                  15

Gly Gly Gly Gly Ser
            20

<210> SEQ ID NO 43
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Gly Ser Leu Cys Ser Leu Val Tyr Asp Gln Asp Phe Cys Glu Ser
1               5                   10                  15

Gly Gly Gly Gly Ser
            20

<210> SEQ ID NO 44
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Gly Asn Ser Cys Ser Leu Val Tyr Asp Lys Ala Phe Cys Leu Phe
1               5                   10                  15

Gly Gly Gly Gly Ser
            20

<210> SEQ ID NO 45
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Gly Asn Gln Cys Trp Glu Val Tyr Asp Gln Glu Phe Cys Ser Leu
1               5                   10                  15

Gly Gly Gly Gly Ser
            20

<210> SEQ ID NO 46
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Gly Ser Ala Cys Ser Arg Ile Tyr Asp Phe Ala Phe Cys His Thr
1               5                   10                  15
```

```
Gly Gly Gly Gly Ser
            20

<210> SEQ ID NO 47
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Gly Thr Phe Cys Tyr Phe Asp His Gly Leu Val Asn Cys Gln Trp
1               5                   10                  15

Gly Gly Gly Gly Ser
            20

<210> SEQ ID NO 48
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Gly His Cys Phe Val Ser Pro Ala Ser Gly Glu Trp Trp Cys Val
1               5                   10                  15

Gly Gly Gly Gly Ser
            20

<210> SEQ ID NO 49
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Gly Cys Ser Trp Ile Phe Asp Gly Leu Arg Tyr Phe Ser Lys Cys
1               5                   10                  15

Gly Gly Gly Gly Ser
            20

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Val Arg Thr Trp Phe Glu Lys Phe Pro Glu Leu Val Gly Gly Gly Gly
1               5                   10                  15

Ser

<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 51

Leu Val Trp Gly Cys Ile Trp Asp Asp Met Cys Ser Gly Gly Gly Gly
1               5                   10                  15

Ser

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Trp His Trp Glu Pro Ser Met Val Trp Gly Met Leu Gly Gly Gly Gly
1               5                   10                  15

Ser

<210> SEQ ID NO 53
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Gly Gly Cys Phe Val Ser Pro Ala Thr Gly Phe Thr Trp Cys Val
1               5                   10                  15

Gly Gly Gly Gly Ser
            20

<210> SEQ ID NO 54
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Gly Asp Cys Gln Pro Asp Ser Val Trp Ser Tyr Trp Tyr Cys Arg
1               5                   10                  15

Gly Gly Gly Gly Ser
            20

<210> SEQ ID NO 55
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Gly Cys Thr Phe Val Asp Trp Trp Val Leu Gly Ser Pro Tyr Cys
1               5                   10                  15

Gly Gly Gly Gly Ser
            20

<210> SEQ ID NO 56
<211> LENGTH: 21
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 56

Gly Gly Cys Leu Met Asn Asp Tyr Tyr Tyr Leu Trp Gly Gly His Cys
1               5                   10                  15

Gly Gly Gly Gly Ser
            20

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Glu Val Asp Pro Ile Gly His Leu Tyr Gly Gly Gly Gly Ser
1               5                   10

<210> SEQ ID NO 58
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Glu Ser Asp Pro Ile Val Ala Gln Tyr Gly Gly Gly Gly Ser
1               5                   10

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Gly Ala Leu Cys Pro Gln Val His Gly Ser Phe Ser Phe Cys Phe
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Gly Cys His Trp Glu His Val Trp Gly Ala Gly Ser Phe Phe Cys
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61
```

```
Gly Gly Tyr Asp Cys Asn Tyr Asp Pro Ser Ser His Thr Cys Phe Tyr
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Gly Asp Ile Cys Gln Trp Val Arg Ser Met Thr Glu Cys Ser Trp
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Gly Tyr Cys Tyr Tyr Asp Ile Asp Leu Asp Gln Phe Leu Cys Asn
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Gly Trp Cys Ser Tyr Val Arg Phe Asp Phe Ile Asp Phe Cys Leu
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Gly Thr Cys Ile Trp Phe Asp Val Glu Ser Trp Leu Ser Cys Phe
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Gly Leu Cys Arg Ala Val Glu Asp Met Trp Val Thr Ser Cys Met
1               5                   10                  15

<210> SEQ ID NO 67
<211> LENGTH: 16
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 67

Gly Gly Ile Cys Tyr Asp Tyr Met Ser Gly Tyr Asp Val Val Cys Met
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Gly His Cys Tyr Asp Thr His Ser Phe Pro Met Tyr Val Cys Leu
1               5                   10                  15

<210> SEQ ID NO 69
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Gly Tyr Cys Pro Leu Ser Tyr Ser Gln Tyr Asp Ser Pro Cys Tyr
1               5                   10                  15

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Gly Asp Ile Cys Gln Trp Val Lys His Glu Ser Tyr Cys Thr Ser
1               5                   10                  15

<210> SEQ ID NO 71
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Gly Phe Leu Cys Tyr Leu Tyr Glu His Asn Gly Ala Cys Leu Leu
1               5                   10                  15

<210> SEQ ID NO 72
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Gly Met Phe Cys Trp Gly Phe Gly Asp His Trp Phe Cys Ser Pro
1               5                   10                  15

-continued

```
<210> SEQ ID NO 73
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Gly Asp Cys Trp Trp Phe Pro Ser Asp Pro His Pro Phe Cys Phe
1               5                   10                  15

<210> SEQ ID NO 74
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Gly Phe Cys Arg Tyr Val Arg Tyr Glu Phe Trp Asp Leu Cys Met
1               5                   10                  15

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Gly His Cys Tyr Phe Asn Glu Gly Leu Gln Tyr Phe Ser Cys Trp
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Gly Ile Cys Tyr Asp Tyr Met Ala Gly Asp Asp Val Leu Cys Met
1               5                   10                  15

<210> SEQ ID NO 77
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Gly Leu Cys Arg Thr Ile Tyr Ser Tyr Ala Gly Thr Val Cys Trp
1               5                   10                  15

<210> SEQ ID NO 78
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78
```

```
Gly Gly Leu Cys Ser Tyr Ile Lys Trp Glu Phe Gln Tyr Leu Cys Leu
1               5                   10                  15

<210> SEQ ID NO 79
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Gly Leu Cys Tyr Asp Thr His Ser Phe Pro Met Tyr Val Cys Leu
1               5                   10                  15

<210> SEQ ID NO 80
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Gly Ser Cys Arg Thr Ile Tyr Glu Tyr Ser His Met Glu Cys Asp
1               5                   10                  15

<210> SEQ ID NO 81
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Gly Val Cys Asp Trp Pro Thr Ser Asp Met Glu Trp Trp Cys Phe
1               5                   10                  15

<210> SEQ ID NO 82
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Gly Trp Cys Arg Ala Ile Tyr Arg Tyr Met Gly Thr Val Cys Glu
1               5                   10                  15

<210> SEQ ID NO 83
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Gly Tyr Cys Pro Leu Ser Tyr Ser His Asp Asp Ile Pro Cys Tyr
1               5                   10                  15

<210> SEQ ID NO 84
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 84

Gly Gly Tyr Cys Ser Ile Thr Gly Gly Glu Glu Ile Ala Gln Cys Val
1               5                   10                  15

<210> SEQ ID NO 85
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Gly Ile Phe Pro Cys Leu Ser Asp Arg Trp Leu Cys Val Asp Phe
1               5                   10                  15

<210> SEQ ID NO 86
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Gly Ile Phe Pro Cys Leu Ser Asp Arg Trp Leu Cys Val Asp Phe
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Gly Ile Phe Pro Cys Leu Ser Asp Arg Trp Leu Cys Val Asp Phe
1               5                   10                  15

<210> SEQ ID NO 88
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Gly Cys His Trp Glu His Val Trp Gly Ala Gly Ser Phe Phe Cys
1               5                   10                  15

Gly Gly Gly Gly Ser
            20

<210> SEQ ID NO 89
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89
```

```
Gly Gly Tyr Asp Cys Asn Tyr Asp Pro Ser Ser His Thr Cys Phe Tyr
1               5                   10                  15

Gly Gly Gly Gly Ser
            20

<210> SEQ ID NO 90
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Gly Asp Ile Cys Gln Trp Val Arg Ser Met Thr Glu Cys Ser Trp
1               5                   10                  15

Gly Gly Gly Gly Ser
            20

<210> SEQ ID NO 91
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Gly Tyr Cys Tyr Tyr Asp Ile Asp Leu Asp Gln Phe Leu Cys Asn
1               5                   10                  15

Gly Gly Gly Gly Ser
            20

<210> SEQ ID NO 92
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Gly Phe Cys Arg Tyr Val Arg Tyr Glu Phe Trp Asp Leu Cys Met
1               5                   10                  15

Gly Gly Gly Gly Ser
            20

<210> SEQ ID NO 93
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Gly Leu Cys Arg Ala Val Glu Asp Met Trp Val Thr Ser Cys Met
1               5                   10                  15

Gly Gly Gly Gly Ser
            20

<210> SEQ ID NO 94
<211> LENGTH: 21
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 94

Gly Gly Ile Cys Tyr Asp Tyr Met Ser Gly Tyr Asp Val Val Cys Met
1               5                   10                  15

Gly Gly Gly Gly Ser
            20

<210> SEQ ID NO 95
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Gly His Cys Tyr Asp Thr His Ser Phe Pro Met Tyr Val Cys Leu
1               5                   10                  15

Gly Gly Gly Gly Ser
            20

<210> SEQ ID NO 96
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Gly Tyr Cys Pro Leu Ser Tyr Ser Gln Tyr Asp Ser Pro Cys Tyr
1               5                   10                  15

Gly Gly Gly Gly Ser
            20

<210> SEQ ID NO 97
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Gly Asp Pro Cys Asn Ile Tyr Asn Tyr Trp Thr Thr Cys Val Thr
1               5                   10                  15

<210> SEQ ID NO 98
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Gly Ser Asn Cys Tyr Ser Leu Glu Pro Trp Ile Tyr Cys Asp Thr
1               5                   10                  15

<210> SEQ ID NO 99
<211> LENGTH: 16
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 99

Gly Gly Leu Val Cys Asn Asp Gly Asn Ile Trp Trp Leu Cys Glu Asp
1               5                   10                  15

<210> SEQ ID NO 100
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Gly Phe Thr Cys Val Asp Gly Gln Val Tyr Tyr Leu Cys Asp Ser
1               5                   10                  15

<210> SEQ ID NO 101
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Gly Gly Thr Cys Phe His Gly Asn Thr Tyr Phe Leu Cys Glu Asp
1               5                   10                  15

<210> SEQ ID NO 102
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Gly Gln Thr Cys Ile Ala Asp Asn Val Tyr Tyr Leu Cys Pro Glu
1               5                   10                  15

<210> SEQ ID NO 103
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Gly Met Leu Cys Asn Glu Gly Tyr Trp Ala Leu Ser Cys Phe Leu
1               5                   10                  15

<210> SEQ ID NO 104
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Gly Val Ile Cys Thr Ala Asp Gly Val Tyr Trp Leu Cys Asp Leu
1               5                   10                  15
```

-continued

```
<210> SEQ ID NO 105
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Gly Val Thr Cys Asn Asp Gly Lys Ile Phe Tyr Leu Cys Ser Asp
1               5                   10                  15

<210> SEQ ID NO 106
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Gly Ala Phe Cys Val Asp Thr Lys Pro Gly Leu Val Cys Phe Glu
1               5                   10                  15

<210> SEQ ID NO 107
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Gly Ala Thr Cys His Leu Asp Asn Val Tyr Phe Leu Cys Asp Ile
1               5                   10                  15

<210> SEQ ID NO 108
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Gly Thr Thr Cys Leu Glu Gly Gly Val Tyr Phe Leu Cys Ala Asp
1               5                   10                  15

<210> SEQ ID NO 109
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Gly Leu Val Cys Asn Asp Gly Val Val Phe Trp Leu Cys Asp Ser
1               5                   10                  15

<210> SEQ ID NO 110
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 110

Gly Gly Ile Glu Cys Tyr Pro Gly Phe Trp Ala Leu Asp Cys Leu Tyr
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Gly Val Thr Cys Ser Leu Gly Asn Val Phe Tyr Leu Cys His Asp
1               5                   10                  15

<210> SEQ ID NO 112
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Gly Gln Leu Cys Pro Glu Gly Tyr Tyr Ala Leu Met Cys Thr Asp
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Gly Leu Thr Cys Ser Ser Gln Asn Ile Tyr Tyr Leu Cys Ser Asp
1               5                   10                  15

<210> SEQ ID NO 114
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gly Gly Ile Val Cys Ser Val Gly Leu Ile Tyr Phe Leu Cys Ala Asp
1               5                   10                  15

<210> SEQ ID NO 115
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Gly Phe His Cys Gly Gly Leu Val Tyr Ser Leu Asp Cys Ser Tyr
1               5                   10                  15

<210> SEQ ID NO 116
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 116

Gly Gly Phe His Cys Gly Gly Leu Val Tyr Ser Leu Asp Cys Ser Tyr
1               5                   10                  15

<210> SEQ ID NO 117
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gly Gly Val His Cys Gly Asp Asn Ile Trp Ser Leu His Cys Phe Leu
1               5                   10                  15

<210> SEQ ID NO 118
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly Gly Leu Met Cys Tyr Leu Asp Gly Asn Ser Ser Ile Cys Val Ser
1               5                   10                  15

<210> SEQ ID NO 119
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gly Gly Pro Cys Arg Asp Leu Phe Ser Glu Val Leu Tyr Pro Cys Leu
1               5                   10                  15

<210> SEQ ID NO 120
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Gly Tyr Cys Trp Leu Asp Tyr Ser Ile Leu Ser Gln Asp Cys Ile
1               5                   10                  15

<210> SEQ ID NO 121
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gly Gly Pro Phe Cys Val Asp Ala Ser Ala Asp Arg Ala Cys Phe Trp
1               5                   10                  15
```

<210> SEQ ID NO 122
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gly Gly Pro Cys Asp Asn Ile Tyr Tyr Lys Tyr Phe Tyr Thr Cys Leu
1               5                   10                  15

<210> SEQ ID NO 123
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gly Gly Thr Cys Tyr Ser Glu Asp Gly Ala Tyr Tyr Tyr Leu Cys Met
1               5                   10                  15

<210> SEQ ID NO 124
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gly Gly Asp Thr Cys Val His Asn Gly Val Tyr Phe Leu Cys Val Asp
1               5                   10                  15

<210> SEQ ID NO 125
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gly Gly Leu Val Cys Asn Met Gly Glu Met Tyr Phe Leu Cys Asp Val
1               5                   10                  15

<210> SEQ ID NO 126
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Gly Leu Thr Cys Asn Arg Asp Asn Val Phe Tyr Leu Cys Val Asp
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide -continued

<400> SEQUENCE: 127

Gly Gly Ser Leu Cys Ser Asp Gly Tyr Trp Ser Leu Asn Cys Glu Phe
1               5                   10                  15

<210> SEQ ID NO 128
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gly Gly Ser Asn Cys Tyr Ser Leu Glu Pro Trp Ile Tyr Cys Asp Thr
1               5                   10                  15

Gly Gly Gly Gly Ser
            20

<210> SEQ ID NO 129
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gly Gly Leu Val Cys Asn Asp Gly Asn Ile Trp Trp Leu Cys Glu Asp
1               5                   10                  15

Gly Gly Gly Gly Ser
            20

<210> SEQ ID NO 130
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Gly Phe Thr Cys Val Asp Gly Gln Val Tyr Tyr Leu Cys Asp Ser
1               5                   10                  15

Gly Gly Gly Gly Ser
            20

<210> SEQ ID NO 131
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gly Gly Gly Thr Cys Phe His Gly Asn Thr Tyr Phe Leu Cys Glu Asp
1               5                   10                  15

Gly Gly Gly Gly Ser
            20

<210> SEQ ID NO 132
<211> LENGTH: 21
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 132

Gly Gly Gln Thr Cys Ile Ala Asp Asn Val Tyr Tyr Leu Cys Pro Glu
1               5                   10                  15

Gly Gly Gly Gly Ser
            20

<210> SEQ ID NO 133
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gly Gly Met Leu Cys Asn Glu Gly Tyr Trp Ala Leu Ser Cys Phe Leu
1               5                   10                  15

Gly Gly Gly Gly Ser
            20

<210> SEQ ID NO 134
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gly Gly Val Ile Cys Thr Ala Asp Gly Val Tyr Trp Leu Cys Asp Leu
1               5                   10                  15

Gly Gly Gly Gly Ser
            20

<210> SEQ ID NO 135
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gly Gly Val Thr Cys Asn Asp Gly Lys Ile Phe Tyr Leu Cys Ser Asp
1               5                   10                  15

Gly Gly Gly Gly Ser
            20

<210> SEQ ID NO 136
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gly Gly Ala Phe Cys Val Asp Thr Lys Pro Gly Leu Val Cys Phe Glu
1               5                   10                  15

Gly Gly Gly Gly Ser
            20
```

```
<210> SEQ ID NO 137
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gly Gly Ala Thr Cys His Leu Asp Asn Val Tyr Phe Leu Cys Asp Ile
1               5                   10                  15

Gly Gly Gly Gly Ser
            20

<210> SEQ ID NO 138
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gly Gly Thr Thr Cys Leu Glu Gly Gly Val Tyr Phe Leu Cys Ala Asp
1               5                   10                  15

Gly Gly Gly Gly Ser
            20

<210> SEQ ID NO 139
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gly Gly Leu Val Cys Asn Asp Gly Val Val Phe Trp Leu Cys Asp Ser
1               5                   10                  15

Gly Gly Gly Gly Ser
            20

<210> SEQ ID NO 140
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gly Gly Ile Glu Cys Tyr Pro Gly Phe Trp Ala Leu Asp Cys Leu Tyr
1               5                   10                  15

Gly Gly Gly Gly Ser
            20

<210> SEQ ID NO 141
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141
```

-continued

```
Gly Gly Val Thr Cys Ser Leu Gly Asn Val Phe Tyr Leu Cys His Asp
1               5                   10                  15

Gly Gly Gly Gly Ser
            20

<210> SEQ ID NO 142
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gly Gly Gln Leu Cys Pro Glu Gly Tyr Tyr Ala Leu Met Cys Thr Asp
1               5                   10                  15

Gly Gly Gly Gly Ser
            20

<210> SEQ ID NO 143
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Gly Leu Thr Cys Ser Ser Gln Asn Ile Tyr Tyr Leu Cys Ser Asp
1               5                   10                  15

Gly Gly Gly Gly Ser
            20

<210> SEQ ID NO 144
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Gly Ile Val Cys Ser Val Gly Leu Ile Tyr Phe Leu Cys Ala Asp
1               5                   10                  15

Gly Gly Gly Gly Ser
            20

<210> SEQ ID NO 145
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gly Gly Phe His Cys Gly Gly Leu Val Tyr Ser Leu Asp Cys Ser Tyr
1               5                   10                  15

Gly Gly Gly Gly Ser
            20

<210> SEQ ID NO 146
<211> LENGTH: 21
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 146

Gly Gly Val His Cys Gly Asp Asn Ile Trp Ser Leu His Cys Phe Leu
1               5                   10                  15

Gly Gly Gly Gly Ser
            20

<210> SEQ ID NO 147
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gly Gly Pro Cys Arg Asp Leu Phe Ser Glu Val Leu Tyr Pro Cys Leu
1               5                   10                  15

Gly Gly Gly Gly Ser
            20

<210> SEQ ID NO 148
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Gly Tyr Cys Trp Leu Asp Tyr Ser Ile Leu Ser Gln Asp Cys Ile
1               5                   10                  15

Gly Gly Gly Gly Ser
            20

<210> SEQ ID NO 149
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Gly Pro Phe Cys Val Asp Ala Ser Ala Asp Arg Ala Cys Phe Trp
1               5                   10                  15

Gly Gly Gly Gly Ser
            20

<210> SEQ ID NO 150
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150
```

-continued

```
Gly Gly Pro Cys Asp Asn Ile Tyr Tyr Lys Tyr Phe Tyr Thr Cys Leu
1           5               10              15

Gly Gly Gly Gly Ser
        20
```